United States Patent
Pandjaitan et al.

(10) Patent No.: US 8,912,127 B2
(45) Date of Patent: Dec. 16, 2014

(54) METHOD OF GENERATING GENE MOSAICS

(75) Inventors: Rudy Pandjaitan, Maisons-Alfort (FR); Alejandro Luque, Paris (FR)

(73) Assignee: Eviagenics, S.A., Villejuif (FR)

( * ) Notice: Subject to any disclaimer, the term of this patent is extended or adjusted under 35 U.S.C. 154(b) by 0 days.

(21) Appl. No.: 13/640,313

(22) PCT Filed: Apr. 8, 2011

(86) PCT No.: PCT/EP2011/055530
§ 371 (c)(1),
(2), (4) Date: Dec. 18, 2012

(87) PCT Pub. No.: WO2011/124693
PCT Pub. Date: Oct. 13, 2011

(65) Prior Publication Data
US 2013/0090246 A1   Apr. 11, 2013

Related U.S. Application Data

(60) Provisional application No. 61/322,680, filed on Apr. 9, 2010.

(30) Foreign Application Priority Data

Apr. 9, 2010   (EP) .................................. 10159515

(51) Int. Cl.
*C12N 15/10* (2006.01)
*C12N 15/90* (2006.01)

(52) U.S. Cl.
CPC ........ *C12N 15/1058* (2013.01); *C12N 15/1082* (2013.01); *C12N 15/902* (2013.01); *C12N 15/1027* (2013.01); *C12N 15/90* (2013.01)
USPC ............................................................ 506/1

(58) Field of Classification Search
CPC ....................................................... C12N 15/905
USPC .................................................................. 506/1
See application file for complete search history.

(56) References Cited

U.S. PATENT DOCUMENTS 5,912,119 A   6/1999   Radman et al.

FOREIGN PATENT DOCUMENTS

| WO | 90/07576 | 7/1990 |
| WO | 97/05268 | 2/1997 |

(Continued)

OTHER PUBLICATIONS

Shao et al, 2009, vol. 37, No. 2, pp. 1-10.*

(Continued)

*Primary Examiner* — Heather Calamita
*Assistant Examiner* — Karla Dines
(74) *Attorney, Agent, or Firm* — Michael Fredrick; Loza & Loza, LLP

(57) ABSTRACT

The invention relates to a method for generating a gene mosaic by somatic in vivo recombination, comprising: e) in a single step procedure (vii) transforming a cell with at least one gene A having a sequence homology of less than 99.5% to another gene to be recombined that is an integral part of the cell genome or presented in the framework of a genetic construct, (viii) recombining said genes, (ix) generating a gene mosaic of the genes at an integration site of a target genome, wherein said at least one gene A has a single flanking target sequence either at the 5' end or 3' end anchoring to the 5' or 3' end of said integration site, and f) selecting clones comprising the gene mosaic, as well as a method of producing a diversity of gene mosaics and gene assembly.

20 Claims, 21 Drawing Sheets

(56) References Cited

FOREIGN PATENT DOCUMENTS

Figure 1:
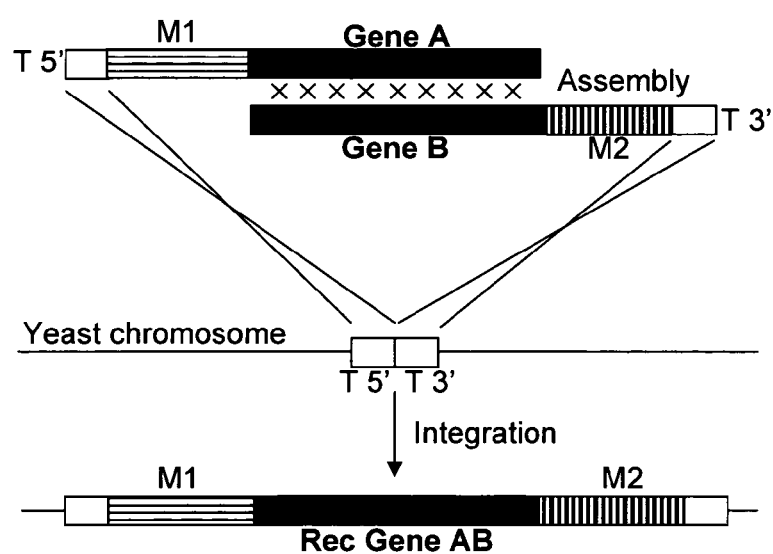

| WO | 03/095658 | 11/2003 |
|---|---|---|
| WO | 2005/075654 | 8/2005 |
| WO | 2006/134496 | 12/2006 |

OTHER PUBLICATIONS

Elefanty et al., Proc. Natl. Acad. Sci., 95: 11897-11902 (1998).
Kunz C et al., Cell. Mol. Life Sci., 66(6):1021-1038 (2009).
Gietz, R.D. and R.A. Woods, Transformation of Yeast by the Liac/SS Carrier DNA/PEG Method, Methods in Enzymology, 350:87-96 (2002).
Nicholson A et al., Genetics, 154(1):133-146 (2000).
Shao Z et al., Nucleic Acids Research, 37(2):e16 (2008).
Swers J et al., Nucleic Acids Research, 32(3):e36 (2004).
Wang P L, Disease Markers (Wiley, Chichester, GB) 16:3-13 (2000).
Weber H et al., Nucleic Acids Research, 11(16):5661-5669 (1983).
Extended European Search Report, European Patent Application No. 10159515.5-2405, Aug. 6, 2010.
International Preliminary Report on Patentability, International Patent Application No. PCT/EP2011/055530, Oct. 18, 2012.
International Search Report, International Patent Application No. PCT/EP2011/055530, Jun. 7, 2011.
Written Opinion of the International Search Authority, PCT/EP2011/055530, Jun. 7, 2011.

* cited by examiner

Fig. 5:

>Fe02 11-7
ATGAAAACATTTGCCGCATATGTAATTATCGCGTGTCTTTCGAGTACGGCATTAGCTAGTTCAATTACAGAAAATACGTTTT
GGAACAAAGAGTTCTCTGCCGAAGCCGTCAATGGTGTTTTCGTGCTTTGTAAAAGTAGCAGTAAATCCTGCGCTACCAAT
AACTTAGCTCGTGCATCAAAGGAATATCTTCCAGCATCAACATTTAAGATCCCCAACGCAATTATCGGCCTAGAAACTGGTG
TCATAAAGAATGAGCATCAGATTTTCAAATGGGACGGAAAACCAAGAGCCATGAAACAATGGGAAAGAGACTTGAGCTTA
AGAGGGGCAATACAAGTTTCAGCGGTTCCCGTATTTCAACAAATCGCCAGAGAAGTTGGCGAAGTAAGAATGCAGAAAT
ATCTTAAAAAATTTTCATATGGTAACCAGAATATCAGTGGCGGCATTGACAAATTCTGGTTGGAGGGTCAGCTTAGAATTT
CCGCAGTTAATCAAGTGGAGTTTCTAGAGTCTCTATTTTTAAATAAATTGTCAGCATCAAAAGAAAATCAGCTAATAGTAA
AAGAGGCTTTGGTAACGGAGGCTGCGCCTGAATATCTTGTGCATTCAAAAACTGGTTTTTCTGGTGTGGGAACTGAGTCA
AATCCTGGTGTCGCATGGTGGGTTGGTTGGGTTGAGAAGGGAGCAGAGGTTTACTTTTTCGCATTTAACATGGATATAGA
CAACGAAAATAAGTTGCCGCTAAGAAAATCCATTCCCACCAAAATCATGGCAAGTGAGGGCATCATTGGTGGCTAA

SEQ ID NO 1

MKTFAAYVIIACLSSTALASSITENTFWNKEFSAEAVNGVFVLCKSSSKSCATNNLARASKEYLPASTFKIPNAIIGLETGVIKNEHQI
FKWDGKPRAMKQWERDLSLRGAIQVSAVPVFQQIAREVGEVRMQKYLKKFSYGNQNISGGIDKFWLEGQLRISAVNQVEFLESL
FLNKLSASKENQLIVKEALVTEAAPEYLVHSKTGFSGVGTESNPGVAWWVGWVEKGAEVYFFAFNMDIDNENKLPLRKSIPTKIM
ASEGIIGG

SEQ ID NO 2

>Fe03 11-7
ATGAAAACATTTGCCGCATATGTAATTATCGCGTGTCTTTCGAGTACGGCATTAGCTGGTTCAATTACAGAAAATACGTCTTG
GAACAAAGAGTTCTCTGCCGAAGCCGTCAATGGTGTCTTCGTGCTTTGTAAAAGTAGCAGTAAATCCTGCGCTACCAATGAC
TTAGCTCGTGCATCAAAGGAATATCTTCCAGCATCAACATTTAAGATCCCCAACGCAATTATCGGCCTAGAAACTGGTGTCA
TAAAGAATGAGCATCAGATTTTCAAATGGGACGGAAAACCAAGAGCCATGAAACAATGGGAAAGAGACTTGACCTTAAGA
GGGGCAATACAAGTTTCAGCGGTTCCCGTATTTCAACAAATCGCCAGAGAAGTTGGCGAAGTAAGAATGCAGAAATATCT
TAAAAAATTTTCATATGGTAACCAGAATATCAGTGGTGGCATTGACAAATTCTGGTCGGAGGGTCAGCTTAGAATTTCCGC
AGTTAATCAAGTGGAGTTTCTAGAGTCTCTATTTTTAAATAAATTGTCAGCATCAAAAGAAAATCAGCTAATAGTAAAAGA
GGCTTTGGTAACGGAGGCTGCGCCTGAATATCTTGTGCATTCAAAAACTGGTTTTTCTGGTGTGGGAACTGAGTCAAATC
CTGGTGTCGCATGGTGGGTTGGTTGGGTTGAGAAGGGAGCAGAGGTTTACTTTTTCGCATTTAACATGGATATAGACAAC
GAAAATAAGTTGCCGCTAAGAAAATCCATTCCCACCAAAATCATGGCAAGTGAGGGCATCATTGGTGGCTAA

SEQ ID NO 3

MKTFAAYVIIACLSSTALAGSITENTSWNKEFSAEAVNGVFVLCKSSSKSCATNDLARASKEYLPASTFKIPNAIIGLETGVIKNEHQI
FKWDGKPRAMKQWERDLTLRGAIQVSAVPVFQQIAREVGEVRMQKYLKKFSYGNQNISGGIDKFWSEGQLRISAVNQVEFLESL
FLNKLSASKENQLIVKEALVTEAAPEYLVHSKTGFSGVGTESNPGVAWWVGWVEKGAEVYFFAFNMDIDNENKLPLRKSIPTKIM
ASEGIIGG

SEQ ID NO 4

>Fe04 11-7
ATGAAAACATTTGCCGCATATGTAATTATCGCGTGTCTTTCGAGTACGGCATTAGCTGGTTCAATTACAGAAAATACGTCTTG
GAACAAAGAGTTCTCTGCCGAAGCCGTCAATGGTGTCTTCGTGCTTTGTAAAAGTAGCAGTAAATCCTGCGCTACCAATGAC
TTAGCTCGTGCATCAAAGGAATATCTTCCAGCATCAACATTTAAGATCCCCAACGCAATTATCGGCCTAGAAACTGGTGTCA
TAAAGAATGAGCATCAGGTTTTCAAATGGGACGGAAAGCCAAGAGCCATGAAGCAATGGGAAAGAGACTTGACCTTAAGAG
GGGCAATACAAGTTTCAGCTGTTCCCGTATTTCAACAAATCGCCAGAGAAGTTGGCGAAGTAAGAATGCAGAAATACCTTAA
AAAATTTTCCTATGGCAGCCAGAATATCAGTGGTGGCATTGACAAATTCTGGTTGGAAGACCAGCTTAGAATTTCCGCAGTT
AATCAAGTGGAGTTTCTAGAGTCTCTATATTTAAATAAATTGTCAGCATCTAAAGAAAACCAGCTAATAGTAAAAGAGGCTTT
GGTAACGGAGGCGGCACCTGAATATCTAGTGCATTCAAAAACTGGTTTTTCTGGTGTGGGAACTGAGTCAAATCCTGGTGT
CGCATGGTGGGTTGGGTGGGTTGAGAAGGAGACAGAGGTTTACTTTTTCGCCTTTAACATGGATATAGACAACGAAAGTAA
GTTGCCGCTAAGAAAATCCATTCCCACCAAAATCAGGGAAAGTGAGGGCATCATTGGTGGCTAA

SEQ ID NO 5

MKTFAAYVIIACLSSTALAGSITENTSWNKEFSAEAVNGVFVLCKSSSKSCATNDLARASKEYLPASTFKIPNAIIGLETGVIKNEHQ
VFKWDGKPRAMKQWERDLTLRGAIQVSAVPVFQQIAREVGEVRMQKYLKKFSYGSQNISGGIDKFWLEDQLRISAVNQVEFLES
LYLNKLSASKENQLIVKEALVTEAAPEYLVHSKTGFSGVGTESNPGVAWWVGWVEKETEVYFFAFNMDIDNESKLPLRKSIPTKIR
ESEGIIGG

SEQ ID NO 6

Fig. 5 continued

>Fe05 11-7
ATGAAAACATTTGCCGCATATGTAATTATCGCGTGTCTTTCGAGTACGGCATTAGCTGGTTCAATTACAGAAAATACGTCTTG
GAACAAAGAGTTCTCTGCCGAAGCCGTCAATGGTGTCTTCGTGCTTTGTAAAAGTAGCAGTAAATCCTGCGCTACCAATGAC
TTAGCTCGTGCA<u>CCAAAGGAATATCTTCCAGCATCAACATTTAAGATCCCCAACGCAATTATCGGCCTAGAAACTGGTGT
CATAAAGAATGAGCATCAG</u>GTTTTCAAATGGGACGGAAAGCCAAGAGCCATGAAGCAATGGGAAAGAGACTTGACCTTAA
GAGGGGCAATACAAGTTTCAGCTGTTCCCGTATTTCAACAAATCGCCAGAGAAGTTGGCGAAGTAAGAATGCAGAAATACC
TTAAAAAATTTTCCTATGGCAGCCAGAATATCAGTGGTGGCATTGACAAAT<u>TCTGGT</u>TGGAAG<u>GTCAGCTTAGAATTTCCGC
AGTTAATCAAGTGGAGTTTCTAGAGTCTCTATTTTTAAATAAATTGTCAGCATCAAAAGAAAATCAGCTAATAGTAAAAGA
GGCTTTGGTAACGGAGGCTGCGCCTGAATATCTTGTGCATTCAAAAACTGGTTTTTCTGGTGTGGGAACTGAGTCAAATC
CTGGTGTCGCATGGTGGGTTGGTTGGGTTGAGAAGGGAGCAGAGGTTTACTTTTTCGCATTTAACATGGATATAGACAAC
GAAAATAAGTTGCCGCTAAGAAAATCCATTCCCACCAAAATCATGGCAAGTGAGGGCATCATTGGTGGCTAA</u>

SEQ ID NO 7

MKTFAAYVIIACLSSTALAGSITENTSWNKEFSAEAVNGVFVLCKSSSKSCATNDLARAPKEYLPASTFKIPNAIIGLETGVIKNEHQ
VFKWDGKPRAMKQWERDLTLRGAIQVSAVPVFQQIAREVGEVRMQKYLKKFSYGSQNISGGIDKFWLEGQLRISAVNQVEFLES
LFLNKLSASKENQLIVKEALVTEAAPEYLVHSKTGFSGVGTESNPGVAWWVGWVEKGAEVYFFAFNMDIDNENKLPLRKSIPTKI
MASEGIIGG

SEQ ID NO 8

>Fe06 11-7
ATGAAAACATTTGCCGCATATGTAATTATCGCGTGTCTTTCGAGTACGGCATTAGCTGGTTCAATTACAGAAAATACGTCTTG
GAACAAAGAGTTCTCTGCCGAAGCCGTCAATGGTGTCTTCGTGCTTTGTAAAAGTAGCAGTAAATCCTGCGCTACCAATGAC
TTAGCTCGTGCATCAAAGGAATATCTTCCAGCATCAACATTTAAGATCCCCAACGCAATTATCGGCCTAGAAACTGGTGTCA
TAAAGAATGAGCATCAGGTTTTCAAATGGGACGGAAAGCCAAGAGCCATGAAGCAATGGGAAAGAGACTTGACCTTAAGAG
GGGCAATACAAGTTTCAGCTGTTCCCGTATTTCAACAAATCGCCAGAGAAGTTGGCGAAGTAAGAATGCAGAAATACCTTAA
AAAATTTTCCTATGGCAGCCAGAATATCAGTGGTGGCATTGACAAAT<u>TCTGGT</u>TGGAAGACCAGCTTAGAATTTCCGCAGTT
AATCAAGTGGAGTTTCTAGAGTCTCTATATTTAAATAAATTGTCAGCATCTAAAGAAAACCAGCTAATAGTAAAAGAGGCTTT
GGTAACGGAGGCGGCACCTGAATATCTAGTGCATTCAAAAACTGGTTTTTCTGGTGTGGGAACTGAGTCAAATCCTGGTGT
CGCATGGTGGGTTGGGTGGGTTGAGAAGGAGACAGAGGTTTACTTTTTCGCCTTTAACATGGATATGGACAACGAAAGTAA
GTTGCCGCTAAGAAAATCCATTCCCACCAAAATCATGGAAAGTGAGGGCATCATTGGTGGCTAA

SEQ ID NO 9

MKTFAAYVIIACLSSTALAGSITENTSWNKEFSAEAVNGVFVLCKSSSKSCATNDLARASKEYLPASTFKIPNAIIGLETGVIKNEHQ
VFKWDGKPRAMKQWERDLTLRGAIQVSAVPVFQQIAREVGEVRMQKYLKKFSYGSQNISGGIDKFWLEDQLRISAVNQVEFLES
LYLNKLSASKENQLIVKEALVTEAAPEYLVHSKTGFSGVGTESNPGVAWWVGWVEKETEVYFFAFNMDMDNESKLPLRKSIPTKI
MESEGIIGG

SEQ ID NO 10

>Fe10 11-7
ATGAAAACATTTGCCGCATATGTAATTA<u>CTGCGTGTCTTTCAAGTACGGCATTAGCTAGTTCAATTACAGAAAATACGTTTT
GGAACAAAGAGTTCTCTGCCGAAGCCGTCAATGGTGTTTTCGTGCTTTGTAAAAGTAGCAGTAAATCCTGCGCTACCTAT
AACTTAGCTCGTGCA</u>TCAAAGGAATATCTTCCAGCATCAACATTTAAGATCCCCAACGCAATTATCGGCCTAGAAACTGGTG
TCATAAAGAATGAGCATCAG<u>ATTTTCAAATGGGACGGAAA</u>GCCAAGAGCCATGAA<u>ACAATGGGAAAGAGACTTGAGCTTA
AGAGGGGCAATACAAGTTTCAGCGGTTCCCGTATTTCAACAAATCGCCAGAGAAGTTGGCGAAGTAAGAATGCAGAAAT
ATCTTAAAAAATTTTCATATGGTAACCAGAATATCAGTGG</u>TGGCATTGACAAAT<u>TCTGGT</u>TGG<u>AGGGTCAGCTTAGAATTT
CCGCAGTTAATCAAGTGGAGTTTCTAGAGTCTCTATTTTTAAATAAATTGTCAGCATCAAAAGAAAATCAGCTAATAGTAA
AAGAGGCTTTGGTAACGGAGGCTGCGCCTGAATATCTTGTGCATTCAAAAACTGGTTTTTCTGGTGTGGGAACTGAGTCA
AATCCTGGTGTCGCATGGTGGGTTGGTTGGGTTGAGAAGGGAGCAGAGGTTTACTTTTTCGCATTTAACATGGATATAGA
CAACGAAAATAAGTTGCCGCTAAGAAAATCCATTCCCACCAAAATCATGGCAAGTGAGGGCATCATTGGTGGCTAA</u>

SEQ ID NO 11

MKTFAAYVITACLSSTALASSITENTFWNKEFSAEAVNGVFVLCKSSSKSCATYNLARASKEYLPASTFKIPNAIIGLETGVIKNEHQ
IFKWDGKPRAMKQWERDLSLRGAIQVSAVPVFQQIAREVGEVRMQKYLKKFSYGNQNISGGIDKFWLEGQLRISAVNQVEFLES
LFLNKLSASKENQLIVKEALVTEAAPEYLVHSKTGFSGVGTESNPGVAWWVGWVEKGAEVYFFAFNMDIDNENKLPLRKSIPTKI
MASEGIIGG

SEQ ID NO 12

Fig. 5 continued

>Fel1 11-7
ATGAAAACATTTGCCGCATATGTAATTATCGCGTGTCTTTCGAGTACGGCATTAGCTGGTTCAATTACAGAAAATACGTCTTG
GAACAAAGAGTTCTCTGCCGAAGCCGTCAATGGTGTCTTCGTGCTTTGTAAAAGTAGCAGTAAATCCTGCGCTACCAATGAC
TTAGCTCGTGCATCAAAGGAATATCTTCCAGCATCAACATTTAAGATCCCCAACGCAATTATCGGCCTAGAAACTGGTGTCA
TAAGGAATGAGCATCAGGTTTTCAAATGGGACGGAAAGCCAAGAGCCATGAAGCAATGGGAAAGAGACTTGACCTTAAGAG
GGGCAATACAAGTTTCAGCTGTTCCCGTATTTCAACAAATCGCCAGAGAAGTTGGCGAAGTAAGAATGCAGAAATACCTTAA
AAAATTTTCCTATGGCAGCCAGAATATCAGTGGTGGCATTGACAAAT<u>TCTGGT</u>TGGAAGACCAGCTTAGAATTTCCGCAGTT
AATCAAGTGGAGTTTCTAGAGTCTCTATATTTAAATAAATTGTCAGCATCTAAAGAAAA<u>TCAGCTAATAGTAAAAGAGGCTTT
GGTAACGGAGGCTGCGCCTGAATATCTTGTGCATTCAAAAACTGGTTTTTCTGGTGTGGGAACTGAGTCAAATCCTGGTG
TCGCATGGTGGGTTGGG</u>GTGGGTTGAGAAGGAGACAGAGGTTTACTTTTTCGC<u>ATTTAACATGGATATAGACAACGAAAAT
AAGTTGCCGCTAAGAAAAT</u>T<u>CATTCCCACCAAAATCATGG</u>CAAGTGAGGGCATCATTGGTGGCTAA

SEQ ID NO 13

MKTFAAYVIIACLSSTALAGSITENTSWNKEFSAEAVNGVFVLCKSSSKSCATNDLARASKEYLPASTFKIPNAIIGLETGVIRNEHQ
VFKWDGKPRAMKQWERDLTLRGAIQVSAVPVFQQIAREVGEVRMQKYLKKFSYGSQNISGGIDKFWLEDQLRISAVNQVEFLES
LYLNKLSASKENQLIVKEALVTEAAPEYLVHSKTGFSGVGTESNPGVAWWVGWVEKETEVYFFAFNMDIDNENKLPLRKFIPTKI
MASEGIIGG

SEQ ID NO 14

Fig. 6:

>Fe09 11-5
ATGAAAACATTTGCCGCATATGTAATTATCGCGTGTCTTTCGAGTACGGCATTAGCTGGTTCAATTACAGAAAATACGTCTTG
GAACAAAGAGTTCTCTGCCGAAGCCGTCAATGGTGTCTTCGTGCTTTGTAAAAGTAGCAGTAAATCCTGCGCTACCAATGAC
TTAGCTCGTGCATCAAAGGAATATCTTCCAGCATCAACATTTAAGATCCCCAACGCAATTATCGGCCTAGAGACTGGTGTCA
TAAAGAATGAGCATCAGGTTTTCAAATGGGACGGAAAGCCAAGAGCCATGAAGCAATGGGAAAGAGACTTGACCTTAAGAG
GGGCAATACAAGTTTCAGCTGTTCCCGTATTTCAACAAATCGCCAGAGAAGTTGGCGAAGTAAGAATGCAGAAATACCTTAA
AAAATTTTCCTATGGCAGCCAGAATATCAGTGGTGGCATTGACAAATTCTGGTTGGAAGACCAGCTTAGAATTTCCGCAGTT
AATCAAGTGGAGTTTCTAGAGTCTCTATATTTAAATAAATTGTCAGCATCTAAAGAAAACCAGCTAATAGTAAAAGAGGC**AAT
AGTTACAGAAGCAACTCCAGAATATATAGTT**CATTCAAAAACTGGTTTTTCTGGTGTGGGAACTGAGTCAAATCCTGGTGT
CGCATGGTGGGTTGGGTGGGTTGAGAAGGAGACAGAGGTTTACTTTTTCGCCTTTAACATGGATATAGACAACGAAAGTAA
GTTGCCGCTAAGAAAATCCATTCCCACCAAAATCATGGAAAGTGAGGGCATCATCATTGGTGGCTAA

SEQ ID NO 15

MKTFAAYVIIACLSSTALAGSITENTSWNKEFSAEAVNGVFVLCKSSSKSCATNDLARASKEYLPASTFKIPNAIIGLETGVIKNEHQ
VFKWDGKPRAMKQWERDLTLRGAIQVSAVPVFQQIAREVGEVRMQKYLKKFSYGSQNISGGIDKFWLEDQLRISAVNQVEFLES
LYLNKLSASKENQLIVKEAIVTEATPEYIVHSKTGFSGVGTESNPGVAWWVGWVEKETEVYFFAFNMDIDNESKLPLRKSIPTKIM
ESEGIIGG

SEQ ID NO 16

>Fe13 11-5
ATGAAAACATTTGCCGCATATGTAATTATCGCGTGTCTTTCGAGTACGGCATTAGCTGGTTCAATTACAGAAAATACGTCTTG
GAACAAAGAGTTCTCTGCCGAAGCCGTCAATGGTGTCTTCGTGCTTTGTAAAAGTAGCAGTAAATCCTGCGCTACCAATGAC
TTAGCTCGTGCATCAAAGGAATATCTTCCAGCATCAACATTTAAGATCCCCAACGCAATTATCGGCCTAGAAACTGGTGTCA
TAAAGAATGAGCATCAGGTTTTCAAATGGGACGGAAAGCCAAGAGCCATGAAGCAATGGGAAAGAGACTTGACCTTAAGAG
GGGCAATACAAGTTTCAGCTGTTCCCGTATTTCAACAAATCGCCAGAGAAGTTGGCGAAGTAAGAATGCAGAAATACCTTAA
AAAATTTTCCTATGGCAGCCAGAATATCAGTGGTGGCATTGACAAATTCTGGTTGGAAGACCAGCTTAGAATTTCCGCAGTT
AATCAAGTGGAGTTTCTAGAGTCTCTATATTTAAATAAATTGTCAGCATCTAAAGAAAACCAGCTAATAGTAAAAGAGGCTTT
GGTAACGGAGGCGGCACCTGAATATCTAGTGCATTCAAAAACTGGTTTTTCTGGTGTGGGAACTGAGTCAAATCCTGGTGT
CGCATGGTGGGTTGGGTGGGTAGAGAAAGGAACTGAGGTTTACTTTTTCGCCTTTAGCATGGATATAGACAACGAAAGTA
AGTTGCCGCTAAGAAAATCCATTCCCACCAAAATCATGGAAAGTGAGGGCATCATTGGTGGCTAA

SEQ ID NO 17

MKTFAAYVIIACLSSTALAGSITENTSWNKEFSAEAVNGVFVLCKSSSKSCATNDLARASKEYLPASTFKIPNAIIGLETGVIKNEHQ
VFKWDGKPRAMKQWERDLTLRGAIQVSAVPVFQQIAREVGEVRMQKYLKKFSYGSQNISGGIDKFWLEDQLRISAVNQVEFLES
LYLNKLSASKENQLIVKEALVTEAAPEYLVHSKTGFSGVGTESNPGVAWWVGWVEKGTEVYFFAFSMDIDNESKLPLRKSIPTKI
MESEGIIGG

SEQ ID NO 18

>Fe14 11-5
ATGAAAACATTTGCCGCATATGTAATTATCGCGTGTCTTTCGAGTACGGCATTAGCTGGTTCAATTACAGAAAATACGTCTTG
GAACAAAGAGTTCTCTGCCGAAGCCGTCAATGGTGTCTTCGTGCTTTGTAAAAGTAGCAGTAAATCCTGCGCTACCAATGAC
TTAGCTCGTGCATCAAAGGAATATCTTCCAGCATCAACATTTAAGATCCCCAACGCAATTATCGGCCTAGAAACTGGTGTCA
TAAAGAATGAGCATCAGGTTTTCAAATGGGACGGAAAGCCAAGAGCCATGAAGCAATGGGAAAGAGACTTGACCTTAAGAG
GGGCAATACAAGTTTCAGCTGTTCCCGTATTTCAACAAATCGCCAGAGAAGTTGGCGAAGTAAGAATGCAGAAATACCTTAA
AAAATTTTCCTATGGCAGCCAGAATATCAGTGGTGGCATTGACAAATTCTGGTTGGAAGACCAGCTTAGAATTTCCGCAGTT
AATCAAGTGGAGTTTCTAGAGTCTCTATATTTAAATAAATTGTCAGCATCTAAAGAAAACCAGCTAATAGTAAAAGAGGCTTT
GGTAACGGAGGCGGCACCTGAATATCTAGTGCATTCAAAAACTGGTTTTTCTGGTGTGGGAACTGAGTCAAATCCTGGTGT
CGCATGGTGGGTTGGGTGGGTTGAGAAGGAGACAGAGGTTTACTTTTTCGCCTTTAACATGGATATAGACAACGA**GAGTAA
ATTGCCGTCAAGAAAATCCATTTCAACGAAAATCATGGCAAGTGAAGGCATCATCATTGGTGGCTAA**

SEQ ID NO 19

MKTFAAYVIIACLSSTALAGSITENTSWNKEFSAEAVNGVFVLCKSSSKSCATNDLARASKEYLPASTFKIPNAIIGLETGVIKNEHQ
VFKWDGKPRAMKQWERDLTLRGAIQVSAVPVFQQIAREVGEVRMQKYLKKFSYGSQNISGGIDKFWLEDQLRISAVNQVEFLES
LYLNKLSASKENQLIVKEALVTEAAPEYLVHSKTGFSGVGTESNPGVAWWVGWVEKETEVYFFAFNMDIDNESKLPSRKSISTKI
MASEGIIGG

SEQ ID NO 20

Fig. 6 continued

>Fe16 11-5
ATGAAAACATTTGCCGCATATGTAATTATCGCGTGTCTTTCGAGTACGGCATTAGCTGGTTCAATTACAGAAAATACGTCTTG
GAACAAAGAGTTCTCTGCCGAAGCCGTCAATGGTGTCTTCGTGCTTTGTAAAAGTAGCAGTAAATCCTGCGCTACCAATGAC
TTAGCTCGTGCATCAAAGGAATATCTTCCAGCATCAACATTTAAGATCCCCAACGCAATTATCGGCCTAGAAACTGGTGTCA
TAAAGAATGAGCATCAGGTTTTCAAATGGGACGGAAAGCCAAGAGCCATGAAGCAATGGGAAAGAGACTTGACCTTAAGAG
GGGCAATACAAGTTTCAGCTGTTCCCGTATTTCAACAAATCGCCAGAGAAGTTGGCGAAGTGAGAATGCAGAAATACCTTAA
AAAATTTTCCTATGGCAGCCAGAATATCAGTGGTGGCATTGACAAATTCTGGTTGGAAGACCAGCTTAGAATTTCCGCAGTT
AATCAAGTGGAGTCTCTAGAGTCTCTATATTTAAATAAATTGTCAGCATCTAAAGAAAACCAGCTAATAGTAAAAGAGGCTTT
GGTAACGGAGGCGGCACCTGAATATCTAGTGCATTCAAAAACTGGTTTTTCTGGTGTGGGAACTGAGTCAAATCCTGGTGT
CGCATGGTGGGTTGGGTGGGTTGAGAAGGAGACAGAGGTTTACTTTTTCGCCTTTAACATGGATATAGACAACGAAAGTAA
GTTGCCGCTAAGAAAATCCATTCCCACCAAAATCATGGAAAGTGAGGGCATCATTGGTGGCTAA

SEQ ID NO 21

MKTFAAYVIIACLSSTALAGSITENTSWNKEFSAEAVNGVFVLCKSSSKSCATNDLARASKEYLPASTFKIPNAIIGLETGVIKNEHQ
VFKWDGKPRAMKQWERDLTLRGAIQVSAVPVFQQIAREVGEVRMQKYLKKFSYGSQNISGGIDKFWLEDQLRISAVNQVESLES
LYLNKLSASKENQLIVKEALVTEAAPEYLVHSKTGFSGVGTESNPGVAWWVGWVEKETEVYFFAFNMDIDNESKLPLRKSIPTKI
MESEGIIGG

SEQ ID NO 22

>Fe17 11-5
ATGAAAACATTTGCCGCATATGTAATTATCGCGTGTCTTTCGAGTACGGCATTAGCTGGTTCAATTACAGAAAATACGTCTTG
GAACAAAGAGTTCTCTGCCGAAGCCGTCAATGGTGTCTTCGTGCTTTGTAAAAGTAGCAGTAAATCCTGCGCTACCAATGAC
TTAGCTCGTGCATCAAAGGAATATCTTCCAGCATCAACATTTAAGATCCCCAACGCAATTATCGGCCTAGAAACTGGTGTCA
TAAAGAATGAGCATCAGGTTTTCAAATGGGACGGAAAGCCAAGAGCCATGAAGCAATGGGAAAGAGACTTGACCTTAAGAG
GGGCAATACAAGTTTCAGCTGTTCCCGTATTTCAACAAATCGCCAGAGAAGTTGGCGAAGTAAGAATGCAGAAATACCTTAA
AAAATTTTCCTATGGCAGCCAGAATATCAGTGGTGGCATTGACAAATTCTGGTTGGAAGACCAGCTTAGAATTTCCGCAGTT
AATCAAGAGGAGTTTCTAGAGTCTCTATATTTAAATAAATTGTCAGCATCTAAAGAAAACCAGCTAATAGTAAAAGAGGCTTT
GGTAACGGAGGCGGCACCTGAATATCTAGTGCATTCAAAAACTGGTTTTTCTGGTGTGGGAACTGAGTCAAATCCTGGTGT
CGCATGGTGGGTTGGGTGGGTTGAGAAGGAGACAGAGGTTTACTTTTTCGCCTTTAACATGGATATAGACAACGAAAGTAA
GTTGCCGCTAAGAAAATCCATTCCCACCAAAATCATGGAAAGTGAGGGCATCAT<u>CATTGGTGGCTAA</u>

SEQ ID NO 23

MKTFAAYVIIACLSSTALAGSITENTSWNKEFSAEAVNGVFVLCKSSSKSCATNDLARASKEYLPASTFKIPNAIIGLETGVIKNEHQ
VFKWDGKPRAMKQWERDLTLRGAIQVSAVPVFQQIAREVGEVRMQKYLKKFSYGSQNISGGIDKFWLEDQLRISAVNQEEFLES
LYLNKLSASKENQLIVKEALVTEAAPEYLVHSKTGFSGVGTESNPGVAWWVGWVEKETEVYFFAFNMDIDNESKLPLRKSIPTKI
MESEGIIGG

SEQ ID NO 24

>Fe18 11-5
ATGAAAACATTTGCCGCATATGTAATTATCGCGTGTCTTTCGAGTACGGCATTAGCTGGTTCAATTACAGAAAATACGTCTTG
GAACAAAGAGTTCTCTGCCGAAGCCGTCAATGGTGTCTTCGTGCTTTGTAAAAGTAGCAGTAAATCCTGCGCTACCAATGAC
TTAGCTCGTGCATCAAAGGAATATCTTCCAGCATCAACATTTAAGATCCCCAACGCAATTATCGGCCTAGAAACTGGTGTCA
TAAAGAATGAGCATCAGGTTTTCAAATGGGACGGAAAGCCAAGAGCCATGAAGCAATGGGAAAGAGACTTGAGCTTAAGAG
GGGCAATACAAGTTTCAGCTGTTCCCGTATTTCAACAAATCGCCAGAGAAGTTGGCGAAGTAAGAATGCAGAGATACCTTAA
AAAATTTTCCTATGGCAGCCAGAATATCAGTGGTGGCATTGACAAATTCTGGTTGGAAGACCAGCTTAGAATTTCCGCAGTT
AATCAAGTGGAGTTTCTAGAGTCTCTATATTTAAATAAATTGTCAGCATCTAAAGAAAACCAGCTAATAGTAAAAGAGGCTTT
GGTAACGGAGGCGGCACCTGAATATCTAGTGCATTCAAAAACTGGTTTTTCTGGTGTGGGAACTGAGTCAAATCCTGGTGT
CGCATGGTGGGTTGGGTGGGTTG<u>**GGAAGGAGACAGAGGTTTACTTTTTCGCCTTTAACATGGATATAGACAACGAAAGT
AAGTTGCCGCTAAGAAAATCCATTCCCACCAAAATCATGGAAAGTGAGGGCATCATTGGTGGCTAA**</u>

SEQ ID NO 25

MKTFAAYVIIACLSSTALAGSITENTSWNKEFSAEAVNGVFVLCKSSSKSCATNDLARASKEYLPASTFKIPNAIIGLETGVIKNEHQ
VFKWDGKPRAMKQWERDLSLRGAIQVSAVPVFQQIAREVGEVRMQRYLKKFSYGSQNISGGIDKFWLEDQLRISAVNQVEFLES
LYLNKLSASKENQLIVKEALVTEAAPEYLVHSKTGFSGVGTESNPGVAWWVGWVGKETEVYFFAFNMDIDNESKLPLRKSIPTKI
MESEGIIGG

SEQ ID NO 26

Fig. 6 continued

>Fe19 11-5
ATGAAAACATTTGCCGCATATGTAATTACTGCGTGTCTTTCAAGTACGGCATTAGCTAGTTCAATTACAGAAAATACGTTTTG
GAACAAAGAGTTCTCTGCCGAAGCCGTCAATGGTGTTTTTTCGTGCTTTGTAAAAGTAGCAGTAAATCCTGCGCTACCAATA
ACTTAGCTCGTGCATCAAAGGAATATCTTCCAGCATCAACATTTAAGATCCCCAACGCAATTATCGGCCTAGAAACTGGTGT
CATAAAGAATGAGCATCAGGTTTTCAAATGGGACGGAAAGCCAAGAGCCATGAAACAATGGGAAAGAGACTTGAGCTTAAG
AGGGGCAATACAAGTTTCAGCGGTTCCCGTATTTCAACAAATCGCCAGAGAAGTTGGCGAAGTAAGAATGCAGAAATATCTT
AAAAAATTTTCATATGGTAACCAGAATATCAGTGGTGGCATTGACAAATTCTGGTTGGAGGGTCAGCTTAGAAT**TTCCGCAG
TTAATCAAGTGGAGTTTCTAGAGTCTCTATTTTTAAATAAATTGTCAGCATCAAAAGAAAATCAGCTAATAGTAAAAGAGGCT
TTGGTAACGGAGGC*T*GCGCCTGAATATCT*T*GTGCATTCAAAAACTGGTTTTTCTGGTGTGGGAACTGAGTCAAATCCTGGTG
TCGCATGGTGGGTTGGTTGGGTGAGAAGGGAGCAGAGGTTTACTTTTTCGCATTTAACATGGATATAGACAACGAAAATA
AGTTGCCGCTAAGAAAATCCATTCCCACCAAATCATGGCAAGTGAGGGCATCATTGGTGGCTAA

SEQ ID NO 27

MKTFAAYVITACLSSTALASSITENTFWNKEFSAEAVNGVFVLCKSSSKSCATNNLARASKEYLPASTFKIPNAIIGLETGVIKNEHQ
VFKWDGKPRAMKQWERDLSLRGAIQVSAVPVFQQIAREVGEVRMQKYLKKFSYGNQNISGGIDKFWLEGQLRISAVNQVEFLES
LFLNKLSASKENQLIVKEALVTEAAPEYLVHSKTGFSGVGTESNPGVAWWVGWVEKGAEVYFFAFNMDIDNENKLPLRKSIPTKI
MASEGIIGG

SEQ ID NO 28

>Fe20 11-5
ATGAAAACATTTGCCGCATACGTAATTACTGCGTGTCTTTCAAGTACGGCATTAGCTAGTTCAATTACAGAAAATACGTTTTG
GAACAAAGAGTTCTCTGCCGAAGCCGTCAATGGTGTTTTCGTGCTTTGTAAAAGTAGCAGTAAATCCTGCGCTACCAATGAC
TTAGCTCGTGCATCAAAGGAATATCTTCCAGCATCAACATTTAAGATCCCCAACGCAATTATCGGCCTAGAAACTGGTGTCA
TAAAGAATGAGCATCAGATTTTCAAATGGGACGGAAAGCCAAGAGCCATGAAGCAATGGGAAAGAGACTTGACCTTAAGAG
GGGCAATACAAGTTTCAGCTGTTCCCGTATTTCAACAAATCGCCAGAGAAGTTGGCGAAGTAAGAATGCAGAAATACCTTAA
AAAATTTTCATATGGTAACCAGAATATCAGTGGTGGCATTGACAAATTCTGGTTGGAGGGTCAGCTTAGAATTCCCGCAGTT
AATCAAGTGGAGTTTCTAGAGTCTCTATTTTTAAATAAATTGTCAGCATCAAAAGAAAATCAGCTAATAGTAAAAGAGGCTTT
GGTAACGGAGGCGGCACCTGAATATCTTTGTGCATTCAAAAACTGGTTTTTCTGGTGTGGGAACTGAGTCAAATCCTGGTGT
CGCATGGTGGGTTGGTTGGGTGAGAAGGGAGCAGAGGTTTACTTTTTCGCATTTAACATGGATATAGACAACGAAAATAA
GTTGCCGCTAAGAAAATCCATTCCCACCAAATCATGGCAAGTGAGGGCATCATTGGTGGCTAA

SEQ ID NO 29

MKTFAAYVITACLSSTALASSITENTFWNKEFSAEAVNGVFVLCKSSSKSCATNDLARASKEYLPASTFKIPNAIIGLETGVIKNEHQ
IFKWDGKPRAMKQWERDLTLRGAIQVSAVPVFQQIAREVGEVRMQKYLKKFSYGNQNISGGIDKFWLEGQLRIPAVNQVEFLES
LFLNKLSASKENQLIVKEALVTEAAPEYLVHSKTGFSGVGTESNPGVAWWVGWVEKGAEVYFFAFNMDIDNENKLPLRKSIPTKI
MASEGIIGG

SEQ ID NO 30

>Fe21 11-5
ATGAAAACATTTGCCGCATATGTAATTATCGCGTGTCTTTCGAGTACGGCATTAGCTGGTTCAATTACAGAAAATACGTCTTG
GAACAAAGAGTTCTCTGCCGAAGCCGTCAATGGTGTCTTCGTGCTTTGTAAAAGTAGCAGTAAATCCTGCGCTACCAATGAC
TTAGCTCGTGCATCAAAGGAATATCTTCCAGCATCAACATTTAAGATCCCCAACGCAATTATCGGCCTAGAAACTGGTGTCA
TAAAGAATGAGCATCAGGTTTTCAAATGGGACGGAAAGCCAAGAGCCATGAAGCAATGGGAAAGAGACTTGACCTTAAGAG
GGGCAATACAAGTTTCAGCTGTTCCCGTATTTCAACAAATCGCCAGAGAAGTTGGCGAAGTAAGAATGCAGAAATACCTTAA
AAAATTTTCCTATGGCAGCCAGAATATCAGTGGTGGCATTGACAAATTCTGGTTGGAAGACCAGCTTAGAATTTCCGCAGTT
AATCAAGTGGAGTTTCTAGAGTCTCTATATTTAAATAAATTGTCAGCATCTAAAGAAAACCAGCTAATAGTAAAAGAGGCTTT
GGTAACGGAGGCGGCACCTGAATATCTAGTGCATTCAAAAACTGGTTTTTCTGGTGTGGGAACTGAGTCAAATCCTGGTGT
CGCATGGTGGGTTGGGTGGGTTGAGAAGGAGACAGAGGTTTACTTTTTCGCCTTTAACATGGATATAGACAACGAAAGTAA
GTTGCCGCTAAGAAAATCCATTCCCACCAAATCATGGAAAGTGAGGGCATCATTGGTGGCTAA

SEQ ID NO 31

MKTFAAYVIIACLSSTALAGSITENTSWNKEFSAEAVNGVFVLCKSSSKSCATNDLARASKEYLPASTFKIPNAIIGLETGVIKNEHQ
VFKWDGKPRAMKQWERDLTLRGAIQVSAVPVFQQIAREVGEVRMQKYLKKFSYGSQNISGGIDKFWLEDQLRISAVNQVEFLES
LYLNKLSASKENQLIVKEALVTEAAPEYLVHSKTGFSGVGTESNPGVAWWVGWVEKETEVYFFAFNMDIDNESKLPLRKSIPTKI
MESEGIIGG

SEQ ID NO 32

Fig. 6 continued

>Fe22 11-5
ATGAAAACATTTGCCGCATATGTAATTATCGCGTGTCTTTCGAGTACGGCATTAGCTGGTTCAATTACAGAAAATACGTCTTG
GAACAAAGAGTTCTCTGCCGAAGCCGTCAATGGTGTCTTCGTGCTTTGTAAAAGTAGCAGTAAATCCTGCGCTACCAATGAC
TTAGCTCGTGCATCAAAGGAATATCTTCCAGCATCAACATTTAAGATCCCCAACGCAATTATCGGCCTAGAAACTGGTGTCA
TAAAGAATGAGCATCAGGTTTTCAAATGGGACGGAAAGCCAAGAGCCATGAAGCAATGGGAAAGAGACTTGACCTTAAGAG
GGGCAATACAAGTTTCAGCTGTTCCCGTATTTCAACAAATCGCCAGAGAAGTTGGCGAAGTAAGAATGCAGAAATACCTTAA
AAAATTTTCCTATGGCAGCCAGAATATCAGTGGTGGCATTGACAAATTCTGGTTGGAAGACCAGCTTAGAATTTCCGCAGTT
AATCAAGTGGAGTTTCTAGAGTCTCTATATTTAAATAAATTGTCAGCATCTAAAGAAAACCAGCTAATAGTAAAAGAGGCTTT
GGTAACGGAGGCGGCACCTGAACATCTAGTGCATTCAAAAACTGGTTTTTCTGGTGTGGGAACTGAGTCAAATCCTGGTGT
CGCATGGTGGGTTGGGTGGGTTGAGAAGGAGACAGAGGTTTACTTTTTCGCCTTTAACATGGACATAGACAACGAAAGTAA
GTTGCCGCTAAGAAAATCCATTCCCACCAAAATCATGGAAAGTGAGGGCATCATTGGTGGCTAA

SEQ ID NO 33

MKTFAAYVIIACLSSTALAGSITENTSWNKEFSAEAVNGVFVLCKSSSKSCATNDLARASKEYLPASTFKIPNAIIGLETGVIKNEHQ
VFKWDGKPRAMKQWERDLTLRGAIQVSAVPVFQQIAREVGEVRMQKYLKKFSYGSQNISGGIDKFWLEDQLRISAVNQVEFLES
LYLNKLSASKENQLIVKEALVTEAAPEHLVHSKTGFSGVGTESNPGVAWWVGWVEKETEVYFFAFNMDIDNESKLPLRKSIPTKI
MESEGIIGG

SEQ ID NO 34

>Fe23 11-5
ATGAAAACATTTGCCGCATATTTAATTATCGCGTGTCTTTCGAGTACGGCATTAGCTGGTTCAATTACAGAAAATACGTCTTG
GAACAAAGAGTTCTCTGCCGAAGCCGTCAATGGTGTCTTCGTGCTTTGTAAAAGTAGCAGTAAATCCTGCGCTACCAATGAC
TTAGCTCGTGCATCAAAGGAATATCTTCCAGCATCAACATTTAAGATCCCCAACGCAATTATCGGCCTAGAAACTGGTGTCA
TAAAGAATGAGCATCAGGTTTTCAAATGGGACGGAAAGCCAAGAGCCATGAAGCAATGGGAAAGAGACTTGACCTTAAGAG
GGGCAATACAAGTTTCAGCTGTTCCCGTATTTCAACAAATCGCCAGAGAAGTTGGCGAAGTAAGAATGCAGAAATACCTTAA
AAAATTTTCCTATGGCAGCCAGAATATCAGTGGTGGCATTGACAAATTCTGGTTGGAAGACCAGCTTAGAATTTCCGCAGTT
AATCAAGTGGAGTTTCTAGAGTCTCTATATTTAAATAAATTGTCAGCATCTAAAGAAAACCAGCTAATAGTAAAAGAGGCTTT
GGTAACGGAGGCGGCACCTGAATATCTAGTGCATTCAAAAACTGGTTTTTCTGGTGTGGGAACTGAGTCAAATCCTGGTGT
CGCATGGTGGGTTGGGTGGGTTGAGAAGGAGACAGAGGTTTACTTTTTCGCCTTTAACATGGATATAGACAACGAAAGTAA
GTTGCCGCTAAGAAAATCCATTCCCACCAAAATCATGGAAAGTGAGGGCATCATCATTGGTGGCTTA

SEQ ID NO 35

MKTFAAYLIIACLSSTALAGSITENTSWNKEFSAEAVNGVFVLCKSSSKSCATNDLARASKEYLPASTFKIPNAIIGLETGVIKNEHQ
VFKWDGKPRAMKQWERDLTLRGAIQVSAVPVFQQIAREVGEVRMQKYLKKFSYGSQNISGGIDKFWLEDQLRISAVNQVEFLES
LYLNKLSASKENQLIVKEALVTEAAPEYLVHSKTGFSGVGTESNPGVAWWVGWVEKETEVYFFAFNMDIDNESKLPLRKSIPTKI
MESEGIIGG

SEQ ID NO 36

>Fe24 11-5
ATGAAAACATTTGCCGCATATGTAATTATCGCGTGTCTTTCGAGTACGGCATTAGCTGGTTCAATTACAGAAAATACGTCTTG
GAACAAAGAGTTCTCTGCCGAAGCCGTCAATGGTGTCTTCGTGCTTTGTAAAAGTAGCAGTAAATCCTGCGCTACCAATGAC
TTAGCTCGTGCATCAAAGGAATATCTTCCAGCATCAACATTTAAGATCCCCAACGCAATTATCGGCCTAGAAACTGGTGTCA
TAAAGAATGAGCATCAGGTTTTCAAATGGGACGGAAAGCCAAGAGCCATGAAGCAATGGGAAAGAGACTTGACCTTAAGAG
GGGCAATACAAGTTTCTGCTGTTCCCGTATTTCAACAAATCGCCAGAGAAGTTGGCGAAGTAAGAATGCAGAAATACCTTAA
AAAATTTTCCTATGGCAGCCAGAATATCAGTGGTGGCATTGACAAATTCTGGTTGGAAGACCAGCTTAGAATTTCCGCAGTT
AATCAAGTGGAGTTTCTAGAGTCTCTATATTTAAATAAATTGTCAGCATCTAAAGAAAACCAGCTAATAGTAAAAGAGGCTTT
GGTAACGGAGGCGGCACCTGAATATCTAGTGCATTCAAAAACTGGTTTTTCTGGTGTGGGAACTGAGTCAAATCCTGGTGT
CGCATGGTGGGTTGGGTGGGTTGAGAAGGAGACTGAGGTTTACTTTTTTGCTTCTAACATGGACATAGACAATGAGAGTAA
ATTGCCGTCAAGAAAATCCATTTCAACGAAAATCATGGCAAGTGAAGGCATCATCATTGGTGGCTAA

SEQ ID NO 37

MKTFAAYVIIACLSSTALAGSITENTSWNKEFSAEAVNGVFVLCKSSSKSCATNDLARASKEYLPASTFKIPNAIIGLETGVIKNEHQ
VFKWDGKPRAMKQWERDLTLRGAIQVSAVPVFQQIAREVGEVRMQKYLKKFSYGSQNISGGIDKFWLEDQLRISAVNQVEFLES
LYLNKLSASKENQLIVKEALVTEAAPEYLVHSKTGFSGVGTESNPGVAWWVGWVEKETEVYFFASNMDIDNESKLPSRKSISTKI
MASEGIIGG

SEQ ID NO 38

Fig. 7

OXA11 (parental)

ATGAAAACATTTGCCGCATATGTAATTATCGCGTGTCTTTCGAGTACGGCATTAGCTGGT
TCAATTACAGAAAATACGTCTTGGAACAAAGAGTTCTCTGCCGAAGCCGTCAATGGTGTC
TTCGTGCTTTGTAAAAGTAGCAGTAAATCCTGCGCTACCAATGACTTAGCTCGTGCATCA
AAGGAATATCTTCCAGCATCAACATTTAAGATCCCCAACGCAATTATCGGCCTAGAAACT
GGTGTCATAAAGAATGAGCATCAGGTTTTCAAATGGGACGGAAAGCCAAGAGCCATGAAG
CAATGGGAAAGAGACTTGACCTTAAGAGGGGCAATACAAGTTTCAGCTGTTCCCGTATTT
CAACAAATCGCCAGAGAAGTTGGCGAAGTAAGAATGCAGAAATACCTTAAAAAATTTTCC
TATGGCAGCCAGAATATCAGTGGTGGCATTGACAAATCCTGGTTGGAAGACCAGCTTAGA
ATTTCCGCAGTTAATCAAGTGGAGTTTCTAGAGTCTCTATATTTAAATAAATTGTCAGCA
TCTAAAGAAAACCAGCTAATAGTAAAAGAGGCTTTGGTAACGGAGGCGGCACCTGAATAT
CTAGTGCATTCAAAAACTGGTTTTTCTGGTGTGGGAACTGAGTCAAATCCTGGTGTCGCA
TGGTGGGTTGGGTGGGTTGAGAAGGAGACAGAGGTTTACTTTTTCGCCTTTAACATGGAT
ATAGACAACGAAAGTAAGTTGCCGCTAAGAAAATCCATTCCCACCAAAATCATGGAAAGT
GAGGGCATCATTGGTGGCTAA

SEQ ID NO 39

OXA07 (parental)

ATGAAAACATTTGCCGCATATGTAATTACTGCGTGTCTTTCAAGTACGGCATTAGCTAGT
TCAATTACAGAAAATACGTTTTGGAACAAAGAGTTCTCTGCCGAAGCCGTCAATGGTGTT
TTCGTGCTTTGTAAAAGTAGCAGTAAATCCTGCGCTACCAATAACTTAGCTCGTGCACCA
AAGGAATATCTTCCAGCATCAACATTTAAGATCCCCAACGCAATTATCGGCCTAGAAACT
GGTGTCATAAAGAATGAGCATCAGATTTTCAAATGGGACGGAAAACCAAGAGCCATGAAA
CAATGGGAAAGAGACTTGAGCTTAAGAGGGGCAATACAAGTTTCAGCGGTTCCCGTATTT
CAACAAATCGCCAGAGAAGTTGGCGAAGTAAGAATGCAGAAATATCTTAAAAAATTTTCA
TATGGTAACCAGAATATCAGTGGCGGCATTGACAAATTCTGGTCGGAGGGTCAGCTTAGA
ATTTCCGCAGTTAATCAAGTGGAGTTTCTAGAGTCTCTATTTTTAAATAAATTGTCAGCA
TCAAAAGAAAATCAGCTAATAGTAAAAGAGGCTTTGGTAACGGAGGCTGCGCCTGAATAT
CTTGTGCATTCAAAAACTGGTTTTTCTGGTGTGGGAACTGAGTCAAATCCTGGTGTCGCA
TGGTGGGTTGGTTGGGTTGAGAAGGGAGCAGAGGTTTACTTTTTCGCATTTAACATGGAT
ATAGACAACGAAATAAGTTGCCGCTAAGAAAATCCATTCCCACCAAAATCATGGCAAGT
GAGGGCATCATTGGTGGCTAA

SEQ ID NO 40

OXA05 (parental)

ATGAAACCATAGCCGCATACTTAGTTACTTCCTGTTTTTCAAGCACCGCGCTCTCAAAG
TCTATTTCTGAAAATTTGGTGTGGAATAAAGAATTTTCTAGTGAATCCGTACATGGCGTT
TTTGTACTTTGTAAAAGTAGTAGCAATTCCTGTACTACAAATAATGCGGCACGTGCATCT
ACAGCCTATATTCCAGCATCAACATTCAAAATTCCTAATGCTCTAATAGGTCTTGAAACC
GGCGCCATAAAAGATGAACGGCAGATTTTCAAATGGGACGGCAAGCCCAGAGCCATGAAA
CAATGGGAAAAAGACTTAAGGCTAAGGGGCGCTATACAGGTTTCTGCGGTTCCGGTATTT
CAACAAATTGCCAGAGAAGTTGGCGAAATGAGAATGCAAAGATATCTTAACCTGTTTTCA
TACGGTAACGCCAATATAGGGGGAGGCATTGACAAATTCTGGCTAGAGGGTCAGCTTAGA
ATCCCAGCATTCAATCAAGATAAATCTTTAGAGTCGCTCTTCCTGAATAATTTGCCAGCA
TCAAAAGCAAATCAACTAATAGTAAAAGAGGCAATAGTTACAGAAGCTACGCCAGAATAT
ATTGTTCATTCAAAAACTGGGTATTCCGGTGTTGGCACAGAATCAAGTCCTGGTGTCGCT
TGGTGGGTTGGTGGGTAGGGAAAGGAGCTGAGGTTTACTTTTTGCATTTAACATGGAC
ATAGACAATGAGAATAAATTGCCGTCAAGAAAATCCATTTCAACGAAAATCATGGCAAGT
GAAGGCATCATCATTGGTGGCTAA

SEQ ID NO 41

Fig. 8 a) >OUL3-05-II
ATGAAAACATTTGCCGCATATGTAATTATCGCGTGTCTTTCGAGTACGGCATTAGCTGGTTC
AATTACAGAAAATACGTCTTGGAACAAAGAGTTCTCTGCCGAAGCCGTCAATGGTGTCTTCG
TGCTTTGTAAAAGTAGCAGTAAATCCTGCGCTACCAATGACTTAGCTCGTGCATCAAAGGAA
TATCTTCCAGCATCAACATT<u>CAAAATTCCTAATGCTCTAATAGGTCTTGAAACCGGCGCCAT
AAAAGATGAACGGCAGGTTTTCAAATGGGACGGCAAGCCCAGAGCCATGAAGCAATGGGAAA
AAGACTTAAAGCTAAGGGGCGCTATACAGGTTTCTGCTGTTCCGGTATTTCAACAAATTGCC
AGAGAAGTTGGCGAAATAAGAATGCAAAAATACCTTAACCTGTTTTCATACGGCAACGCCAA
TATAGGGGGAGGCATTGACAAATTCTGGCTAGAAGGTCAGCTTAGAATCTCAGCATTCAATC
AAGTTAAATTTTTAGAGTCGCTCTACCTGAATAATTTGCCAGCATCAAAAGCAAACCAACTA
ATAGTAAAAGAGGCAATAGTTACAGAAGCAACTCCAGAATATATAGTTCATTCAAAAACTGG
GTATTCCGGTGTTGGCACAGAATCAAGTCCTGGTGTCGCTTGGTGGGTTGGTTGGGTAGAGA
AAGGAACTGAGGTTTACTTTTTTGCTTTTAACATGGACATAGACAATGAGAGTAAATTGCCG
TCAAGAAAATCCATTCC</u>**CACCAAAATCATGGCAAGTGAGGGCATCATTGGTGGCTAAGCTGT
GAAGATCCCAGCAAAGGCTTA**

SEQ ID NO 42

MKTFAAYVIIACLSSTALAGSITENTSWNKEFSAEAVNGVFVLCKSSSKSCATNDLARASKE
YLPASTFKIPNALIGLETGAIKDERQVFKWDGKPRAMKQWEKDLKLRGAIQVSAVPVFQQIA
REVGEIRMQKYLNLFSYGNANIGGGIDKFWLEGQLRISAFNQVKFLESLYLNNLPASKANQL
IVKEAIVTEATPEYIVHSKTGYSGVGTESSPGVAWWVGWVEKGTEVYFFAFNMDIDNESKLP
SRKSIPTKIMASEGIIGG.

SEQ ID NO 43

Fig. 8 (continued).

b) >OUL3-05-III

ATGAAAACATTTGCCGCATATTTAGTTCTCGCGTGTCTTTCGAGTACGGCATTAGCTGGTTC
AATTACAGAAAATACGTCTTGGAACAAAGAGTTCTCTGCCGAAGCCGTCAATGGTGTCTTCG
TGCTTTGTAAAAGTAGCAGTAAATCCTGCGCTACCAATGACTTAGCTCGTGCATCAAAGGAA
TATCTTCCAGCATCAACATTTAAGATCCCCAACGCAATTATCGGTCTAGAAACTGGTGTCAT
AAAGAATGAGCATCAGGTTTTCAAATGGGACGGAAAGCCAAGAGCCATGAAGCAATGGGAAA
GAGACTTGACCTTAAGAGGGGCAATACAAGTTTCAGCTGTTCCCGTATTTCAACAAATCGCC
AGAGAAGTTGGCGAAATAAGAATGCA**GAAATATCTTAAAAAATTTTCATATGGTAACCAGAA
TATCAGTGGTGGCATTGACAAATTCTGG**CTAGAAGGTCAGCTTAGAATCTCAGCATTCAATC
AAGTTAAATTTTTAGAGTCGCTCTACCTGAATAATTTGCCAGCATCAAAAGA**AAATCAGCTA
ATAGTAAAAGAGGCTTTGGTAACGGAGGCTGCGCCTGAATATCTTGTGCATTCAAAAACTGG
TTTTTCTGGTGTGGGAACTGAGTCAAATCCTGGTGTCGCATGGTGGGTTGGTTGGGTTGAGA
AGGGAGCAGAGGTTTACTTTTTCGCATTTAACATGGATATAGACAACGAAAATAAGTTGCCG
CTAAGAAAATCCATTCCCACCAAAATCATGGCAAGTGAGGGCATCATTGGTGGCTAA**

SEQ ID NO 44

MKTFAAYLVLACLSSTALAGSITENTSWNKEFSAEAVNGVFVLCKSSSKSCATNDLARASKE
YLPASTFKIPNAIIGLETGVIKNEHQVFKWDGKPRAMKQWERDLTLRGAIQVSAVPVFQQIA
REVGEIRMQKYLKKFSYGNQNISGGIDKFWLEGQLRISAFNQVKFLESLYLNNLPASKENQL
IVKEALVTEAAPEYLVHSKTGFSGVGTESNPGVAWWVGWVEKGAEVYFFAFNMDIDNENKLP
LRKSIPTKIMASEGIIGG.

SEQ ID NO 45

Fig. 8 (continued).

c) >OUL3-05-IV

ATGAAAACATTTGCCGCATATGTAATTATCGCGTGTCTTTCGAGTACGGCATTAGCTAGTTC
AATTACAGAAAATACGTCTTGGAACAAAGAGTTCTCTGCCGAAGCCGTCAATGGTGTCTTCG
TGCTTTGTAAAAGTAGCAGTAAATCCTGCGCTACCAATGACTTAGCTCGTGCATCAAAGGAA
TATCTTCCAGCATCAACATTTAAGATCCCCAACGCAATTATCGGCCTAGAAACTGGTGTCAT
AAAGAATGAGCATCAGGTTTTCAAATGGGACGGAAAGCCAAGAGCCATGAAGCAATGGGAAA
GAGACTTGACCTTAAGAGGGGCAATACAAGTTTCAGCTGTTCCCGTATTTCAACAAATCGCC
AGAGAAGTTGGCGAA<u>ATAAGAATGCA</u>GAAATATCTTAAAAAATTTTCATATGGTAACCAGAA
TATCAGTGGTGGCATTGACAAATTCTGGTTGGAGGGTCAGCTTAGAATTTCCGCAGTTAATC
AAGTGGAGTTTCTAGAGTCTCTATTTTTAAATAAATTGTCAGCATCAAAAGAAAATCAGCTA
ATAGTAAAAGAGGCTTTGGTAACGGAGGCTGCGCCTGAATATCTTGTGCATTCAAAAACTGG
TTTTTCTGGTGTGGGAACTGAGTCAAATCCTGGTGTCGCATGGTGGGTTGGTTGGGTTGAGA
AGGGAGCAGAGGTTTACTTTTTCGCATTTAACATGGATATAGACAACGAAAATAAGTTGCCG
CTAAGAAAATCCATTCCCACCAAAATCATGGCAAGTGAGGGCATCATTGGTGGCTAA

SEQ ID NO 46

MKTFAAYVIIACLSSTALASSITENTSWNKEFSAEAVNGVFVLCKSSSKSCATNDLARASKE
YLPASTFKIPNAIIGLETGVIKNEHQVFKWDGKPRAMKQWERDLTLRGAIQVSAVPVFQQIA
REVGEIRMQKYLKKFSYGNQNISGGIDKFWLEGQLRISAVNQVEFLESLFLNKLSASKENQL
IVKEALVTEAAPEYLVHSKTGFSGVGTESNPGVAWWVGWVEKGAEVYFFAFNMDIDNENKLP
LRKSIPTKIMASEGIIGG.

SEQ ID NO 47

Fig. 8 (continued).

d) >OUL3-05-IX

ATGAAAACATTAGCCGCATATTTAGTTCTAGTTTTTTATGCAAGCACCGCGCTCTCAGAGTC
AATTACAGAAAATTTGGCGTGGAATAAAGAATTTTCTAGTGAATCCGTACATGGCGTTTTTG
TACTTTGTAAAAGTAGTAGCAATTCCTGTACTACAAATAATGCGGCACGTGCATCTACAGCC
TATATTCCAGCATCAACATTCAAAATTCCTAATGCTCTAATAGGTCTTGAAACCGGCGCCAT
AAAAGATGAACGGCAGGTTTTCAAATGGGACGGAAAGCCAAGAGCCATGAAGCAATGGGAAA
GAGACTTAAAGCTAAGGGGCGCTATACAGGTTTCTGCTGTTCCGGTATTTCAACAAATTGCC
AGAGAAGTTGGCGAAATAAGAATGCAAAAATACCTTAACCTGTTTTCATACGGCAACGCCAA
TATAGGGGGAGGCATTGACAAATTCTGGCTAGAAGGTCAGCTTAGAATCTCAGCATTCAATC
AAGTTAAATTTTTAGAGTCGCTCTACCTGAATAAATTGTCAGCATCAAAAGAAAACCAACTA
ATAGTAAAAGAGGCAATAGTTACAGAAGCAACTCCAGAATATATAGTTCATTCAAAAACTGG
TTTTTCTGGTGTTGGCACAGAATCAAGTCCTGGTGTCGCTTGGTGGGTTGGTTGGGTAGAGA
AAGGAACTGAGGTTTACTTTTTTGCTTTTAACATGGACATAGACAATGAGAGTAAATTGCCG
TCAAGAAAATCCATTCCCACCAAAATCATGGCAAGTGAGGGCATCATTGGTGGCTAA

SEQ ID NO 48

MKTLAAYLVLVFYASTALSESITENLAWNKEFSSESVHGVFVLCKSSSNSCTTNNAARASTA
YIPASTFKIPNALIGLETGAIKDERQVFKWDGKPRAMKQWERDLKLRGAIQVSAVPVFQQIA
REVGEIRMQKYLNLFSYGNANIGGGIDKFWLEGQLRISAFNQVKFLESLYLNKLSASKENQL
IVKEAIVTEATPEYIVHSKTGFSGVGTESSPGVAWWVGWVEKGTEVYFFAFNMDIDNESKLP
SRKSIPTKIMASEGIIGG.

SEQ ID NO 49

Fig. 8 (continued).

e) >OUL3-05-X

ATGAAAACATTTGCCGCATATGTAATTATCGCGTGTCTTTCGAGTACGGCATTAGCTGGTTC
AATTACAGAAAATACGTCTTGGAACAAAGAGTTCTCTGCCGAAGCCGTCAATGGTGTCTTCG
TGCTTTGTAAAAGTAGCAGTAAATCCTGCGCTACCAATGACTTAGCTCGTGCATCAAAGGAA
TATCTTCCAGCATCAACATTTAAGATCCCCAACGCAATTATCGGCCTAGAAACTGGTGTCAT
AAAGAATGAGCATCAGGTTTTCAAATGGGACGGAAAGCCAAGAGCCATGAAGCAATGGGAAA
GAGACTTGACCTTAAGAGGGGCAATACAAGTTTCAGCTGTTCCCGTATTTCAACAAATCGCC
AGAGAAGTTGGCGAAGTAAGAATGCAGAAATATCTTAA**AAAATTTTCATATGGTAACCAGAA
TATCAGTGGTGGCATTGACAAATTCTGGTTGGAAGGTCAGCTTAGAATTTCCGCAGTTAATC
AAGTGGAGTTTCTAGAGTCTCTATTTTTAAATAAATTGTCAGCATCAAAAGAAAATCAGCTA
ATAGTAAAAGAGGCTTTGGTAACGGAGGCTGCGCCTGAATATCTTGTGCATTCAAAAACTGG
TTTTTCTGGTGTGGGAACTGAGTCAAATCCTGGTGTCGCATGGTGGGTTGGTTGGGTTGAGA
AGGGAGCAGAGGTTTACTTTTTCGCATTTAACATGGATATAGACAACGAAAATAAGTTGCCG
CTAAGAAAATCCATTCCCACCAAAATCATGGCAAGTGAGGGCATCATTGGTGGCTAA**

SEQ ID NO 50

MKTFAAYVIIACLSSTALAGSITENTSWNKEFSAEAVNGVFVLCKSSSKSCATNDLARASKE
YLPASTFKIPNAIIGLETGVIKNEHQVFKWDGKPRAMKQWERDLTLRGAIQVSAVPVFQQIA
REVGEVRMQKYLKKFSYGNQNISGGIDKFWLEGQLRISAVNQVEFLESLFLNKLSASKENQL
IVKEALVTEAAPEYLVHSKTGFSGVGTESNPGVAWWVGWVEKGAEVYFFAFNMDIDNENKLP
LRKSIPTKIMASEGIIGG.

SEQ ID NO 51

Fig. 9:

a) >ADH Kluyveromyces

ATGTCTGCTCACGAAATCCCAAAGACCCAGAAAGGTGTTATCTTCTACGAGACCG
GTGGTAAGCTGGAATACAAGGACATCGATGTCCCAACCCCAAAGGCCAACGAGC
TTTTGGTCAACGTCAAGTACTCCGGTGTGTGCCACACTGACTTGCACGCCTACCAC
GGTGACTGGCCATTGCCAGTTAAGTTGCCTCTAGTCGGTGGCCACGAGGGTGCCG
GTGTCGTTGTCGCCATGGGTGAGAACGTCAAGGGCTGGAAGGTCGGTGACTTGGC
CGGTATCAAGTGGTTGAACGGCTCCTGTATGTCCTGTGAGTCCTGTGAGTTGGGT
AACGAGTCCAACTGTCCAGAGGCTGACTTGTCCGGTTACACCCACGACGGTTCTT
TCCAGCAGTACGCTACTGCCGATGCCGTCCAGGCCGCTAAGATCCCAGCTGGCGC
TGACCTTGCTGAGATCGCCCCAATCCTGTGTGCCGGTATCACTGTCTACAAGGCTT
TGAAGTCTGCTAACTTGCAGGCCGGTGACTGGGTTGCCATCTCCGGTGCCGCCGG
TGGTTTGGGTTCCCTAGCCGTCCAGTACGCCAAGGCCATGGGTTACCGTGTCTTG
GGTATCGACGGTGGTGAGGAGAAGGAGCAGCTCTTCAGACAGTTGGGTGGTGAG
GTCTTCATCGACTTCAGAACCTGCAAGGACATCGAGGGTGAGATCATCAAGGCCA
CCAACGGTGGTGCTCACGGTGTCATCAACGTCTCTGTCTCCGAGGCCGCCATCGA
GTCCTCTACCAACTACGTCAGAGCCAACGGTACCGTCGTCTTGGTCGGTTTGCCA
GCTGGCGCCAAGTGCAAGTCTGACGTTTTCAACCAGGTCGTCAAGTCCATCTCTA
TCGTCGGTTCTTACGTCGGTAACAGAGCTGACACCAGAGAGGCTCTAGACTTCTT
CGTCCGTGGTTTGGTCAGATCTCCAATCAAGGTTGTCGGTCTATCTACTCTACCAG
AGATTTTCGAGAAGATGGAGAAGGGCCAAATTGTTGGCAGATACGTTGTCGACA
CCTCCAACTAA
SEQ ID NO 52 b) >ADH Saccharomyces

ATGTCTATCCCAGAAACTCAAAAAGGTGTTATCTTCTACGAATCCCACGGTAAGT
TGGAATACAAAGATATTCCAGTTCCAAAGCCAAAGGCCAACGAATTGTTGATCAA
CGTTAAATACTCTGGTGTCTGTCACACTGACTTGCACGCTTGGCACGGTGACTGG
CCATTGCCAGTTAAGCTACCATTAGTCGGTGGTCACGAAGGTGCCGGTGTCGTTG
TCGGCATGGGTGAAAACGTTAAGGGCTGGAAGATCGGTGACTACGCCGGTATCA
AATGGTTGAACGGTTCTTGTATGGCCTGTGAATACTGTGAATTGGGTAACGAATC
CAACTGTCCTCACGCTGACTTGTCTGGTTACACCCACGACGGTTCTTTCCAACAAT
ACGCTACCGCTGACGCTGTTCAAGCCGCTCACATTCCTCAAGGTACCGACTTGGC
CCAAGTCGCCCCCATCTTGTGTGCTGGTATCACCGTCTACAAGGCTTTGAAGTCTG
CTAACTTGATGGCCGGTCACTGGGTTGCTATCTCCGGTGCTGCTGGTGGTCTAGGT
TCTTTGGCTGTTCAATACGCCAAGGCTATGGGTTACAGAGTCTTGGGTATTGACG
GTGGTGAAGGTAAGGAAGAATTATTCAGATCCATCGGTGGTGAAGTCTTCATTGA
CTTCACTAAGGAAAAGGACATTGTCGGTGTGTTCTAAAGGCCACTGACGGTGGTG
CTCACGGTGTCATCAACGTTTCCGTTCCGAAGCCGCTATTGAAGCTTCTACCAGAT
ACGTTAGAGCTAACGGTACCACCGTTTGGTCGGTATGCCAGCTGGTGCCAAGTG
TTGTTCTGATGTCTTCAACCAAGTCGTCAAGTCCATCTCTATTGTTGGTTCTTACGT
CGGTAACAGAGCTGACACCAGAGAAGCTTTGGACTTCTTCGCCAGAGGTTTGGTC
AAGTCTCCAATCAAGGTTGTCGGCTTGTCTACCTTGCCAGAAATTTACGAAAAGA
TGGAAAAGGGTCAAATCGTTGGTAGATACGTTGTTGACACTTCTAAATAA
SEQ ID NO 53

Fig. 9 (continued)

c) >Clon A02

ATGTCTATCCCAGAAACTCAAAAAGGTGTTATCTTCTACGAATCCCACGGTAAGT
TGGAATACAAAGATATTCCAGTTCCAAAGCCAAAGGCCAACGAATTGTTGATCAA
CGTTAAATACTCTGGTGTCTGTCACACTGACTTGCACGCTTGGCACGGTGACTGG
CCATTGCCAGTTAAGCTACCATTAGTCGGTGGTCACGAAGGTGCCGGTGTCGTTG
TCGGCATGGGTGAAAACGTTAAGGGCTGGAAGATCGGTGACTACGCCGGTATCA
AATGGTTGAACGGTTCTTGTATGGCCTGTGAATACTGTGAATTGGGTAACGAATC
CAACTGTCCAGAGGCTGACTTGTCCGGTTACACCCACGACGGTTCTTTCCAGCAG
TACGCTACTGCCGATGCCGTCCAGGCCGCTAAGATCCCAGCTGGCGCTGACCTTG
CTGAGATCGCCCCAATCCTGTGTGCCGGTATCACTGTCTACAAGGCTTTGAAGTCT
GCTAACTTGCAGGCCGGTGACTGGGTTGCCATCTCCGGTGCCGCCGGTGGTTTGG
GTTCCCTAGCCGTCCAGTACGCCAAGGCCATGGGTTACCGTGTCTTGGGTATCGA
CGGTGGTGAGGAGAAGGAGCAGCTCTTCAGACAGTTGGGTGGTGAGGTCTTCATC
GACTTCAGAACCTGCAAGGACATCGAGGGTGAGATCATCAAGGCCACCAACGGT
GGCGCTCACGGTGTCATCAACGTCTCTGTCTCCGAGGCCGCCATCGAGTCCTCTA
CCAACTACGTCAGAGCCAACGGTACCGTCGTCTTGGTCGGTTTGCCAGCTGGCGC
CAAGTGCAAGTCTGACGTTTTCAACCAGGTCGTCAAGTCCATCTCTATCGTCGGTT
CTTACGTCGGTAACAGAGCTGACACCAGAGAGGCTCTAGACTTCTTCGTCCGTGG
TTTGGTCAGATCTCCAATCAAGGTTGTCGGTCTATCTACTCTACCAGAGATTTTCG
AGAAGATGGAGAAGGGCCAAATTGTTGGCAGATACGTTGTCGACACCTCCAACT
AA
SEQ ID NO 54 d) >Clon A03

GCCATGGGTGAGAATGTCTATCCCAGAAACTCAAAAAGGTGTTATCTTCTACGAA
TCCCACGGTAAGTTGGAATACAAAGATATTCCAGTTCCAAAGCCAAAGGCCAAC
GAATTGTTGATCAACGTTAAATACTCTGGTGTCTGTCACACTGACTTGCACGCTTG
GCACGGTGACTGGCCATTGCCAGTTAAGCTACCATTAGTCGGTGGTCACGAAGGT
GCCGGTGTCGTTGTCGCCATGGGTGAGAACGTCAAGGGCTGGAAGGTCGGTGACT
TGGCCGGTATCAAGTGGTTGAACGGCTCCTGTATGTCCTGTGAGTCCTGTGAGTT
GGGTAACGAGTCCAACTGTCCAGAGGCTGACTTGTCCGGTTACACCCACGACGGT
TCTTTCCAGCAGTACGCTACTGCCGATGCCGTCCAGGCCGCTAAGATCCCAGCTG
GCGCTGACCTTGCTGAGATCGCCCCAATCCTGTGTGCCGGTATCACTGTCTACAA
GGCTTTGAAGTCTGCTAACTTGCAGGCCGGTGACTGGGTTGCCATCTCCGGTGCC
GCCGGTGGTTTGGGTTCCCTAGCCGTCCAGTACGCCAAGGCCATGGGTTACCGTG
TCTTGGGTATCGACGGTGGTGAGGAGAAGGAGCAGCTCTTCAGACAGTTGGGTG
GTGAGGTCTTCATCGACTTCAGAACCTGCAAGGACATCGAGGGTGAGATCATCAA
GGCCACCAACGGTGGTGCTCACGGTGTCATCAACGTCTCTGTCTCCGAGGCCGCC
ATCGAGTCCTCTACCAACTACGTCAGAGCCAACGGTACCGTCGTCTTGGTCGGTT
TGCCAGCTGGCGCCAAGTGCAAGTCTGACGTTTTCAACCAGGTCGTCAAGTCCAT
CTCTATCGTCGGTTCTTACGTCGGTAACAGAGCTGACACCAGAGAGGCTCTAGAC
TTCTTCGTCCGTGGTTTGGTCAGATCTCCAATCAAGGTTGTCGGTCTATCTACTCT
ACCAGAGATTTTCGAGAAGATGGAGAAGGGCCAAATTGTTGGCAGATACGTTGT
CGACACCTCCAACTAA
SEQ ID NO 55

Fig. 9 (continued)

e) >Clon A05

ATGTCTATCCCAAAGACCCAGAAAGGTGTTATCTTCTACGAGACCGGTGGTAAGC
TGGAATACAAGGACATCGATGTCCCAACCCCAAAGGCCAACGAGCTTTTGGTCAA
CGTCAAGTACTCCGGTGTGTGCCACACTGACTTGCACGCCTACCACGGTGACTGG
CCATTGCCAGTTAAGTTGCCTCTAGTCGGTGGCCACGAGGGTGCCGGTGTCGTTG
TCGCCATGGGTGAGAACGTCAAGGGCTGGAAGGTCGGTGACTTGGCCGGTATCA
AGTGGTTGAACGGCTCCTGTATGTCCTGTGAGTCCTGTGAGTTGGGTAACGAGTC
CAACTGTCCAGAGGCTGACTTGTCCGGTTACACCCACGACGGTTCTTTCCAGCAG
TACGCTACTGCCGATGCCGTCCAGGCCGCTAAGATCCCAGCTGGCGCTGACCTTG
CTGAGATCGCCCCAATCCTGTGTGCCGGTATCACTGTCTACAAGGCTTTGAAGTCT
GCTAACTTGCAGGCCGGTGACTGGGTTGCCATCTCCGGTGCCGCCGGTGGTTTGG
GTTCCCTAGCCGTCCAGTACGCCAAGGCCATGGGTTACCGTGTCTTGGGTATCGA
CGGTGGTGAGGAGAAGGAGCAGCTCTTCAGACAGTTGGGTGGTGAGGTCTTCATC
GACTTCAGAACCTGCAAGGACATCGAGGGTGAGATCATCAAGGCCACCAACGGT
GGTGCTCACGGTGTCATCAACGTCTCTGTCTCCGAGGCCGCCATCGAGTCCTCTAC
CAACTACGTCAGAGCCAACGGTACCGTCGTCTTGGTCGGTTTGCCAGCTGGCGCC
AAGTGCAAGTCTGACGTTTTCAACCAGGTCGTCAAGTCCATCTCTATCGTCGGTTC
TTACGTCGGTAACAGAGCTGACACCAGAGAGGCTCTAGACTTCTTCGTCCGTGGT
TTGGTCAGATCTCCAATCAAGGTTGTCGGTCTATCTACTCTACCAGAGATTTTCGA
GAAGATGGAGAAGGGCCAAATTGTTGGCAGATACGTTGTCGACACCTCCAACTA
A
SEQ ID NO 56 f) >Clon A06

ATGTCTATCCCAGAAACTCAAAAAGGTGTTATCTTCTACGAATCCCACGGTAAGT
TGGAATACAAAGATATTCCAGTTCCAAAGCCAAAGGCCAACGAATTGTTGATCAA
CGTTAAATACTCTGGTGTCTGTCACACTGACTTGCACGCTTGGCACGGTGACTGG
CCATTGCCAGTTAAGCTACCATTAGTCGGTGGTCACGAAGGTGCCGGTGTCGTTG
TCGGCATGGGTGAAAACGTTAAGGGCTGGAAGATCGGTGACTACGCCGGTATCA
AATGGTTGAACGGTTCTTGTATGGCCTGTGAATACTGTGAATTGGGTAACGAGTC
CAACTGTCCAGAGGCTGACTTGTCTGGTTACACCCACGACGGTTCTTTCCAACAA
TACGCTACTGCCGATGCCGTCCAGGCCGCTAAGATCCCAGCTGGCGCTGACCTTG
CTGAGATCGCCCCAATCCTGTGTGCCGGTATCACTGTCTACAAGGCTTTGAAGTCT
GCTAACTTGCAGGCCGGTGACTGGGTTGCCATCTCCGGTGCCGCCGGTGGTTTGG
GTTCCCTAGCCGTCCAGTACGCCAAGGCCATGGGTTACCGTGTCTTGGGTATCGA
CGGTGGTGAGGAGAAGGAGCAGCTCTTCAGACAGTTGGGTGGTGAGGTCTTCATC
GACTTCAGAACCTGCAAGGACATCGAGGGTGAGATCATCAAGGCCACCAACGGT
GGTGCTCACGGTGTCATCAACGTCTCTGTCTCCGAGGCCGCCATCGAGTCCTCTAC
CAACTACGTCAGAGCCAACGGTACCGTCGTCTTGGTCGGTTTGCCAGCCGGCGCC
AAGTGCAAGTCTGACGTTTTCAACCAGGTCGTCAAGTCCATCTCTATCGTCGGTTC
TTACGTCGGTAACAGAGCTGACACCAGAGAGGCTCTAGACTTCTTCGTCCGTGGT
TTGGTCAGATCTCCAATCAAGGTTGTCGGTCTATCTACTCTACCAGAGATTTTCGA
GAAGATGGAGAAGGGCCAAATTGTTGGCAGATACGTTGTCGACACCTCCAACTA
A
SEQ ID NO 57

Fig. 9 (continued)

g) >Clon A10

ATGTCTATCCCAGAAACTCAAAAAGGTGTTATCTTCTACGA<u>GACCGGTGGTAAGC
TGGAATACAAGGACATCGATGTCCCAACCCCAAAGGCCAACGAGCTTTTGGTCAA
CGTCAAGTACTCCGGTGTGTGCCACACTGACTTGCACGCCTACCACGGTGACTGG
CCATTGCCAGTTAAGTTGCCTCTAGTCGGTGGCCACGAGGGTGCCGGTGTCGTTG
TCGCCATGGGTGAGAACGTCAAGGGCTGGAAGGTCGGTGACTTGGCCGGTATCA
AGTGGTTGAACGGCTCCTGTATGTCCTGTGAGTCCTGTGAGTTGGGTAACGAGTC
CAACTGTCCAGAGGCTGACTTGTCCGGTTACACCCACGACGGTTCTTTCCAGCAG
TACGCTACTGCCGATGCCGTCCAGGCCGCTAAGATCCCAGCTGGCGCTGACCTTG
CTGAGATCGCCCCAATCCTGTGTGCCGGTATCACTGTCTACAAGGCTTTGAAGTCT
GCTAACTTGCAGGCCGGTGACTGGGTTGCCATCTCCGGTGCCGCCGGTGGTTTGG
GTTCCCTAGCCGTCCAGTACGCCAAGGCCATGGGTTTACCGTGTCTTGGGTATCG
ACGGTGGTGAGGAGAAGGAGCAGCTCTTCAGACAGTTGGGTGGTGGAGGTCTTC
ATCGACTTCAGAACCTGCAAGGACATCGAGGGTGAGATCATCAAGCCCACCAAC
GGTGGTGCTCACGGTGTCATCAACGTCTCTGTCTCCGAGGCCGCCATCGAGTCCT
CTACCAACTACGTCAGAGCCAACGGTACCGTCGTCTTGGTCGGTTTGCCAGCTGG
CGCCAAGTGCAAGTCTGACGTTTTCAACCAGGTCGTCAAGTCCATCTCTATCGTC
GGTTCTTACGTCGGTAACAGAGCTGACACCAGAGAGGCTCTAGACTTCTTCGTCC
GTGGTTTGGTCAGATCTCCAATCAAGGTTGTCGGTCTATCTACTCTACCAGAGATT
TTCGAGAAGATGGAGAAGGGCCAAATTGTTGGCAGATACGTTGTCGACACCTCCA
ACTAA</u>
SEQ ID NO 58 h) >Clon A11

ATGTCTATCCCAGAAACTCAAAAAGGTGTTATCTTCTACGAATCCCACGGTAAGT
TGGAATACAAAGATATTCCAGTTCCAAAGCCAAAGGCCAACGAATTGTTGATCAA
CGTTAAATACTCTGGTGTCTGTCACACTGACTTGCACGCTTGGCACGGTGACTGG
CCATTGCCAGTTAAGCTACCATTAGTCGGTGGTCACGAAGGTGCCGGTGTCGTTG
TCGGCATGGGTGAAAACGTTAAGGGCTGGAAGATCGGTGACTACGCCGGTATCA
AATGGTTGAACGGTTCTTGTATGGCCTGTGAATACTGTGAATTGGGTAACGAATC
CAACTGTCCTCACGCTGACTTGTCTGGTTACACCCACGACGGTTCTTTCCA<u>GCAGT
ACGCTACTGCCGATGCCGTCCAGGCCGCTAAGATCCCAGCTGGCGCTGACCTTGC
TGAGATCGCCCCAATCCTGTGTGCCGGTATCACTGTCTACAAGGCTTTGAAGTCT
GCTAACTTGCAGGCCGGTGACTGGGTTGCCATCTCCGGTGCCGCCGGTGGTTTGG
GTTCCCTAGCCGTCCAGTACGCCAAGGCCATGGGTTACCGTGTCTTGGGTATCGA
CGGTGGTGAGGAGAAGGAGCAGCTCTTCAGACAGTTGGGTGGTGAGGTCTTCATC
GACTTCAGAACCTGCAAGGACATCGAGGGTGAGATCATCAAGGCCACCAACGGT
GGTGCTCACGGTGTCATCAACGTCTCTGTCTCCGAGGCCGCCATCGAGTCCTCTAC
CAACTACGTCAGAGCCAACGGTACCGTCGTCTTGGTCGGTTTGCCAGCTGGCGCC
AAGTGCAAGTCTGACGTTTTCAACCAGGTCGTCATGTCCATCTCTATCGTCGGTTC
TTACGTCGGTAACAGAGCTGACACCAGAGAGGCTCTAGACTTCTTCGTCCGTGGT
TTGGTCAGATCTCCAATCAAGGTTGTCGGTCTATCTACTCTACCAGAGATTTTCGA
GAAGATGGAGAAGGGCCAAATTGTTGGCAGATACGTTGTCGACACCTCCAACTA
A</u>
SEQ ID NO 59

SEQUENCE LISTING

```
<160> NUMBER OF SEQ ID NOS: 59

<210> SEQ ID NO 1
<211> LENGTH: 801
<212> TYPE: DNA
<213> ORGANISM: Artificial Sequence
<220> FEATURE:
<223> OTHER INFORMATION: gene hybrid OXA11/OXA7

<400> SEQUENCE: 1
atgaaaacat ttgccgcata tgtaattatc gcgtgtcttt cgagtacggc attagctagt      60
tcaattacag aaaatacgtt ttggaacaaa gagttctctg ccgaagccgt caatggtgtt     120
ttcgtgcttt gtaaaagtag cagtaaatcc tgcgctacca ataacttagc tcgtgcatca     180
aaggaatatc ttccagcatc aacatttaag atccccaacg caattatcgg cctagaaact     240
ggtgtcataa agaatgagca tcagattttc aaatgggacg gaaaaccaag agccatgaaa     300
caatgggaaa gagacttgag cttaagaggg gcaatacaag tttcagcggt tcccgtattt     360
```

```
caacaaatcg ccagagaagt tggcgaagta agaatgcaga aatatcttaa aaaattttca    420
tatggtaacc agaatatcag tggcggcatt gacaaattct ggttggaggg tcagcttaga    480
atttccgcag ttaatcaagt ggagtttcta gagtctctat ttttaaataa attgtcagca    540
tcaaaagaaa atcagctaat agtaaaagag ctttggtaa cggaggctgc gcctgaatat     600
cttgtgcatt caaaaactgg ttttctggt gtgggaactg agtcaaatcc tggtgtcgca     660
tggtgggttg gttggttga aagggagca gaggtttact ttttcgcatt taacatggat      720
atagacaacg aaaataagtt gccgctaaga aaatccattc ccaccaaaat catggcaagt    780
gagggcatca ttggtggcta a                                              801
```

<210> SEQ ID NO 2
<211> LENGTH: 266
<212> TYPE: PRT
<213> ORGANISM: Artificial Sequence
<220> FEATURE:
<223> OTHER INFORMATION: protein hybrid OXA11/OXA7

<400> SEQUENCE: 2

```
Met Lys Thr Phe Ala Ala Tyr Val Ile Ile Ala Cys Leu Ser Ser Thr
1               5                   10                  15

Ala Leu Ala Ser Ser Ile Thr Glu Asn Thr Phe Trp Asn Lys Glu Phe
                20                  25                  30

Ser Ala Glu Ala Val Asn Gly Val Phe Val Leu Cys Lys Ser Ser Ser
            35                  40                  45

Lys Ser Cys Ala Thr Asn Asn Leu Ala Arg Ala Ser Lys Glu Tyr Leu
        50                  55                  60

Pro Ala Ser Thr Phe Lys Ile Pro Asn Ala Ile Ile Gly Leu Glu Thr
65                  70                  75                  80

Gly Val Ile Lys Asn Glu His Gln Ile Phe Lys Trp Asp Gly Lys Pro
                85                  90                  95

Arg Ala Met Lys Gln Trp Glu Arg Asp Leu Ser Leu Arg Gly Ala Ile
            100                 105                 110

Gln Val Ser Ala Val Pro Val Phe Gln Gln Ile Ala Arg Glu Val Gly
        115                 120                 125

Glu Val Arg Met Gln Lys Tyr Leu Lys Lys Phe Ser Tyr Gly Asn Gln
    130                 135                 140

Asn Ile Ser Gly Gly Ile Asp Lys Phe Trp Leu Glu Gly Gln Leu Arg
145                 150                 155                 160

Ile Ser Ala Val Asn Gln Val Glu Phe Leu Glu Ser Leu Phe Leu Asn
                165                 170                 175

Lys Leu Ser Ala Ser Lys Glu Asn Gln Leu Ile Val Lys Glu Ala Leu
            180                 185                 190

Val Thr Glu Ala Ala Pro Glu Tyr Leu Val His Ser Lys Thr Gly Phe
        195                 200                 205

Ser Gly Val Gly Thr Glu Ser Asn Pro Gly Val Ala Trp Trp Val Gly
    210                 215                 220

Trp Val Glu Lys Gly Ala Glu Val Tyr Phe Phe Ala Phe Asn Met Asp
225                 230                 235                 240

Ile Asp Asn Glu Asn Lys Leu Pro Leu Arg Lys Ser Ile Pro Thr Lys
                245                 250                 255

Ile Met Ala Ser Glu Gly Ile Ile Gly Gly
            260                 265
```

<210> SEQ ID NO 3

```
<211> LENGTH: 801
<212> TYPE: DNA
<213> ORGANISM: Artificial Sequence
<220> FEATURE:
<223> OTHER INFORMATION: gene hybrid OXO11/OXO7

<400> SEQUENCE: 3
atgaaaacat tgccgcata tgtaattatc gcgtgtcttt cgagtacggc attagctggt      60
tcaattacag aaatacgtc ttggaacaaa gagttctctg ccgaagccgt caatggtgtc     120
ttcgtgcttt gtaaaagtag cagtaaatcc tgcgctacca atgacttagc tcgtgcatca    180
aaggaatatc ttccagcatc aacatttaag atccccaacg caattatcgg cctagaaact    240
ggtgtcataa agaatgagca tcagattttc aaatgggacg gaaagccaag agccatgaaa    300
caatgggaaa gagacttgac cttaagaggg gcaatacaag tttcagcggt tcccgtattt    360
caacaaatcg ccagagaagt tggcgaagta agaatgcaga aatatcttaa aaaattttca    420
tatggtaacc agaatatcag tggtggcatt gacaaattct ggtcggaggg tcagcttaga    480
atttccgcag ttaatcaagt ggagtttcta gagtctctat ttttaaataa attgtcagca    540
tcaaaagaaa atcagctaat agtaaaagag ctttggtaa cggaggctgc gcctgaatat    600
cttgtgcatt caaaaactgg ttttttctggt gtgggaactg agtcaaatcc tggtgtcgca    660
tggtgggttg gttgggttga aagggagca gaggtttact ttttcgcatt taacatggat    720
atagacaacg aaataagtt gccgctaaga aatccattc ccaccaaaat catggcaagt    780
gagggcatca ttggtggcta a                                              801

<210> SEQ ID NO 4
<211> LENGTH: 266
<212> TYPE: PRT
<213> ORGANISM: Artificial Sequence
<220> FEATURE:
<223> OTHER INFORMATION: protein hybrid OXA11/OXA7

<400> SEQUENCE: 4

Met Lys Thr Phe Ala Ala Tyr Val Ile Ile Ala Cys Leu Ser Ser Thr
1               5                   10                  15

Ala Leu Ala Gly Ser Ile Thr Glu Asn Thr Ser Trp Asn Lys Glu Phe
            20                  25                  30

Ser Ala Glu Ala Val Asn Gly Val Phe Val Leu Cys Lys Ser Ser
        35                  40                  45

Lys Ser Cys Ala Thr Asn Asp Leu Ala Arg Ala Ser Lys Glu Tyr Leu
    50                  55                  60

Pro Ala Ser Thr Phe Lys Ile Pro Asn Ala Ile Ile Gly Leu Glu Thr
65                  70                  75                  80

Gly Val Ile Lys Asn Glu His Gln Ile Phe Lys Trp Asp Gly Lys Pro
                85                  90                  95

Arg Ala Met Lys Gln Trp Glu Arg Asp Leu Thr Leu Arg Gly Ala Ile
            100                 105                 110

Gln Val Ser Ala Val Pro Val Phe Gln Gln Ile Ala Arg Glu Val Gly
        115                 120                 125

Glu Val Arg Met Gln Lys Tyr Leu Lys Lys Phe Ser Tyr Gly Asn Gln
    130                 135                 140

Asn Ile Ser Gly Gly Ile Asp Lys Phe Trp Ser Glu Gly Gln Leu Arg
145                 150                 155                 160

Ile Ser Ala Val Asn Gln Val Glu Phe Leu Glu Ser Leu Phe Leu Asn
                165                 170                 175
```

Lys Leu Ser Ala Ser Lys Glu Asn Gln Leu Ile Val Lys Glu Ala Leu
            180                 185                 190

Val Thr Glu Ala Ala Pro Glu Tyr Leu Val His Ser Lys Thr Gly Phe
        195                 200                 205

Ser Gly Val Gly Thr Glu Ser Asn Pro Gly Val Ala Trp Trp Val Gly
    210                 215                 220

Trp Val Glu Lys Gly Ala Glu Val Tyr Phe Phe Ala Phe Asn Met Asp
225                 230                 235                 240

Ile Asp Asn Glu Asn Lys Leu Pro Leu Arg Lys Ser Ile Pro Thr Lys
            245                 250                 255

Ile Met Ala Ser Glu Gly Ile Ile Gly Gly
            260                 265

<210> SEQ ID NO 5
<211> LENGTH: 801
<212> TYPE: DNA
<213> ORGANISM: Artificial Sequence
<220> FEATURE:
<223> OTHER INFORMATION: gene hybrid OXA11/OXA7

<400> SEQUENCE: 5
atgaaaacat tgccgcata tgtaattatc gcgtgtcttt cgagtacggc attagctggt        60
tcaattacag aaaatacgtc ttggaacaaa gagttctctg ccgaagccgt caatggtgtc       120
ttcgtgcttt gtaaaagtag cagtaaatcc tgcgctacca atgacttagc tcgtgcatca       180
aaggaatatc ttccagcatc aacatttaag atccccaacg caattatcgg cctagaaact       240
ggtgtcataa agaatgagca tcaggttttc aaatgggacg aaagccaag agccatgaag        300 caatgggaaa gagacttgac cttaagaggg gcaatacaag tttcagctgt tcccgtattt       360
caacaaatcg ccagagaagt tggcgaagta agaatgcaga ataccttaa aaattttcc         420 tatggcagcc agaatatcag tggtggcatt gacaaattct ggttggaaga ccagcttaga       480
atttccgcag ttaatcaagt ggagtttcta gagtctctat atttaaataa attgtcagca       540
tctaaagaaa accagctaat agtaaaagag ctttggtaa cggaggcggc acctgaatat       600
ctagtgcatt caaaaactgg ttttctggt gtgggaactg agtcaaatcc tggtgtcgca       660
tggtgggttg ggtgggttga aggagaca gaggtttact ttttcgcctt taacatggat        720
atagacaacg aaagtaagtt gccgctaaga aaatccattc ccaccaaaat cagggaaagt       780
gagggcatca ttggtggcta a                                                 801

<210> SEQ ID NO 6
<211> LENGTH: 266
<212> TYPE: PRT
<213> ORGANISM: Artificial Sequence
<220> FEATURE:
<223> OTHER INFORMATION: protein hybrid OXA11/OXA7

<400> SEQUENCE: 6

Met Lys Thr Phe Ala Ala Tyr Val Ile Ile Ala Cys Leu Ser Ser Thr
1               5                   10                  15

Ala Leu Ala Gly Ser Ile Thr Glu Asn Thr Ser Trp Asn Lys Glu Phe
            20                  25                  30

Ser Ala Glu Ala Val Asn Gly Val Phe Val Leu Cys Lys Ser Ser Ser
        35                  40                  45

Lys Ser Cys Ala Thr Asn Asp Leu Ala Arg Ala Ser Lys Glu Tyr Leu
    50                  55                  60

Pro Ala Ser Thr Phe Lys Ile Pro Asn Ala Ile Ile Gly Leu Glu Thr

```
                65                  70                  75                  80
Gly Val Ile Lys Asn Glu His Gln Val Phe Lys Trp Asp Gly Lys Pro
                    85                  90                  95

Arg Ala Met Lys Gln Trp Glu Arg Asp Leu Thr Leu Arg Gly Ala Ile
                    100                 105                 110

Gln Val Ser Ala Val Pro Val Phe Gln Gln Ile Ala Arg Glu Val Gly
                    115                 120                 125

Glu Val Arg Met Gln Lys Tyr Leu Lys Lys Phe Ser Tyr Gly Ser Gln
                130                 135                 140

Asn Ile Ser Gly Gly Ile Asp Lys Phe Trp Leu Glu Asp Gln Leu Arg
145                 150                 155                 160

Ile Ser Ala Val Asn Gln Val Glu Phe Leu Glu Ser Leu Tyr Leu Asn
                    165                 170                 175

Lys Leu Ser Ala Ser Lys Glu Asn Gln Leu Ile Val Lys Glu Ala Leu
                    180                 185                 190

Val Thr Glu Ala Ala Pro Glu Tyr Leu Val His Ser Lys Thr Gly Phe
                    195                 200                 205

Ser Gly Val Gly Thr Glu Ser Asn Pro Gly Val Ala Trp Trp Val Gly
                210                 215                 220

Trp Val Glu Lys Glu Thr Glu Val Tyr Phe Phe Ala Phe Asn Met Asp
225                 230                 235                 240

Ile Asp Asn Glu Ser Lys Leu Pro Leu Arg Lys Ser Ile Pro Thr Lys
                    245                 250                 255

Ile Arg Glu Ser Glu Gly Ile Ile Gly Gly
                    260                 265

<210> SEQ ID NO 7
<211> LENGTH: 801
<212> TYPE: DNA
<213> ORGANISM: Artificial Sequence
<220> FEATURE:
<223> OTHER INFORMATION: gene hybrid OXA11/OXA7

<400> SEQUENCE: 7
atgaaaacat tgccgcata tgtaattatc gcgtgtcttt cgagtacggc attagctggt        60
tcaattacag aaaatacgtc ttggaacaaa gagttctctg ccgaagccgt caatggtgtc      120
ttcgtgcttt gtaaaagtag cagtaaatcc tgcgctacca atgacttagc tcgtgcacca      180
aaggaatatc ttccagcatc aacatttaag atccccaacg caattatcgg cctagaaact      240
ggtgtcataa agaatgagca tcaggttttc aaatgggacg gaaagccaag agccatgaag      300
caatgggaaa gagacttgac cttaagaggg gcaatacaag tttcagctgt tcccgtattt      360
caacaaatcg ccagagaagt tggcgaagta agaatgcaga ataccttaa aaaatttttcc      420 tatggcagcc agaatatcag tggtggcatt gacaaattct ggttggaagg tcagcttaga      480
atttccgcag ttaatcaagt ggagtttcta gagtctctat ttttaaataa attgtcagca      540
tcaaaagaaa atcagctaat agtaaaagag ctttggtaa cggaggctgc gcctgaatat      600
cttgtgcatt caaaaactgg ttttttctggt gtgggaactg agtcaaatcc tggtgtcgca      660
tggtgggttg gttgggttga aaggggagca gaggtttact ttttcgcatt taacatggat      720
atagacaacg aaaataagtt gccgctaaga aaatccattc ccaccaaaat catggcaagt      780
gagggcatca ttggtggcta a                                                801

<210> SEQ ID NO 8
<211> LENGTH: 266
```

<212> TYPE: PRT
<213> ORGANISM: Artificial Sequence
<220> FEATURE:
<223> OTHER INFORMATION: protein hybrid OXA11/OXA7

<400> SEQUENCE: 8

```
Met Lys Thr Phe Ala Ala Tyr Val Ile Ile Ala Cys Leu Ser Ser Thr
1               5                   10                  15

Ala Leu Ala Gly Ser Ile Thr Glu Asn Thr Ser Trp Asn Lys Glu Phe
            20                  25                  30

Ser Ala Glu Ala Val Asn Gly Val Phe Val Leu Cys Lys Ser Ser Ser
        35                  40                  45

Lys Ser Cys Ala Thr Asn Asp Leu Ala Arg Ala Pro Lys Glu Tyr Leu
50                  55                  60

Pro Ala Ser Thr Phe Lys Ile Pro Asn Ala Ile Ile Gly Leu Glu Thr
65                  70                  75                  80

Gly Val Ile Lys Asn Glu His Gln Val Phe Lys Trp Asp Gly Lys Pro
                85                  90                  95

Arg Ala Met Lys Gln Trp Glu Arg Asp Leu Thr Leu Arg Gly Ala Ile
            100                 105                 110

Gln Val Ser Ala Val Pro Val Phe Gln Gln Ile Ala Arg Glu Val Gly
        115                 120                 125

Glu Val Arg Met Gln Lys Tyr Leu Lys Lys Phe Ser Tyr Gly Ser Gln
130                 135                 140

Asn Ile Ser Gly Gly Ile Asp Lys Phe Trp Leu Glu Gly Gln Leu Arg
145                 150                 155                 160

Ile Ser Ala Val Asn Gln Val Glu Phe Leu Glu Ser Leu Phe Leu Asn
                165                 170                 175

Lys Leu Ser Ala Ser Lys Glu Asn Gln Leu Ile Val Lys Glu Ala Leu
            180                 185                 190

Val Thr Glu Ala Ala Pro Glu Tyr Leu Val His Ser Lys Thr Gly Phe
        195                 200                 205

Ser Gly Val Gly Thr Glu Ser Asn Pro Gly Val Ala Trp Trp Val Gly
210                 215                 220

Trp Val Glu Lys Gly Ala Glu Val Tyr Phe Phe Ala Phe Asn Met Asp
225                 230                 235                 240

Ile Asp Asn Glu Asn Lys Leu Pro Leu Arg Lys Ser Ile Pro Thr Lys
                245                 250                 255

Ile Met Ala Ser Glu Gly Ile Ile Gly Gly
            260                 265
```

<210> SEQ ID NO 9
<211> LENGTH: 801
<212> TYPE: DNA
<213> ORGANISM: Artificial Sequence
<220> FEATURE:
<223> OTHER INFORMATION: gene hybrid OXA11/OXA7

<400> SEQUENCE: 9

```
atgaaaacat tgccgcata tgtaattatc gcgtgtcttt cgagtacggc attagctggt      60
tcaattacag aaaatacgtc ttggaacaaa gagttctctg ccgaagccgt caatggtgtc    120
ttcgtgcttt gtaaaagtag cagtaaatcc tgcgctacca atgacttagc tcgtgcatca    180
aaggaatatc ttccagcatc aacatttaag atccccaacg caattatcgg cctagaaact    240
ggtgtcataa agaatgagca tcaggttttc aaatgggacg gaaagccaag agccatgaag    300
caatgggaaa gagacttgac cttaagaggg gcaatacaag tttcagctgt tccgtatttt    360
```

```
caacaaatcg ccagagaagt tggcgaagta agaatgcaga aataccttaa aaaattttcc      420
tatggcagcc agaatatcag tggtggcatt gacaaattct ggttggaaga ccagcttaga      480
atttccgcag ttaatcaagt ggagtttcta gagtctctat atttaaataa attgtcagca      540
tctaaagaaa accagctaat agtaaaagag gctttggtaa cggaggcggc acctgaatat      600
ctagtgcatt caaaaactgg tttttctggt gtgggaactg agtcaaatcc tggtgtcgca      660
tggtgggttg ggtgggttga gaaggagaca gaggtttact ttttcgcctt taacatggat      720
atggacaacg aaagtaagtt gccgctaaga aaatccattc ccaccaaaat catggaaagt      780
gagggcatca ttggtggcta a                                                801
```

<210> SEQ ID NO 10
<211> LENGTH: 266
<212> TYPE: PRT
<213> ORGANISM: Artificial Sequence
<220> FEATURE:
<223> OTHER INFORMATION: protein hybrid OXA11/OXA7

<400> SEQUENCE: 10

```
Met Lys Thr Phe Ala Ala Tyr Val Ile Ile Ala Cys Leu Ser Ser Thr
1               5                   10                  15

Ala Leu Ala Gly Ser Ile Thr Glu Asn Thr Ser Trp Asn Lys Glu Phe
            20                  25                  30

Ser Ala Glu Ala Val Asn Gly Val Phe Val Leu Cys Lys Ser Ser Ser
        35                  40                  45

Lys Ser Cys Ala Thr Asn Asp Leu Ala Arg Ala Ser Lys Glu Tyr Leu
    50                  55                  60

Pro Ala Ser Thr Phe Lys Ile Pro Asn Ala Ile Ile Gly Leu Glu Thr
65                  70                  75                  80

Gly Val Ile Lys Asn Glu His Gln Val Phe Lys Trp Asp Gly Lys Pro
                85                  90                  95

Arg Ala Met Lys Gln Trp Glu Arg Asp Leu Thr Leu Arg Gly Ala Ile
            100                 105                 110

Gln Val Ser Ala Val Pro Val Phe Gln Gln Ile Ala Arg Glu Val Gly
        115                 120                 125

Glu Val Arg Met Gln Lys Tyr Leu Lys Lys Phe Ser Tyr Gly Ser Gln
    130                 135                 140

Asn Ile Ser Gly Gly Ile Asp Lys Phe Trp Leu Glu Asp Gln Leu Arg
145                 150                 155                 160

Ile Ser Ala Val Asn Gln Val Glu Phe Leu Glu Ser Leu Tyr Leu Asn
                165                 170                 175

Lys Leu Ser Ala Ser Lys Glu Asn Gln Leu Ile Val Lys Glu Ala Leu
            180                 185                 190

Val Thr Glu Ala Ala Pro Glu Tyr Leu Val His Ser Lys Thr Gly Phe
        195                 200                 205

Ser Gly Val Gly Thr Glu Ser Asn Pro Gly Val Ala Trp Trp Val Gly
    210                 215                 220

Trp Val Glu Lys Glu Thr Glu Val Tyr Phe Phe Ala Phe Asn Met Asp
225                 230                 235                 240

Met Asp Asn Glu Ser Lys Leu Pro Leu Arg Lys Ser Ile Pro Thr Lys
                245                 250                 255

Ile Met Glu Ser Glu Gly Ile Ile Gly Gly
            260                 265
```

<210> SEQ ID NO 11
<211> LENGTH: 801
<212> TYPE: DNA
<213> ORGANISM: Artificial Sequence
<220> FEATURE:
<223> OTHER INFORMATION: gene hybrid OXA11/OXA7

<400> SEQUENCE: 11

```
atgaaaacat tgccgcata tgtaattact gcgtgtcttt caagtacggc attagctagt      60
tcaattacag aaaatacgtt ttggaacaaa gagttctctg ccgaagccgt caatggtgtt    120
ttcgtgcttt gtaaaagtag cagtaaatcc tgcgctacct ataacttagc tcgtgcatca    180
aaggaatatc ttccagcatc aacatttaag atccccaacg caattatcgg cctagaaact    240
ggtgtcataa agaatgagca tcagattttc aaatgggacg gaaagccaag agccatgaaa    300
caatgggaaa gagacttgag cttaagaggg gcaatacaag tttcagcggt tcccgtattt    360
caacaaatcg ccagagaagt tggcgaagta agaatgcaga aatatcttaa aaaattttca    420
tatggtaacc agaatatcag tggtggcatt gacaaattct ggttgagggg tcagcttaga    480
atttccgcag ttaatcaagt ggagtttcta gagtctctat ttttaaataa attgtcagca    540
tcaaaagaaa atcagctaat agtaaaagag gctttggtaa cggaggctgc gcctgaatat    600
cttgtgcatt caaaaactgg ttttttctgg tgtgggaactg agtcaaatcc tggtgtcgca    660
tggtgggttg gttgggttga aagggagca gaggtttact ttttcgcatt taacatggat    720
atagacaacg aaaataagtt gccgctaaga aaatccattc ccaccaaaat catggcaagt    780
gagggcatca ttggtggcta a                                              801
```

<210> SEQ ID NO 12
<211> LENGTH: 266
<212> TYPE: PRT
<213> ORGANISM: Artificial Sequence
<220> FEATURE:
<223> OTHER INFORMATION: protein hybrid OXA11/OXA7

<400> SEQUENCE: 12

```
Met Lys Thr Phe Ala Ala Tyr Val Ile Thr Ala Cys Leu Ser Ser Thr
1               5                   10                  15

Ala Leu Ala Ser Ser Ile Thr Glu Asn Thr Phe Trp Asn Lys Glu Phe
            20                  25                  30

Ser Ala Glu Ala Val Asn Gly Val Phe Val Leu Cys Lys Ser Ser Ser
        35                  40                  45

Lys Ser Cys Ala Thr Tyr Asn Leu Ala Arg Ala Ser Lys Glu Tyr Leu
    50                  55                  60

Pro Ala Ser Thr Phe Lys Ile Pro Asn Ala Ile Ile Gly Leu Glu Thr
65                  70                  75                  80

Gly Val Ile Lys Asn Glu His Gln Ile Phe Lys Trp Asp Gly Lys Pro
                85                  90                  95

Arg Ala Met Lys Gln Trp Glu Arg Asp Leu Ser Leu Arg Gly Ala Ile
            100                 105                 110

Gln Val Ser Ala Val Pro Val Phe Gln Gln Ile Ala Arg Glu Val Gly
        115                 120                 125

Glu Val Arg Met Gln Lys Tyr Leu Lys Lys Phe Ser Tyr Gly Asn Gln
    130                 135                 140

Asn Ile Ser Gly Gly Ile Asp Lys Phe Trp Leu Glu Gly Gln Leu Arg
145                 150                 155                 160

Ile Ser Ala Val Asn Gln Val Glu Phe Leu Glu Ser Leu Phe Leu Asn
                165                 170                 175
```

Lys Leu Ser Ala Ser Lys Glu Asn Gln Leu Ile Val Lys Glu Ala Leu
            180                 185                 190

Val Thr Glu Ala Ala Pro Glu Tyr Leu Val His Ser Lys Thr Gly Phe
        195                 200                 205

Ser Gly Val Gly Thr Glu Ser Asn Pro Gly Val Ala Trp Trp Val Gly
    210                 215                 220

Trp Val Glu Lys Gly Ala Glu Val Tyr Phe Phe Ala Phe Asn Met Asp
225                 230                 235                 240

Ile Asp Asn Glu Asn Lys Leu Pro Leu Arg Lys Ser Ile Pro Thr Lys
                245                 250                 255

Ile Met Ala Ser Glu Gly Ile Ile Gly Gly
            260                 265

<210> SEQ ID NO 13
<211> LENGTH: 801
<212> TYPE: DNA
<213> ORGANISM: Artificial Sequence
<220> FEATURE:
<223> OTHER INFORMATION: gene hybrid OXA11/OXA7

<400> SEQUENCE: 13
atgaaaacat tgccgcata tgtaattatc gcgtgtcttt cgagtacggc attagctggt      60
tcaattacag aaaatacgtc ttggaacaaa gagttctctg ccgaagccgt caatggtgtc    120
ttcgtgcttt gtaaaagtag cagtaaatcc tgcgctacca atgacttagc tcgtgcatca    180
aaggaatatc ttccagcatc aacatttaag atccccaacg caattatcgg cctagaaact    240
ggtgtcataa ggaatgagca tcaggttttc aaatgggacg gaaagccaag agccatgaag    300
caatgggaaa gagacttgac cttaagaggg gcaatacaag tttcagctgt tcccgtattt    360
caacaaatcg ccagagaagt tggcgaagta agaatgcaga ataccttaa aaaattttcc     420 tatggcagcc agaatatcag tggtggcatt gacaaattct ggttggaaga ccagcttaga    480
atttccgcag ttaatcaagt ggagtttcta gagtctctat atttaaataa attgtcagca    540
tctaaagaaa atcagctaat agtaaaagag gctttggtaa cggaggctgc gcctgaatat    600
cttgtgcatt caaaaactgg ttttttctggt gtgggaactg agtcaaatcc tggtgtcgca    660
tggtgggttg gtgggttga aaggagaca gaggtttact ttttcgcatt taacatggat      720
atagacaacg aaaataagtt gccgctaaga aaattcattc ccaccaaaat catggcaagt    780
gagggcatca ttggtggcta a                                              801

<210> SEQ ID NO 14
<211> LENGTH: 266
<212> TYPE: PRT
<213> ORGANISM: Artificial Sequence
<220> FEATURE:
<223> OTHER INFORMATION: protein hybrid OXA11/OXA7

<400> SEQUENCE: 14

Met Lys Thr Phe Ala Ala Tyr Val Ile Ile Ala Cys Leu Ser Ser Thr
1               5                   10                  15

Ala Leu Ala Gly Ser Ile Thr Glu Asn Thr Ser Trp Asn Lys Glu Phe
            20                  25                  30

Ser Ala Glu Ala Val Asn Gly Val Phe Val Leu Cys Lys Ser Ser Ser
        35                  40                  45

Lys Ser Cys Ala Thr Asn Asp Leu Ala Arg Ala Ser Lys Glu Tyr Leu
    50                  55                  60

```
Pro Ala Ser Thr Phe Lys Ile Pro Asn Ala Ile Gly Leu Glu Thr
 65                  70                  75                  80

Gly Val Ile Arg Asn Glu His Gln Val Phe Lys Trp Asp Gly Lys Pro
             85                  90                  95

Arg Ala Met Lys Gln Trp Glu Arg Asp Leu Thr Leu Arg Gly Ala Ile
            100                 105                 110

Gln Val Ser Ala Val Pro Val Phe Gln Gln Ile Ala Arg Glu Val Gly
            115                 120                 125

Glu Val Arg Met Gln Lys Tyr Leu Lys Lys Phe Ser Tyr Gly Ser Gln
            130                 135                 140

Asn Ile Ser Gly Gly Ile Asp Lys Phe Trp Leu Glu Asp Gln Leu Arg
145                 150                 155                 160

Ile Ser Ala Val Asn Gln Val Glu Phe Leu Glu Ser Leu Tyr Leu Asn
                165                 170                 175

Lys Leu Ser Ala Ser Lys Glu Asn Gln Leu Ile Val Lys Glu Ala Leu
            180                 185                 190

Val Thr Glu Ala Ala Pro Glu Tyr Leu Val His Ser Lys Thr Gly Phe
            195                 200                 205

Ser Gly Val Gly Thr Glu Ser Asn Pro Gly Val Ala Trp Trp Val Gly
            210                 215                 220

Trp Val Glu Lys Glu Thr Glu Val Tyr Phe Phe Ala Phe Asn Met Asp
225                 230                 235                 240

Ile Asp Asn Glu Asn Lys Leu Pro Leu Arg Lys Phe Ile Pro Thr Lys
                245                 250                 255

Ile Met Ala Ser Glu Gly Ile Ile Gly Gly
            260                 265

<210> SEQ ID NO 15
<211> LENGTH: 804
<212> TYPE: DNA
<213> ORGANISM: Artificial Sequence
<220> FEATURE:
<223> OTHER INFORMATION: gene hybrid OXA11/OXA5

<400> SEQUENCE: 15
atgaaaacat tgccgcata tgtaattatc gcgtgtcttt cgagtacggc attagctggt      60
tcaattacag aaaatacgtc ttggaacaaa gagttctctg ccgaagccgt caatggtgtc     120
ttcgtgcttt gtaaaagtag cagtaaatcc tgcgctacca atgacttagc tcgtgcatca     180
aaggaatatc ttccagcatc aacatttaag atccccaacg caattatcgg cctagagact     240
ggtgtcataa agaatgagca tcaggttttc aaatgggacg gaaagccaag agccatgaag     300
caatgggaaa gagacttgac cttaagaggg gcaatacaag tttcagctgt tcccgtattt     360
caacaaatcg ccagagaagt tggcgaagta agaatgcaga ataccttaa aaaattttcc      420 tatggcagcc agaatatcag tggtggcatt gacaaattct ggttggaaga ccagcttaga     480
atttccgcag ttaatcaagt ggagtttcta gagtctctat atttaaataa attgtcagca     540
tctaaagaaa accagctaat agtaaaagag gcaatagtta cagaagcaac tccagaatat     600
atagttcatt caaaaactgg ttttttctggt gtgggaactg agtcaaatcc tggtgtcgca     660
tggtgggttg gtgggttga gaaggagaca gaggtttact ttttcgcctt taacatggat     720
atagacaacg aaagtaagtt gccgctaaga aaatccattc ccaccaaaat catggaaagt     780
gagggcatca tcattggtgg ctaa                                            804

<210> SEQ ID NO 16
```

<211> LENGTH: 267
<212> TYPE: PRT
<213> ORGANISM: Artificial Sequence
<220> FEATURE:
<223> OTHER INFORMATION: protein hybrid OXA11/OXA5

<400> SEQUENCE: 16

```
Met Lys Thr Phe Ala Ala Tyr Val Ile Ile Ala Cys Leu Ser Ser Thr
 1               5                  10                  15

Ala Leu Ala Gly Ser Ile Thr Glu Asn Thr Ser Trp Asn Lys Glu Phe
            20                  25                  30

Ser Ala Glu Ala Val Asn Gly Val Phe Val Leu Cys Lys Ser Ser Ser
        35                  40                  45

Lys Ser Cys Ala Thr Asn Asp Leu Ala Arg Ala Ser Lys Glu Tyr Leu
    50                  55                  60

Pro Ala Ser Thr Phe Lys Ile Pro Asn Ala Ile Ile Gly Leu Glu Thr
65                  70                  75                  80

Gly Val Ile Lys Asn Glu His Gln Val Phe Lys Trp Asp Gly Lys Pro
                85                  90                  95

Arg Ala Met Lys Gln Trp Glu Arg Asp Leu Thr Leu Arg Gly Ala Ile
            100                 105                 110

Gln Val Ser Ala Val Pro Val Phe Gln Gln Ile Ala Arg Glu Val Gly
        115                 120                 125

Glu Val Arg Met Gln Lys Tyr Leu Lys Lys Phe Ser Tyr Gly Ser Gln
    130                 135                 140

Asn Ile Ser Gly Gly Ile Asp Lys Phe Trp Leu Glu Asp Gln Leu Arg
145                 150                 155                 160

Ile Ser Ala Val Asn Gln Val Glu Phe Leu Glu Ser Leu Tyr Leu Asn
                165                 170                 175

Lys Leu Ser Ala Ser Lys Glu Asn Gln Leu Ile Val Lys Glu Ala Ile
            180                 185                 190

Val Thr Glu Ala Thr Pro Glu Tyr Ile Val His Ser Lys Thr Gly Phe
        195                 200                 205

Ser Gly Val Gly Thr Glu Ser Asn Pro Gly Val Ala Trp Trp Val Gly
    210                 215                 220

Trp Val Glu Lys Glu Thr Glu Val Tyr Phe Phe Ala Phe Asn Met Asp
225                 230                 235                 240

Ile Asp Asn Glu Ser Lys Leu Pro Leu Arg Lys Ser Ile Pro Thr Lys
                245                 250                 255

Ile Met Glu Ser Glu Gly Ile Ile Ile Gly Gly
            260                 265
```

<210> SEQ ID NO 17
<211> LENGTH: 801
<212> TYPE: DNA
<213> ORGANISM: Artificial Sequence
<220> FEATURE:
<223> OTHER INFORMATION: gene hybrid OXA11/OXA5

<400> SEQUENCE: 17

```
atgaaaacat tgccgcata tgtaattatc gcgtgtcttt cgagtacggc attagctggt    60
tcaattacag aaaatacgtc ttggaacaaa gagttctctg ccgaagccgt caatggtgtc   120
ttcgtgcttt gtaaaagtag cagtaaatcc tgcgctacca atgacttagc tcgtgcatca   180
aaggaatatc ttccagcatc aacatttaag atccccaacg caattatcgg cctagaaact   240
ggtgtcataa agaatgagca tcaggttttc aaatgggacg gaaagccaag agccatgaag   300
```

```
caatgggaaa gagacttgac cttaagaggg gcaatacaag tttcagctgt tcccgtattt    360
caacaaatcg ccagagaagt tggcgaagta agaatgcaga ataccttaa aaaattttcc    420
tatggcagcc agaatatcag tggtggcatt gacaaattct ggttggaaga ccagcttaga   480
atttccgcag ttaatcaagt ggagtttcta gagtctctat atttaaataa attgtcagca   540
tctaaagaaa accagctaat agtaaaagag ctttggtaa cggaggcggc acctgaatat    600
ctagtgcatt caaaaactgg ttttttctggt gtgggaactg agtcaaatcc tggtgtcgca  660
tggtgggttg ggtgggtaga gaaaggaact gaggtttact ttttcgcctt tagcatggat  720
atagacaacg aaagtaagtt gccgctaaga aaatccattc ccaccaaaat catggaaagt  780
gagggcatca ttggtggcta a                                              801
```

```
<210> SEQ ID NO 18
<211> LENGTH: 266
<212> TYPE: PRT
<213> ORGANISM: Artificial Sequence
<220> FEATURE:
<223> OTHER INFORMATION: protein hybrid OXA11/OXA7

<400> SEQUENCE: 18

Met Lys Thr Phe Ala Ala Tyr Val Ile Ile Ala Cys Leu Ser Ser Thr
1               5                   10                  15

Ala Leu Ala Gly Ser Ile Thr Glu Asn Thr Ser Trp Asn Lys Glu Phe
            20                  25                  30

Ser Ala Glu Ala Val Asn Gly Val Phe Val Leu Cys Lys Ser Ser
        35                  40                  45

Lys Ser Cys Ala Thr Asn Asp Leu Ala Arg Ala Ser Lys Glu Tyr Leu
50                  55                  60

Pro Ala Ser Thr Phe Lys Ile Pro Asn Ala Ile Ile Gly Leu Glu Thr
65                  70                  75                  80

Gly Val Ile Lys Asn Glu His Gln Val Phe Lys Trp Asp Gly Lys Pro
                85                  90                  95

Arg Ala Met Lys Gln Trp Glu Arg Asp Leu Thr Leu Arg Gly Ala Ile
            100                 105                 110

Gln Val Ser Ala Val Pro Val Phe Gln Gln Ile Ala Arg Glu Val Gly
        115                 120                 125

Glu Val Arg Met Gln Lys Tyr Leu Lys Lys Phe Ser Tyr Gly Ser Gln
130                 135                 140

Asn Ile Ser Gly Gly Ile Asp Lys Phe Trp Leu Glu Asp Gln Leu Arg
145                 150                 155                 160

Ile Ser Ala Val Asn Gln Val Glu Phe Leu Glu Ser Leu Tyr Leu Asn
                165                 170                 175

Lys Leu Ser Ala Ser Lys Glu Asn Gln Leu Ile Val Lys Glu Ala Leu
            180                 185                 190

Val Thr Glu Ala Ala Pro Glu Tyr Leu Val His Ser Lys Thr Gly Phe
        195                 200                 205

Ser Gly Val Gly Thr Glu Ser Asn Pro Gly Val Ala Trp Trp Val Gly
210                 215                 220

Trp Val Glu Lys Gly Thr Glu Val Tyr Phe Phe Ala Phe Ser Met Asp
225                 230                 235                 240

Ile Asp Asn Glu Ser Lys Leu Pro Leu Arg Lys Ser Ile Pro Thr Lys
                245                 250                 255

Ile Met Glu Ser Glu Gly Ile Ile Gly Gly
            260                 265
```

<210> SEQ ID NO 19
<211> LENGTH: 804
<212> TYPE: DNA
<213> ORGANISM: Artificial Sequence
<220> FEATURE:
<223> OTHER INFORMATION: gene hybris OXA11/OXA5

<400> SEQUENCE: 19

```
atgaaaacat tgccgcata tgtaattatc gcgtgtcttt cgagtacggc attagctggt      60
tcaattacag aaaatacgtc ttggaacaaa gagttctctg ccgaagccgt caatggtgtc    120
ttcgtgcttt gtaaaagtag cagtaaatcc tgcgctacca atgacttagc tcgtgcatca    180
aaggaatatc ttccagcatc aacatttaag atccccaacg caattatcgg cctagaaact    240
ggtgtcataa agaatgagca tcaggttttc aaatgggacg aaagccaag agccatgaag     300
caatgggaaa gagacttgac cttaagaggg gcaatacaag tttcagctgt tcccgtattt    360
caacaaatcg ccagagaagt tggcgaagta agaatgcaga ataccttaa aaaatttttcc    420
tatggcagcc agaatatcag tggtggcatt gacaaattct ggttggaaga ccagcttaga    480
atttccgcag ttaatcaagt ggagtttcta gagtctctat atttaaataa attgtcagca    540
tctaaagaaa accagctaat agtaaaagag gctttggtaa cggaggcggc acctgaatat    600
ctagtgcatt caaaaactgg ttttttctggt gtgggaactg agtcaaatcc tggtgtcgca    660
tggtgggttg ggtgggttga aaggagaca gaggtttact ttttcgcctt taacatggat    720
atagacaacg agagtaaatt gccgtcaaga aaatccattt caacgaaaat catggcaagt    780
gaaggcatca tcattggtgg ctaa                                           804
```

<210> SEQ ID NO 20
<211> LENGTH: 267
<212> TYPE: PRT
<213> ORGANISM: Artificial Sequence
<220> FEATURE:
<223> OTHER INFORMATION: protein hybrid OXA11/OXA5

<400> SEQUENCE: 20

```
Met Lys Thr Phe Ala Ala Tyr Val Ile Ile Ala Cys Leu Ser Ser Thr
1               5                   10                  15

Ala Leu Ala Gly Ser Ile Thr Glu Asn Thr Ser Trp Asn Lys Glu Phe
            20                  25                  30

Ser Ala Glu Ala Val Asn Gly Val Phe Val Leu Cys Lys Ser Ser Ser
        35                  40                  45

Lys Ser Cys Ala Thr Asn Asp Leu Ala Arg Ala Ser Lys Glu Tyr Leu
    50                  55                  60

Pro Ala Ser Thr Phe Lys Ile Pro Asn Ala Ile Ile Gly Leu Glu Thr
65                  70                  75                  80

Gly Val Ile Lys Asn Glu His Gln Val Phe Lys Trp Asp Gly Lys Pro
                85                  90                  95

Arg Ala Met Lys Gln Trp Glu Arg Asp Leu Thr Leu Arg Gly Ala Ile
            100                 105                 110

Gln Val Ser Ala Val Pro Val Phe Gln Gln Ile Ala Arg Glu Val Gly
        115                 120                 125

Glu Val Arg Met Gln Lys Tyr Leu Lys Lys Phe Ser Tyr Gly Ser Gln
    130                 135                 140

Asn Ile Ser Gly Gly Ile Asp Lys Phe Trp Leu Glu Asp Gln Leu Arg
145                 150                 155                 160

Ile Ser Ala Val Asn Gln Val Glu Phe Leu Glu Ser Leu Tyr Leu Asn
```

```
              165                 170                 175
Lys Leu Ser Ala Ser Lys Glu Asn Gln Leu Ile Val Lys Glu Ala Leu
            180                 185                 190

Val Thr Glu Ala Ala Pro Glu Tyr Leu Val His Ser Lys Thr Gly Phe
        195                 200                 205

Ser Gly Val Gly Thr Glu Ser Asn Pro Gly Val Ala Trp Trp Val Gly
    210                 215                 220

Trp Val Glu Lys Glu Thr Glu Val Tyr Phe Phe Ala Phe Asn Met Asp
225                 230                 235                 240

Ile Asp Asn Glu Ser Lys Leu Pro Ser Arg Lys Ser Ile Ser Thr Lys
                245                 250                 255

Ile Met Ala Ser Glu Gly Ile Ile Ile Gly Gly
            260                 265

<210> SEQ ID NO 21
<211> LENGTH: 801
<212> TYPE: DNA
<213> ORGANISM: Artificial Sequence
<220> FEATURE:
<223> OTHER INFORMATION: gene hybrid OXO11/OXO5

<400> SEQUENCE: 21
atgaaaacat tgccgcata tgtaattatc gcgtgtcttt cgagtacggc attagctggt      60
tcaattacag aaaatacgtc ttggaacaaa gagttctctg ccgaagccgt caatggtgtc    120
ttcgtgcttt gtaaaagtag cagtaaatcc tgcgctacca atgacttagc tcgtgcatca    180
aaggaatatc ttccagcatc aacatttaag atccccaacg caattatcgg cctagaaact    240
ggtgtcataa agaatgagca tcaggttttc aaatgggacg aaagccaag agccatgaag     300 caatgggaaa gagacttgac cttaagaggg gcaatacaag tttcagctgt tcccgtattt    360
caacaaatcg ccagagaagt tggcgaagtg agaatgcaga ataccttaa aaaattttcc     420 tatggcagcc agaatatcag tggtggcatt gacaaattct ggttggaaga ccagcttaga    480
atttccgcag ttaatcaagt ggagtctcta gagtctctat atttaaataa attgtcagca    540
tctaaagaaa accagctaat agtaaaagag gctttggtaa cggaggcggc acctgaatat    600
ctagtgcatt caaaaactgg ttttttctggt gtgggaactg agtcaaatcc tggtgtcgca    660
tggtgggttg ggtgggttga aaggagaca gaggtttact ttttcgcctt taacatggat     720
atagacaacg aaagtaagtt gccgctaaga aaatccattc ccaccaaaat catggaaagt    780
gagggcatca ttggtggcta a                                              801

<210> SEQ ID NO 22
<211> LENGTH: 266
<212> TYPE: PRT
<213> ORGANISM: Artificial Sequence
<220> FEATURE:
<223> OTHER INFORMATION: protein hybrid OXO11/OXO5

<400> SEQUENCE: 22

Met Lys Thr Phe Ala Ala Tyr Val Ile Ile Ala Cys Leu Ser Ser Thr
1               5                  10                  15

Ala Leu Ala Gly Ser Ile Thr Glu Asn Thr Ser Trp Asn Lys Glu Phe
            20                  25                  30

Ser Ala Glu Ala Val Asn Gly Val Phe Val Leu Cys Lys Ser Ser Ser
        35                  40                  45

Lys Ser Cys Ala Thr Asn Asp Leu Ala Arg Ala Ser Lys Glu Tyr Leu
    50                  55                  60
```

```
Pro Ala Ser Thr Phe Lys Ile Pro Asn Ala Ile Ile Gly Leu Glu Thr
 65                  70                  75                  80

Gly Val Ile Lys Asn Glu His Gln Val Phe Lys Trp Asp Gly Lys Pro
                 85                  90                  95

Arg Ala Met Lys Gln Trp Glu Arg Asp Leu Thr Leu Arg Gly Ala Ile
            100                 105                 110

Gln Val Ser Ala Val Pro Val Phe Gln Gln Ile Ala Arg Glu Val Gly
        115                 120                 125

Glu Val Arg Met Gln Lys Tyr Leu Lys Lys Phe Ser Tyr Gly Ser Gln
130                 135                 140

Asn Ile Ser Gly Gly Ile Asp Lys Phe Trp Leu Glu Asp Gln Leu Arg
145                 150                 155                 160

Ile Ser Ala Val Asn Gln Val Glu Ser Leu Glu Ser Leu Tyr Leu Asn
                165                 170                 175

Lys Leu Ser Ala Ser Lys Glu Asn Gln Leu Ile Val Lys Glu Ala Leu
            180                 185                 190

Val Thr Glu Ala Ala Pro Glu Tyr Leu Val His Ser Lys Thr Gly Phe
        195                 200                 205

Ser Gly Val Gly Thr Glu Ser Asn Pro Gly Val Ala Trp Trp Val Gly
    210                 215                 220

Trp Val Glu Lys Glu Thr Glu Val Tyr Phe Phe Ala Phe Asn Met Asp
225                 230                 235                 240

Ile Asp Asn Glu Ser Lys Leu Pro Leu Arg Lys Ser Ile Pro Thr Lys
                245                 250                 255

Ile Met Glu Ser Glu Gly Ile Ile Gly Gly
            260                 265
```

<210> SEQ ID NO 23
<211> LENGTH: 804
<212> TYPE: DNA
<213> ORGANISM: Artificial Sequence
<220> FEATURE:
<223> OTHER INFORMATION: gene hybrid OXO11/OXO5

<400> SEQUENCE: 23

```
atgaaaacat tgccgcata tgtaattatc gcgtgtctttt cgagtacggc attagctggt      60
tcaattacag aaaatacgtc ttggaacaaa gagttctctg ccgaagccgt caatggtgtc    120
ttcgtgcttt gtaaaagtag cagtaaatcc tgcgctacca atgacttagc tcgtgcatca    180
aaggaatatc ttccagcatc aacatttaag atccccaacg caattatcgg cctagaaact    240
ggtgtcataa agaatgagca tcaggttttc aaatgggacg gaaagccaag agccatgaag    300
caatgggaaa gagacttgac cttaagaggg gcaatacaag tttcagctgt tcccgtattt    360
caacaaatcg ccagagaagt tggcgaagta agaatgcaga aataccttaa aaatttttcc    420
tatggcagcc agaatatcag tggtggcatt gacaaattct ggttggaaga ccagcttaga    480
atttccgcag ttaatcaaga ggagtttcta gagtctctat atttaaataa attgtcagca    540
tctaaagaaa accagctaat agtaaaagag gctttggtaa cggaggcggc acctgaatat    600
ctagtgcatt caaaaactgg ttttttctggt gtgggaactg agtcaaatcc tggtgtcgca    660
tggtgggttg ggtgggttga aaaggagaca gaggtttact ttttcgcctt taacatggat    720
atagacaacg aaagtaagtt gccgctaaga aaatccattc ccaccaaaat catggaaagt    780
gagggcatca tcattggtgg ctaa                                            804
```

<210> SEQ ID NO 24
<211> LENGTH: 267
<212> TYPE: PRT
<213> ORGANISM: Artificial Sequence
<220> FEATURE:
<223> OTHER INFORMATION: protein hybrid OXO11/OXO5

<400> SEQUENCE: 24

```
Met Lys Thr Phe Ala Ala Tyr Val Ile Ile Ala Cys Leu Ser Ser Thr
1               5                   10                  15
Ala Leu Ala Gly Ser Ile Thr Glu Asn Thr Ser Trp Asn Lys Glu Phe
            20                  25                  30
Ser Ala Glu Ala Val Asn Gly Val Phe Val Leu Cys Lys Ser Ser Ser
        35                  40                  45
Lys Ser Cys Ala Thr Asn Asp Leu Ala Arg Ala Ser Lys Glu Tyr Leu
    50                  55                  60
Pro Ala Ser Thr Phe Lys Ile Pro Asn Ala Ile Ile Gly Leu Glu Thr
65                  70                  75                  80
Gly Val Ile Lys Asn Glu His Gln Val Phe Lys Trp Asp Gly Lys Pro
                85                  90                  95
Arg Ala Met Lys Gln Trp Glu Arg Asp Leu Thr Leu Arg Gly Ala Ile
            100                 105                 110
Gln Val Ser Ala Val Pro Val Phe Gln Gln Ile Ala Arg Glu Val Gly
        115                 120                 125
Glu Val Arg Met Gln Lys Tyr Leu Lys Lys Phe Ser Tyr Gly Ser Gln
    130                 135                 140
Asn Ile Ser Gly Gly Ile Asp Lys Phe Trp Leu Glu Asp Gln Leu Arg
145                 150                 155                 160
Ile Ser Ala Val Asn Gln Glu Glu Phe Leu Glu Ser Leu Tyr Leu Asn
                165                 170                 175
Lys Leu Ser Ala Ser Lys Glu Asn Gln Leu Ile Val Lys Glu Ala Leu
            180                 185                 190
Val Thr Glu Ala Ala Pro Glu Tyr Leu Val His Ser Lys Thr Gly Phe
        195                 200                 205
Ser Gly Val Gly Thr Glu Ser Asn Pro Gly Val Ala Trp Trp Val Gly
    210                 215                 220
Trp Val Glu Lys Glu Thr Glu Val Tyr Phe Phe Ala Phe Asn Met Asp
225                 230                 235                 240
Ile Asp Asn Glu Ser Lys Leu Pro Leu Arg Lys Ser Ile Pro Thr Lys
                245                 250                 255
Ile Met Glu Ser Glu Gly Ile Ile Ile Gly Gly
            260                 265
```

<210> SEQ ID NO 25
<211> LENGTH: 800
<212> TYPE: DNA
<213> ORGANISM: Artificial Sequence
<220> FEATURE:
<223> OTHER INFORMATION: gene hybrid OXO11/OXO5

<400> SEQUENCE: 25
atgaaaacat tgccgcata tgtaattatc gcgtgtcttt cgagtacggc attagctggt     60
tcaattacag aaaatacgtc ttggaacaaa gagttctctg ccgaagccgt caatggtgtc    120
ttcgtgcttt gtaaaagtag cagtaaatcc tgcgctacca atgacttagc tcgtgcatca    180
aaggaatatc ttccagcatc aacatttaag atccccaacg caattatcgg cctagaaact    240
ggtgtcataa agaatgagca tcaggttttc aaatgggacg gaaagccaag agccatgaag    300

```
caatgggaaa gagacttgag cttaagaggg gcaatacaag tttcagctgt tcccgtattt    360
caacaaatcg ccagagaagt tggcgaagta agaatgcaga gataccttaa aaaattttcc    420
tatggcagcc agaatatcag tggtggcatt gacaaattct ggttggaaga ccagcttaga    480
atttccgcag ttaatcaagt ggagtttcta gagtctctat atttaaataa attgtcagca    540
tctaaagaaa accagctaat agtaaaagag ctttggtaa cggaggcggc acctgaatat     600
ctagtgcatt caaaaactgg ttttcttggt gtgggaactg agtcaaatcc tggtgtcgca    660
tggtgggttg ggtgggttgg gaaggagaca gaggtttact ttttcgcctt taacatggat    720
atagacaacg aaagtaagtt gccgctaaga aatccattcc caccaaaatc atggaaagtg    780
agggcatcat tggtggctaa                                                800
```

<210> SEQ ID NO 26
<211> LENGTH: 266
<212> TYPE: PRT
<213> ORGANISM: Artificial Sequence
<220> FEATURE:
<223> OTHER INFORMATION: protein hybrid OXO11/OXO5

<400> SEQUENCE: 26

```
Met Lys Thr Phe Ala Ala Tyr Val Ile Ile Ala Cys Leu Ser Ser Thr
1               5                   10                  15

Ala Leu Ala Gly Ser Ile Thr Glu Asn Thr Ser Trp Asn Lys Glu Phe
            20                  25                  30

Ser Ala Glu Ala Val Asn Gly Val Phe Val Leu Cys Lys Ser Ser Ser
        35                  40                  45

Lys Ser Cys Ala Thr Asn Asp Leu Ala Arg Ala Ser Lys Glu Tyr Leu
    50                  55                  60

Pro Ala Ser Thr Phe Lys Ile Pro Asn Ala Ile Ile Gly Leu Glu Thr
65                  70                  75                  80

Gly Val Ile Lys Asn Glu His Gln Val Phe Lys Trp Asp Gly Lys Pro
                85                  90                  95

Arg Ala Met Lys Gln Trp Glu Arg Asp Leu Ser Leu Arg Gly Ala Ile
            100                 105                 110

Gln Val Ser Ala Val Pro Val Phe Gln Gln Ile Ala Arg Glu Val Gly
        115                 120                 125

Glu Val Arg Met Gln Arg Tyr Leu Lys Lys Phe Ser Tyr Gly Ser Gln
    130                 135                 140

Asn Ile Ser Gly Gly Ile Asp Lys Phe Trp Leu Glu Asp Gln Leu Arg
145                 150                 155                 160

Ile Ser Ala Val Asn Gln Val Glu Phe Leu Glu Ser Leu Tyr Leu Asn
                165                 170                 175

Lys Leu Ser Ala Ser Lys Glu Asn Gln Leu Ile Val Lys Glu Ala Leu
            180                 185                 190

Val Thr Glu Ala Ala Pro Glu Tyr Leu Val His Ser Lys Thr Gly Phe
        195                 200                 205

Ser Gly Val Gly Thr Glu Ser Asn Pro Gly Val Ala Trp Trp Val Gly
    210                 215                 220

Trp Val Gly Lys Glu Thr Glu Val Tyr Phe Phe Ala Phe Asn Met Asp
225                 230                 235                 240

Ile Asp Asn Glu Ser Lys Leu Pro Leu Arg Lys Ser Ile Pro Thr Lys
                245                 250                 255

Ile Met Glu Ser Glu Gly Ile Ile Gly Gly
            260                 265
```

<210> SEQ ID NO 27
<211> LENGTH: 802
<212> TYPE: DNA
<213> ORGANISM: Artificial Sequence
<220> FEATURE:
<223> OTHER INFORMATION: gene hybrid OXO11/OXO5

<400> SEQUENCE: 27

```
atgaaaacat tgccgcata tgtaattact gcgtgtcttt caagtacggc attagctagt      60
tcaattacag aaaatacgtt ttggaacaaa gagttctctg ccgaagccgt caatggtgtt    120
ttttcgtgct tgtaaaagt agcagtaaat cctgcgctac caataactta gctcgtgcat    180
caaaggaata tcttccagca tcaacattta agatccccaa cgcaattatc ggcctagaaa    240
ctggtgtcat aaagaatgag catcaggttt caaatggga cggaaagcca agagccatga    300
aacaatggga agagacttg agcttaagag gggcaataca agtttcagcg gttcccgtat    360
ttcaacaaat cgccagagaa gttggcgaag taagaatgca gaaatatctt aaaaaatttt    420
catatggtaa ccagaatatc agtggtggca ttgacaaatt ctggttggag ggtcagctta    480
gaatttccgc agttaatcaa gtggagtttc tagagtctct attttttaaat aaattgtcag    540
catcaaaaga aaatcagcta atagtaaaag aggctttggt aacggaggct gcgcctgaat    600
atcttgtgca ttcaaaaact ggttttttctg gtgtgggaac tgagtcaaat cctggtgtcg    660
catggtgggt tggttgggtt gagaagggag cagaggttta ctttttcgca tttaacatgg    720
atatagacaa cgaaaataag ttgccgctaa gaaaatccat tcccaccaaa tcatggcaag    780
tgagggcatc attggtggct aa                                              802
```

<210> SEQ ID NO 28
<211> LENGTH: 266
<212> TYPE: PRT
<213> ORGANISM: Artificial Sequence
<220> FEATURE:
<223> OTHER INFORMATION: protein hybrid OXO11/OXO5

<400> SEQUENCE: 28

```
Met Lys Thr Phe Ala Ala Tyr Val Ile Thr Ala Cys Leu Ser Ser Thr
1               5                   10                  15

Ala Leu Ala Ser Ser Ile Thr Glu Asn Thr Phe Trp Asn Lys Glu Phe
            20                  25                  30

Ser Ala Glu Ala Val Asn Gly Val Phe Val Leu Cys Lys Ser Ser Ser
        35                  40                  45

Lys Ser Cys Ala Thr Asn Asn Leu Ala Arg Ala Ser Lys Glu Tyr Leu
    50                  55                  60

Pro Ala Ser Thr Phe Lys Ile Pro Asn Ala Ile Ile Gly Leu Glu Thr
65                  70                  75                  80

Gly Val Ile Lys Asn Glu His Gln Val Phe Lys Trp Asp Gly Lys Pro
                85                  90                  95

Arg Ala Met Lys Gln Trp Glu Arg Asp Leu Ser Leu Arg Gly Ala Ile
            100                 105                 110

Gln Val Ser Ala Val Pro Val Phe Gln Gln Ile Ala Arg Glu Val Gly
        115                 120                 125

Glu Val Arg Met Gln Lys Tyr Leu Lys Lys Phe Ser Tyr Gly Asn Gln
    130                 135                 140

Asn Ile Ser Gly Gly Ile Asp Lys Phe Trp Leu Glu Gly Gln Leu Arg
145                 150                 155                 160
```

```
Ile Ser Ala Val Asn Gln Val Glu Phe Leu Glu Ser Leu Phe Leu Asn
            165                 170                 175
Lys Leu Ser Ala Ser Lys Glu Asn Gln Leu Ile Val Lys Glu Ala Leu
        180                 185                 190
Val Thr Glu Ala Ala Pro Glu Tyr Leu Val His Ser Lys Thr Gly Phe
    195                 200                 205
Ser Gly Val Gly Thr Glu Ser Asn Pro Gly Val Ala Trp Trp Val Gly
210                 215                 220
Trp Val Glu Lys Gly Ala Glu Val Tyr Phe Phe Ala Phe Asn Met Asp
225                 230                 235                 240
Ile Asp Asn Glu Asn Lys Leu Pro Leu Arg Lys Ser Ile Pro Thr Lys
            245                 250                 255
Ile Met Ala Ser Glu Gly Ile Ile Gly Gly
            260                 265
```

<210> SEQ ID NO 29
<211> LENGTH: 801
<212> TYPE: DNA
<213> ORGANISM: Artificial Sequence
<220> FEATURE:
<223> OTHER INFORMATION: gene hybrid OXO11/OXO5

<400> SEQUENCE: 29

```
atgaaaacat tgccgcata cgtaattact gcgtgtcttt caagtacggc attagctagt        60
tcaattacag aaaatacgtt tggaacaaa gagttctctg ccgaagccgt caatggtgtt       120
ttcgtgcttt gtaaaagtag cagtaaatcc tgcgctacca atgacttagc tcgtgcatca       180
aaggaatatc ttccagcatc aacatttaag atccccaacg caattatcgg cctagaaact       240
ggtgtcataa agaatgagca tcagattttc aaatgggacg aaagccaag agccatgaag        300
caatgggaaa gagacttgac cttaagaggg gcaatacaag tttcagctgt tcccgtattt       360
caacaaatcg ccagagaagt tggcgaagta agaatgcaga ataccttaa aaaattttca        420
tatggtaacc agaatatcag tggtggcatt gacaaattct ggttggaggg tcagcttaga       480
attcccgcag ttaatcaagt ggagtttcta gagtctctat ttttaaataa attgtcagca       540
tcaaaagaaa atcagctaat agtaaaagag ctttggtaa cggaggcggc acctgaatat       600
cttgtgcatt caaaaactgg ttttctggt gtgggaactg agtcaaatcc tggtgtcgca       660
tggtgggttg gttgggttga aagggagca gaggtttact ttttcgcatt taacatggat       720
atagacaacg aaaataagtt gccgctaaga aaatccattc ccaccaaaat catggcaagt       780
gagggcatca ttggtggcta a                                              801
```

<210> SEQ ID NO 30
<211> LENGTH: 266
<212> TYPE: PRT
<213> ORGANISM: Artificial Sequence
<220> FEATURE:
<223> OTHER INFORMATION: protein hybrid OXO11/OXO5

<400> SEQUENCE: 30

```
Met Lys Thr Phe Ala Ala Tyr Val Ile Thr Ala Cys Leu Ser Ser Thr
1               5                   10                  15
Ala Leu Ala Ser Ser Ile Thr Glu Asn Thr Phe Trp Asn Lys Glu Phe
            20                  25                  30
Ser Ala Glu Ala Val Asn Gly Val Phe Val Leu Cys Lys Ser Ser Ser
        35                  40                  45
Lys Ser Cys Ala Thr Asn Asp Leu Ala Arg Ala Ser Lys Glu Tyr Leu
```

```
            50                  55                  60
Pro Ala Ser Thr Phe Lys Ile Pro Asn Ala Ile Ile Gly Leu Glu Thr
 65                  70                  75                  80

Gly Val Ile Lys Asn Glu His Gln Ile Phe Lys Trp Asp Gly Lys Pro
                 85                  90                  95

Arg Ala Met Lys Gln Trp Glu Arg Asp Leu Thr Leu Arg Gly Ala Ile
            100                 105                 110

Gln Val Ser Ala Val Pro Val Phe Gln Gln Ile Ala Arg Glu Val Gly
        115                 120                 125

Glu Val Arg Met Gln Lys Tyr Leu Lys Lys Phe Ser Tyr Gly Asn Gln
    130                 135                 140

Asn Ile Ser Gly Gly Ile Asp Lys Phe Trp Leu Glu Gly Gln Leu Arg
145                 150                 155                 160

Ile Pro Ala Val Asn Gln Val Glu Phe Leu Ser Leu Phe Leu Asn
                165                 170                 175

Lys Leu Ser Ala Ser Lys Glu Asn Gln Leu Ile Val Lys Glu Ala Leu
            180                 185                 190

Val Thr Glu Ala Ala Pro Glu Tyr Leu Val His Ser Lys Thr Gly Phe
        195                 200                 205

Ser Gly Val Gly Thr Glu Ser Asn Pro Gly Val Ala Trp Trp Val Gly
    210                 215                 220

Trp Val Glu Lys Gly Ala Glu Val Tyr Phe Phe Ala Phe Asn Met Asp
225                 230                 235                 240

Ile Asp Asn Glu Asn Lys Leu Pro Leu Arg Lys Ser Ile Pro Thr Lys
                245                 250                 255

Ile Met Ala Ser Glu Gly Ile Ile Gly Gly
            260                 265

<210> SEQ ID NO 31
<211> LENGTH: 801
<212> TYPE: DNA
<213> ORGANISM: Artificial Sequence
<220> FEATURE:
<223> OTHER INFORMATION: gene hybrid OXO11/OXO5

<400> SEQUENCE: 31
atgaaaacat tgccgcata tgtaattatc gcgtgtcttt cgagtacggc attagctggt     60
tcaattacag aaaatacgtc ttggaacaaa gagttctctg ccgaagccgt caatggtgtc    120
ttcgtgcttt gtaaaagtag cagtaaatcc tgcgctacca atgacttagc tcgtgcatca    180
aaggaatatc ttccagcatc aacatttaag atccccaacg caattatcgg cctagaaact    240
ggtgtcataa agaatgagca tcaggttttc aaatgggacg gaaagccaag agccatgaag    300
caatgggaaa gagacttgac cttaagaggg gcaatacaag tttcagctgt tcccgtattt    360
caacaaatcg ccagagaagt tggcgaagta agaatgcaga ataccttaa aaaattttcc    420 tatggcagcc agaatatcag tggtggcatt gacaaattct ggttggaaga ccagcttaga    480
atttccgcag ttaatcaagt ggagtttcta gagtctctat atttaaataa attgtcagca    540
tctaaagaaa accagctaat agtaaaagag gctttggtaa cggaggcggc acctgaatat    600
ctagtgcatt caaaaactgg ttttttctggt gtgggaactg agtcaaatcc tggtgtcgca    660
tggtgggttg ggtgggttga aggagacag aggtttact ttttcgcctt taacatggat     720
atagacaacg aaagtaagtt gccgctaaga aaatccattc ccaccaaaat catggaaagt    780
gagggcatca ttggtggcta a                                              801
```

<210> SEQ ID NO 32
<211> LENGTH: 266
<212> TYPE: PRT
<213> ORGANISM: Artificial Sequence
<220> FEATURE:
<223> OTHER INFORMATION: protein hybrid OXO11/OXO5

<400> SEQUENCE: 32

```
Met Lys Thr Phe Ala Ala Tyr Val Ile Ile Ala Cys Leu Ser Ser Thr
1               5                   10                  15

Ala Leu Ala Gly Ser Ile Thr Glu Asn Thr Ser Trp Asn Lys Glu Phe
            20                  25                  30

Ser Ala Glu Ala Val Asn Gly Val Phe Val Leu Cys Lys Ser Ser Ser
        35                  40                  45

Lys Ser Cys Ala Thr Asn Asp Leu Ala Arg Ala Ser Lys Glu Tyr Leu
    50                  55                  60

Pro Ala Ser Thr Phe Lys Ile Pro Asn Ala Ile Ile Gly Leu Glu Thr
65                  70                  75                  80

Gly Val Ile Lys Asn Glu His Gln Val Phe Lys Trp Asp Gly Lys Pro
                85                  90                  95

Arg Ala Met Lys Gln Trp Glu Arg Asp Leu Thr Leu Arg Gly Ala Ile
            100                 105                 110

Gln Val Ser Ala Val Pro Val Phe Gln Gln Ile Ala Arg Glu Val Gly
        115                 120                 125

Glu Val Arg Met Gln Lys Tyr Leu Lys Lys Phe Ser Tyr Gly Ser Gln
    130                 135                 140

Asn Ile Ser Gly Gly Ile Asp Lys Phe Trp Leu Glu Asp Gln Leu Arg
145                 150                 155                 160

Ile Ser Ala Val Asn Gln Val Glu Phe Leu Glu Ser Leu Tyr Leu Asn
                165                 170                 175

Lys Leu Ser Ala Ser Lys Glu Asn Gln Leu Ile Val Lys Glu Ala Leu
            180                 185                 190

Val Thr Glu Ala Ala Pro Glu Tyr Leu Val His Ser Lys Thr Gly Phe
        195                 200                 205

Ser Gly Val Gly Thr Glu Ser Asn Pro Gly Val Ala Trp Trp Val Gly
    210                 215                 220

Trp Val Glu Lys Glu Thr Glu Val Tyr Phe Phe Ala Phe Asn Met Asp
225                 230                 235                 240

Ile Asp Asn Glu Ser Lys Leu Pro Leu Arg Lys Ser Ile Pro Thr Lys
                245                 250                 255

Ile Met Glu Ser Glu Gly Ile Ile Gly Gly
            260                 265
```

<210> SEQ ID NO 33
<211> LENGTH: 801
<212> TYPE: DNA
<213> ORGANISM: Artificial Sequence
<220> FEATURE:
<223> OTHER INFORMATION: gene hybrid OXO11/OXO5

<400> SEQUENCE: 33

| | |
|---|---|
| atgaaaacat tgccgcata tgtaattatc gcgtgtcttt cgagtacggc attagctggt | 60 |
| tcaattacag aaaatacgtc ttggaacaaa gagttctctg ccgaagccgt caatggtgtc | 120 |
| ttcgtgcttt gtaaaagtag cagtaaatcc tgcgctacca atgacttagc tcgtgcatca | 180 |
| aaggaatatc ttccagcatc aacatttaag atccccaacg caattatcgg cctagaaact | 240 |

```
ggtgtcataa agaatgagca tcaggttttc aaatgggacg gaaagccaag agccatgaag    300
caatgggaaa gagacttgac cttaagaggg gcaatacaag tttcagctgt tcccgtattt    360
caacaaatcg ccagagaagt tggcgaagta agaatgcaga ataccttaa aaaattttcc    420 tatggcagcc agaatatcag tggtggcatt gacaaattct ggttggaaga ccagcttaga    480
atttccgcag ttaatcaagt ggagtttcta gagtctctat atttaaataa attgtcagca    540
tctaaagaaa accagctaat agtaaaagag gctttggtaa cggaggcggc acctgaacat    600
ctagtgcatt caaaaactgg ttttttctggt gtgggaactg agtcaaatcc tggtgtcgca    660
tggtgggttg ggtgggttga gaaggagaca gaggtttact ttttcgcctt taacatggac    720
atagacaacg aaagtaagtt gccgctaaga aaatccattc ccaccaaaat catggaaagt    780
gagggcatca ttggtggcta a                                             801
```

```
<210> SEQ ID NO 34
<211> LENGTH: 266
<212> TYPE: PRT
<213> ORGANISM: Artificial Sequence
<220> FEATURE:
<223> OTHER INFORMATION: protein hybrid OXO11/OXO5

<400> SEQUENCE: 34

Met Lys Thr Phe Ala Ala Tyr Val Ile Ile Ala Cys Leu Ser Ser Thr
 1               5                  10                  15

Ala Leu Ala Gly Ser Ile Thr Glu Asn Thr Ser Trp Asn Lys Glu Phe
            20                  25                  30

Ser Ala Glu Ala Val Asn Gly Val Phe Val Leu Cys Lys Ser Ser Ser
        35                  40                  45

Lys Ser Cys Ala Thr Asn Asp Leu Ala Arg Ala Ser Lys Glu Tyr Leu
    50                  55                  60

Pro Ala Ser Thr Phe Lys Ile Pro Asn Ala Ile Ile Gly Leu Glu Thr
65                  70                  75                  80

Gly Val Ile Lys Asn Glu His Gln Val Phe Lys Trp Asp Gly Lys Pro
                85                  90                  95

Arg Ala Met Lys Gln Trp Glu Arg Asp Leu Thr Leu Arg Gly Ala Ile
            100                 105                 110

Gln Val Ser Ala Val Pro Val Phe Gln Gln Ile Ala Arg Glu Val Gly
        115                 120                 125

Glu Val Arg Met Gln Lys Tyr Leu Lys Lys Phe Ser Tyr Gly Ser Gln
    130                 135                 140

Asn Ile Ser Gly Gly Ile Asp Lys Phe Trp Leu Glu Asp Gln Leu Arg
145                 150                 155                 160

Ile Ser Ala Val Asn Gln Val Glu Phe Leu Glu Ser Leu Tyr Leu Asn
                165                 170                 175

Lys Leu Ser Ala Ser Lys Glu Asn Gln Leu Ile Val Lys Glu Ala Leu
            180                 185                 190

Val Thr Glu Ala Ala Pro Glu His Leu Val His Ser Lys Thr Gly Phe
        195                 200                 205

Ser Gly Val Gly Thr Glu Ser Asn Pro Gly Val Ala Trp Trp Val Gly
    210                 215                 220

Trp Val Glu Lys Glu Thr Glu Val Tyr Phe Phe Ala Phe Asn Met Asp
225                 230                 235                 240

Ile Asp Asn Glu Ser Lys Leu Pro Leu Arg Lys Ser Ile Pro Thr Lys
                245                 250                 255

Ile Met Glu Ser Glu Gly Ile Ile Gly Gly
            260                 265
```

<210> SEQ ID NO 35
<211> LENGTH: 804
<212> TYPE: DNA
<213> ORGANISM: Artificial Sequence
<220> FEATURE:
<223> OTHER INFORMATION: gene hybrid OXO11/OXO5

<400> SEQUENCE: 35

```
atgaaaacat tgccgcata tttaattatc gcgtgtcttt cgagtacggc attagctggt      60
tcaattacag aaaatacgtc ttggaacaaa gagttctctg ccgaagccgt caatggtgtc     120
ttcgtgcttt gtaaaagtag cagtaaatcc tgcgctacca atgacttagc tcgtgcatca     180
aaggaatatc ttccagcatc aacatttaag atccccaacg caattatcgg cctagaaact     240
ggtgtcataa agaatgagca tcaggttttc aaatgggacg gaaagccaag agccatgaag     300
caatgggaaa gagacttgac cttaagaggg gcaatacaag tttcagctgt tcccgtattt     360
caacaaatcg ccagagaagt tggcgaagta agaatgcaga ataccttaa aaaattttcc      420
tatggcagcc agaatatcag tggtggcatt gacaaattct ggttggaaga ccagcttaga     480
atttccgcag ttaatcaagt ggagtttcta gagtctctat atttaaataa attgtcagca     540
tctaaagaaa accagctaat agtaaaagag ctttggtaa cggaggcggc acctgaatat     600
ctagtgcatt caaaaactgg ttttttctggt gtgggaactg agtcaaatcc tggtgtcgca     660
tggtgggttg ggtgggttga aggagaca gaggtttact ttttcgcctt taacatggat     720
atagacaacg aaagtaagtt gccgctaaga aaatccattc ccaccaaaat catggaaagt     780
gagggcatca tcattggtgg ctta                                            804
```

<210> SEQ ID NO 36
<211> LENGTH: 267
<212> TYPE: PRT
<213> ORGANISM: Artificial Sequence
<220> FEATURE:
<223> OTHER INFORMATION: protein hybrid OXO11/OXO5

<400> SEQUENCE: 36

Met Lys Thr Phe Ala Ala Tyr Leu Ile Ile Ala Cys Leu Ser Ser Thr
1               5                   10                  15

Ala Leu Ala Gly Ser Ile Thr Glu Asn Thr Ser Trp Asn Lys Glu Phe
            20                  25                  30

Ser Ala Glu Ala Val Asn Gly Val Phe Val Leu Cys Lys Ser Ser Ser
        35                  40                  45

Lys Ser Cys Ala Thr Asn Asp Leu Ala Arg Ala Ser Lys Glu Tyr Leu
    50                  55                  60

Pro Ala Ser Thr Phe Lys Ile Pro Asn Ala Ile Ile Gly Leu Glu Thr
65                  70                  75                  80

Gly Val Ile Lys Asn Glu His Gln Val Phe Lys Trp Asp Gly Lys Pro
                85                  90                  95

Arg Ala Met Lys Gln Trp Glu Arg Asp Leu Thr Leu Arg Gly Ala Ile
            100                 105                 110

Gln Val Ser Ala Val Pro Val Phe Gln Gln Ile Ala Arg Glu Val Gly
        115                 120                 125

Glu Val Arg Met Gln Lys Tyr Leu Lys Lys Phe Ser Tyr Gly Ser Gln
    130                 135                 140

Asn Ile Ser Gly Gly Ile Asp Lys Phe Trp Leu Glu Asp Gln Leu Arg
145                 150                 155                 160

```
Ile Ser Ala Val Asn Gln Val Glu Phe Leu Glu Ser Leu Tyr Leu Asn
            165                 170                 175

Lys Leu Ser Ala Ser Lys Glu Asn Gln Leu Ile Val Lys Glu Ala Leu
        180                 185                 190

Val Thr Glu Ala Ala Pro Glu Tyr Leu Val His Ser Lys Thr Gly Phe
        195                 200                 205

Ser Gly Val Gly Thr Glu Ser Asn Pro Gly Val Ala Trp Trp Val Gly
        210                 215                 220

Trp Val Glu Lys Glu Thr Glu Val Tyr Phe Phe Ala Phe Asn Met Asp
225                 230                 235                 240

Ile Asp Asn Glu Ser Lys Leu Pro Leu Arg Lys Ser Ile Pro Thr Lys
            245                 250                 255

Ile Met Glu Ser Glu Gly Ile Ile Ile Gly Gly
            260                 265
```

<210> SEQ ID NO 37
<211> LENGTH: 804
<212> TYPE: DNA
<213> ORGANISM: Artificial Sequence
<220> FEATURE:
<223> OTHER INFORMATION: gene hybrid OXO11/OXO5

<400> SEQUENCE: 37

```
atgaaaacat tgccgcata tgtaattatc gcgtgtcttt cgagtacggc attagctggt      60
tcaattacag aaaatacgtc ttggaacaaa gagttctctg ccgaagccgt caatggtgtc    120
ttcgtgcttt gtaaaagtag cagtaaatcc tgcgctacca atgacttagc tcgtgcatca    180
aaggaatatc ttccagcatc aacatttaag atccccaacg caattatcgg cctagaaact    240
ggtgtcataa agaatgagca tcaggttttc aaatgggacg aaagccaag  agccatgaag    300
caatgggaaa gagacttgac cttaagaggg gcaatacaag tttctgctgt tcccgtattt    360
caacaaatcg ccagagaagt tggcgaagta agaatgcaga ataccttaa  aaaattttcc    420
tatggcagcc agaatatcag tggtggcatt gacaaattct ggttggaaga ccagcttaga    480
atttccgcag ttaatcaagt ggagtttcta gagtctctat atttaaataa attgtcagca    540
tctaaagaaa accagctaat agtaaaagag ctttggtaa cggaggcggc acctgaatat    600
ctagtgcatt caaaaactgg ttttctggt  gtgggaactg agtcaaatcc tggtgtcgca    660
tggtgggttg ggtgggttga aaggagact  gaggtttact tttttgcttc taacatggac    720
atagacaatg agagtaaatt gccgtcaaga aatccatttt caacgaaaat catggcaagt    780
gaaggcatca tcattggtgg ctaa                                           804
```

<210> SEQ ID NO 38
<211> LENGTH: 267
<212> TYPE: PRT
<213> ORGANISM: Artificial Sequence
<220> FEATURE:
<223> OTHER INFORMATION: protein hybrid OXO11/OXO5

<400> SEQUENCE: 38

```
Met Lys Thr Phe Ala Ala Tyr Val Ile Ile Ala Cys Leu Ser Ser Thr
1               5                   10                  15

Ala Leu Ala Gly Ser Ile Thr Glu Asn Thr Ser Trp Asn Lys Glu Phe
            20                  25                  30

Ser Ala Glu Ala Val Asn Gly Val Phe Val Leu Cys Lys Ser Ser Ser
        35                  40                  45
```

```
Lys Ser Cys Ala Thr Asn Asp Leu Ala Arg Ala Ser Lys Glu Tyr Leu
     50                  55                  60

Pro Ala Ser Thr Phe Lys Ile Pro Asn Ala Ile Ile Gly Leu Glu Thr
 65                  70                  75                  80

Gly Val Ile Lys Asn Glu His Gln Val Phe Lys Trp Asp Gly Lys Pro
                 85                  90                  95

Arg Ala Met Lys Gln Trp Glu Arg Asp Leu Thr Leu Arg Gly Ala Ile
                100                 105                 110

Gln Val Ser Ala Val Pro Val Phe Gln Gln Ile Ala Arg Glu Val Gly
             115                 120                 125

Glu Val Arg Met Gln Lys Tyr Leu Lys Lys Phe Ser Tyr Gly Ser Gln
130                 135                 140

Asn Ile Ser Gly Gly Ile Asp Lys Phe Trp Leu Glu Asp Gln Leu Arg
145                 150                 155                 160

Ile Ser Ala Val Asn Gln Val Glu Phe Leu Glu Ser Leu Tyr Leu Asn
                165                 170                 175

Lys Leu Ser Ala Ser Lys Glu Asn Gln Leu Ile Val Lys Glu Ala Leu
            180                 185                 190

Val Thr Glu Ala Ala Pro Glu Tyr Leu Val His Ser Lys Thr Gly Phe
            195                 200                 205

Ser Gly Val Gly Thr Glu Ser Asn Pro Gly Val Ala Trp Trp Val Gly
        210                 215                 220

Trp Val Glu Lys Glu Thr Glu Val Tyr Phe Phe Ala Ser Asn Met Asp
225                 230                 235                 240

Ile Asp Asn Glu Ser Lys Leu Pro Ser Arg Lys Ser Ile Ser Thr Lys
                245                 250                 255

Ile Met Ala Ser Glu Gly Ile Ile Ile Gly Gly
            260                 265

<210> SEQ ID NO 39
<211> LENGTH: 801
<212> TYPE: DNA
<213> ORGANISM: Saccharomyces cerevisiae

<400> SEQUENCE: 39
atgaaaacat tgccgcata tgtaattatc gcgtgtcttt cgagtacggc attagctggt      60
tcaattacag aaaatacgtc ttggaacaaa gagttctctg ccgaagccgt caatggtgtc     120
ttcgtgcttt gtaaaagtag cagtaaatcc tgcgctacca atgacttagc tcgtgcatca     180
aaggaatatc ttccagcatc aacatttaag atccccaacg caattatcgg cctagaaact     240
ggtgtcataa agaatgagca tcaggttttc aaatgggacg gaaagccaag agccatgaag     300
caatgggaaa gagacttgac cttaagaggg gcaatacaag tttcagctgt tcccgtattt     360
caacaaatcg ccagagaagt tggcgaagta agaatgcaga ataccttaaa aaatttttcc     420
tatggcagcc agaatatcag tggtggcatt gacaaatcct ggttggaaga ccagcttaga     480
atttccgcag ttaatcaagt ggagtttcta gagtctctat atttaaataa attgtcagca     540
tctaaagaaa accagctaat agtaaaagag ctttggtaa cggaggcggc acctgaatat     600
ctagtgcatt caaaaactgg tttttctggt gtgggaactg agtcaaatcc tggtgtcgca     660
tggtgggttg gtgggttga aggagacaga gggttttact ttttcgcctt taacatggat     720
atagacaacg aaagtaagtt gccgctaaga aaatccattc ccaccaaaat catggaaagt     780
gagggcatca ttggtggcta a                                               801
```

-continued

<210> SEQ ID NO 40
<211> LENGTH: 801
<212> TYPE: DNA
<213> ORGANISM: Saccharomyces cerevisiae

<400> SEQUENCE: 40

| | | | | | |
|---|---|---|---|---|---|
| atgaaaacat | tgccgcata | tgtaattact | gcgtgtcttt | caagtacggc | attagctagt | 60 |
| tcaattacag | aaaatacgtt | ttggaacaaa | gagttctctg | ccgaagccgt | caatggtgtt | 120 |
| ttcgtgcttt | gtaaaagtag | cagtaaatcc | tgcgctacca | ataacttagc | tcgtgcacca | 180 |
| aaggaatatc | ttccagcatc | aacatttaag | atccccaacg | caattatcgg | cctagaaact | 240 |
| ggtgtcataa | agaatgagca | tcagattttc | aaatgggacg | aaaaccaag | agccatgaaa | 300 |
| caatgggaaa | gagacttgag | cttaagaggg | gcaatacaag | tttcagcggt | tcccgtattt | 360 |
| caacaaatcg | ccagagaagt | tggcgaagta | agaatgcaga | aatatcttaa | aaaattttca | 420 |
| tatggtaacc | agaatatcag | tggcggcatt | gacaaattct | ggtcggaggg | tcagcttaga | 480 |
| atttccgcag | ttaatcaagt | ggagtttcta | gagtctctat | ttttaaataa | attgtcagca | 540 |
| tcaaaagaaa | atcagctaat | agtaaaagag | gctttggtaa | cggaggctgc | gcctgaatat | 600 |
| cttgtgcatt | caaaaactgg | ttttctggt | gtgggaactg | agtcaaatcc | tggtgtcgca | 660 |
| tggtgggttg | gttgggttga | aagggagca | gaggtttact | ttttcgcatt | taacatggat | 720 |
| atagacaacg | aaaataagtt | gccgctaaga | aaatccattc | ccaccaaaat | catggcaagt | 780 |
| gagggcatca | ttggtggcta | a | | | | 801 |

<210> SEQ ID NO 41
<211> LENGTH: 804
<212> TYPE: DNA
<213> ORGANISM: Saccharomyces cerevisiae

<400> SEQUENCE: 41

| | | | | | |
|---|---|---|---|---|---|
| atgaaaacca | tagccgcata | cttagttact | tcctgttttt | caagcaccgc | gctctcaaag | 60 |
| tctatttctg | aaaatttggt | gtggaataaa | gaatttttcta | gtgaatccgt | acatggcgtt | 120 |
| tttgtacttt | gtaaaagtag | tagcaattcc | tgtactacaa | ataatgcggc | acgtgcatct | 180 |
| acagcctata | ttccagcatc | aacattcaaa | attcctaatg | ctctaatagg | tcttgaaacc | 240 |
| ggcgccataa | aagatgaacg | gcagattttc | aaatgggacg | gcaagcccag | agccatgaaa | 300 |
| caatgggaaa | aagacttaag | gctaaggggc | gctatacagg | tttctgcggt | tccgtatttt | 360 |
| caacaaattg | ccagagaagt | tggcgaaatg | agaatgcaaa | gatatcttaa | cctgttttca | 420 |
| tacggtaacg | ccaatatagg | gggaggcatt | gacaaattct | ggctagaggg | tcagcttaga | 480 |
| atcccagcat | tcaatcaaga | taaatcttta | gagtcgctct | tcctgaataa | tttgccagca | 540 |
| tcaaaagcaa | atcaactaat | agtaaaagag | gcaatagtta | cagaagctac | gccagaatat | 600 |
| attgttcatt | caaaaactgg | gtattccggt | gttggcacag | aatcaagtcc | tggtgtcgct | 660 |
| tggtgggttg | gttgggtagg | gaaaggagct | gaggtttact | tttttgcatt | taacatggac | 720 |
| atagacaatg | agaataaatt | gccgtcaaga | aaatccatttt | caacgaaaat | catggcaagt | 780 |
| gaaggcatca | tcattggtgg | ctaa | | | | 804 |

<210> SEQ ID NO 42
<211> LENGTH: 827
<212> TYPE: DNA
<213> ORGANISM: Artificial Sequence
<220> FEATURE:
<223> OTHER INFORMATION: OUL3-05-II

<400> SEQUENCE: 42

```
atgaaaacat tgccgcata tgtaattatc gcgtgtcttt cgagtacggc attagctggt      60
tcaattacag aaaatacgtc ttggaacaaa gagttctctg ccgaagccgt caatggtgtc    120
ttcgtgcttt gtaaaagtag cagtaaatcc tgcgctacca atgacttagc tcgtgcatca    180
aaggaatatc ttccagcatc aacattcaaa attcctaatg ctctaatagg tcttgaaacc    240
ggcgccataa aagatgaacg gcaggttttc aaatgggacg gcaagcccag agccatgaag    300
caatgggaaa aagacttaaa gctaaggggc gctatacagg tttctgctgt tccggtattt    360
caacaaattg ccagagaagt tggcgaaata agaatgcaaa ataccttaa cctgttttca    420
tacggcaacg ccaatatagg gggaggcatt gacaaattct ggctagaagg tcagcttaga    480
atctcagcat tcaatcaagt taaattttta gagtcgctct acctgaataa tttgccagca    540
tcaaaagcaa accaactaat agtaaaagag gcaatagtta cagaagcaac tccagaatat    600
atagttcatt caaaaactgg gtattccggt gttggcacag aatcaagtcc tggtgtcgct    660
tggtgggttg gttgggtaga gaaaggaact gaggtttact tttttgcttt taacatggac    720
atagacaatg agagtaaatt gccgtcaaga aaatccattc ccaccaaaat catggcaagt    780
gagggcatca ttggtggcta agctgtgaag atcccagcaa aggctta                  827
```

<210> SEQ ID NO 43
<211> LENGTH: 266
<212> TYPE: PRT
<213> ORGANISM: Artificial Sequence
<220> FEATURE:
<223> OTHER INFORMATION: OUL3-05-II

<400> SEQUENCE: 43

Met Lys Thr Phe Ala Ala Tyr Val Ile Ile Ala Cys Leu Ser Ser Thr
1               5                   10                  15

Ala Leu Ala Gly Ser Ile Thr Glu Asn Thr Ser Trp Asn Lys Glu Phe
            20                  25                  30

Ser Ala Glu Ala Val Asn Gly Val Phe Val Leu Cys Lys Ser Ser Ser
        35                  40                  45

Lys Ser Cys Ala Thr Asn Asp Leu Ala Arg Ala Ser Lys Glu Tyr Leu
    50                  55                  60

Pro Ala Ser Thr Phe Lys Ile Pro Asn Ala Leu Ile Gly Leu Glu Thr
65                  70                  75                  80

Gly Ala Ile Lys Asp Glu Arg Gln Val Phe Lys Trp Asp Gly Lys Pro
                85                  90                  95

Arg Ala Met Lys Gln Trp Glu Lys Asp Leu Lys Leu Arg Gly Ala Ile
            100                 105                 110

Gln Val Ser Ala Val Pro Val Phe Gln Gln Ile Ala Arg Glu Val Gly
        115                 120                 125

Glu Ile Arg Met Gln Lys Tyr Leu Asn Leu Phe Ser Tyr Gly Asn Ala
    130                 135                 140

Asn Ile Gly Gly Gly Ile Asp Lys Phe Trp Leu Glu Gly Gln Leu Arg
145                 150                 155                 160

Ile Ser Ala Phe Asn Gln Val Lys Phe Leu Glu Ser Leu Tyr Leu Asn
                165                 170                 175

Asn Leu Pro Ala Ser Lys Ala Asn Gln Leu Ile Val Lys Glu Ala Ile
            180                 185                 190

Val Thr Glu Ala Thr Pro Glu Tyr Ile Val His Ser Lys Thr Gly Tyr
        195                 200                 205

Ser Gly Val Gly Thr Glu Ser Ser Pro Gly Val Ala Trp Val Gly
    210             215             220

Trp Val Glu Lys Gly Thr Glu Val Tyr Phe Phe Ala Phe Asn Met Asp
225             230             235             240

Ile Asp Asn Glu Ser Lys Leu Pro Ser Arg Lys Ser Ile Pro Thr Lys
                245             250             255

Ile Met Ala Ser Glu Gly Ile Ile Gly Gly
            260             265

<210> SEQ ID NO 44
<211> LENGTH: 801
<212> TYPE: DNA
<213> ORGANISM: Artificial Sequence
<220> FEATURE:
<223> OTHER INFORMATION: OUL3-05-III

<400> SEQUENCE: 44

```
atgaaaacat tgccgcata tttagttctc gcgtgtcttt cgagtacggc attagctggt    60
tcaattacag aaaatacgtc ttggaacaaa gagttctctg ccgaagccgt caatggtgtc   120
ttcgtgcttt gtaaaagtag cagtaaatcc tgcgctacca atgacttagc tcgtgcatca   180
aaggaatatc ttccagcatc aacatttaag atccccaacg caattatcgg tctagaaact   240
ggtgtcataa agaatgagca tcaggttttc aaatgggacg gaaagccaag agccatgaag   300
caatgggaaa gagacttgac cttaagaggg gcaatacaag tttcagctgt tcccgtattt   360
caacaaatcg ccagagaagt tggcgaaata agaatgcaga atatcttaa aaaattttca    420
tatggtaacc agaatatcag tggtggcatt gacaaattct ggctagaagg tcagcttaga   480
atctcagcat tcaatcaagt taaattttta gagtcgctct acctgaataa tttgccagca   540
tcaaaagaaa atcagctaat agtaaaagag gctttggtaa cggaggctgc gcctgaatat   600
cttgtgcatt caaaaactgg tttttctggt gtgggaactg agtcaaatcc tggtgtcgca   660
tggtgggttg gttgggttga aaggggagca gaggtttact ttttcgcatt taacatggat   720
atagacaacg aaaataagtt gccgctaaga aaatccattc ccaccaaaat catggcaagt   780
gagggcatca ttggtggcta a                                              801
```

<210> SEQ ID NO 45
<211> LENGTH: 266
<212> TYPE: PRT
<213> ORGANISM: Artificial Sequence
<220> FEATURE:
<223> OTHER INFORMATION: OUL3-05-III

<400> SEQUENCE: 45

Met Lys Thr Phe Ala Ala Tyr Leu Val Leu Ala Cys Leu Ser Ser Thr
1               5                   10                  15

Ala Leu Ala Gly Ser Ile Thr Glu Asn Thr Ser Trp Asn Lys Glu Phe
            20                  25                  30

Ser Ala Glu Ala Val Asn Gly Val Phe Val Leu Cys Lys Ser Ser Ser
        35                  40                  45

Lys Ser Cys Ala Thr Asn Asp Leu Ala Arg Ala Ser Lys Glu Tyr Leu
    50                  55                  60

Pro Ala Ser Thr Phe Lys Ile Pro Asn Ala Ile Gly Leu Glu Thr
65                  70                  75                  80

Gly Val Ile Lys Asn Glu His Gln Val Phe Lys Trp Asp Gly Lys Pro
                85                  90                  95

Arg Ala Met Lys Gln Trp Glu Arg Asp Leu Thr Leu Arg Gly Ala Ile

```
            100                 105                 110
Gln Val Ser Ala Val Pro Val Phe Gln Gln Ile Ala Arg Glu Val Gly
            115                 120                 125

Glu Ile Arg Met Gln Lys Tyr Leu Lys Lys Phe Ser Tyr Gly Asn Gln
            130                 135                 140

Asn Ile Ser Gly Gly Ile Asp Lys Phe Trp Leu Glu Gly Gln Leu Arg
145                 150                 155                 160

Ile Ser Ala Phe Asn Gln Val Lys Phe Leu Glu Ser Leu Tyr Leu Asn
                165                 170                 175

Asn Leu Pro Ala Ser Lys Glu Asn Gln Leu Ile Val Lys Glu Ala Leu
            180                 185                 190

Val Thr Glu Ala Ala Pro Glu Tyr Leu Val His Ser Lys Thr Gly Phe
            195                 200                 205

Ser Gly Val Gly Thr Glu Ser Asn Pro Gly Val Ala Trp Trp Val Gly
            210                 215                 220

Trp Val Glu Lys Gly Ala Glu Val Tyr Phe Phe Ala Phe Asn Met Asp
225                 230                 235                 240

Ile Asp Asn Glu Asn Lys Leu Pro Leu Arg Lys Ser Ile Pro Thr Lys
                245                 250                 255

Ile Met Ala Ser Glu Gly Ile Ile Gly Gly
            260                 265
```

<210> SEQ ID NO 46
<211> LENGTH: 801
<212> TYPE: DNA
<213> ORGANISM: Artificial Sequence
<220> FEATURE:
<223> OTHER INFORMATION: OUL3-05-IV

<400> SEQUENCE: 46

```
atgaaaacat tgccgcata tgtaattatc gcgtgtcttt cgagtacggc attagctagt      60
tcaattacag aaaatacgtc ttggaacaaa gagttctctg ccgaagccgt caatggtgtc    120
ttcgtgcttt gtaaaagtag cagtaaatcc tgcgctacca atgacttagc tcgtgcatca    180
aaggaatatc ttccagcatc aacatttaag atccccaacg caattatcgg cctagaaact    240
ggtgtcataa agaatgagca tcaggttttc aaatgggacg gaaagccaag agccatgaag    300
caatgggaaa gagacttgac cttaagaggg gcaatacaag tttcagctgt tcccgtattt    360
caacaaatcg ccagagaagt tggcgaaata agaatgcaga atatcttaa aaaattttca     420
tatggtaacc agaatatcag tggtggcatt gacaaattct ggttggaggg tcagcttaga    480
atttccgcag ttaatcaagt ggagtttcta gagtctctat ttttaaataa attgtcagca    540
tcaaaagaaa atcagctaat agtaaaagag gctttggtaa cggaggctgc gcctgaatat    600
cttgtgcatt caaaaactgg ttttctggt gtgggaactg agtcaaatcc tggtgtcgca     660
tggtgggttg gttgggttga aaggggagca gaggtttact ttttcgcatt taacatggat    720
atagacaacg aaaataagtt gccgctaaga aaatccattc ccaccaaaat catggcaagt    780
gagggcatca ttggtggcta a                                              801
```

<210> SEQ ID NO 47
<211> LENGTH: 266
<212> TYPE: PRT
<213> ORGANISM: Artificial Sequence
<220> FEATURE:
<223> OTHER INFORMATION: OUL3_05_IV

<400> SEQUENCE: 47

```
Met Lys Thr Phe Ala Ala Tyr Val Ile Ile Ala Cys Leu Ser Ser Thr
1               5                   10                  15

Ala Leu Ala Ser Ser Ile Thr Glu Asn Thr Ser Trp Asn Lys Glu Phe
            20                  25                  30

Ser Ala Glu Ala Val Asn Gly Val Phe Val Leu Cys Lys Ser Ser
        35                  40                  45

Lys Ser Cys Ala Thr Asn Asp Leu Ala Arg Ala Ser Lys Glu Tyr Leu
    50                  55                  60

Pro Ala Ser Thr Phe Lys Ile Pro Asn Ala Ile Ile Gly Leu Glu Thr
65                  70                  75                  80

Gly Val Ile Lys Asn Glu His Gln Val Phe Lys Trp Asp Gly Lys Pro
                85                  90                  95

Arg Ala Met Lys Gln Trp Glu Arg Asp Leu Thr Leu Arg Gly Ala Ile
            100                 105                 110

Gln Val Ser Ala Val Pro Val Phe Gln Gln Ile Ala Arg Glu Val Gly
        115                 120                 125

Glu Ile Arg Met Gln Lys Tyr Leu Lys Lys Phe Ser Tyr Gly Asn Gln
130                 135                 140

Asn Ile Ser Gly Gly Ile Asp Lys Phe Trp Leu Glu Gly Gln Leu Arg
145                 150                 155                 160

Ile Ser Ala Val Asn Gln Val Glu Phe Leu Glu Ser Leu Phe Leu Asn
                165                 170                 175

Lys Leu Ser Ala Ser Lys Glu Asn Gln Leu Ile Val Lys Glu Ala Leu
            180                 185                 190

Val Thr Glu Ala Ala Pro Glu Tyr Leu Val His Ser Lys Thr Gly Phe
        195                 200                 205

Ser Gly Val Gly Thr Glu Ser Asn Pro Gly Val Ala Trp Trp Val Gly
    210                 215                 220

Trp Val Glu Lys Gly Ala Glu Val Tyr Phe Phe Ala Phe Asn Met Asp
225                 230                 235                 240

Ile Asp Asn Glu Asn Lys Leu Pro Leu Arg Lys Ser Ile Pro Thr Lys
                245                 250                 255

Ile Met Ala Ser Glu Gly Ile Ile Gly Gly
            260                 265

<210> SEQ ID NO 48
<211> LENGTH: 801
<212> TYPE: DNA
<213> ORGANISM: Artificial Sequence
<220> FEATURE:
<223> OTHER INFORMATION: OUL3-05-IX

<400> SEQUENCE: 48
atgaaaacat tagccgcata tttagttcta gttttttatg caagcaccgc gctctcagag     60
tcaattacag aaaatttggc gtggaataaa gaatttttcta gtgaatccgt acatggcgtt    120
tttgtacttt gtaaaagtag tagcaattcc tgtactacaa ataatgcggc acgtgcatct    180
acagcctata ttccagcatc aacattcaaa attcctaatg ctctaatagg tcttgaaacc    240
ggcgccataa aagatgaacg gcaggttttc aaatgggacg gaaagccaag agccatgaag    300
caatgggaaa gagacttaaa gctaaggggc gctatacagg tttctgctgt tccggtattt    360
caacaaattg ccagagaagt tggcgaaata agaatgcaaa aatacctgaa gaagttttca    420
tacggcaacg ccaatatagg gggaggcatt gacaaattct ggctagaagg tcagcttaga    480
atctcagcat tcaatcaagt taaattttta gagtcgctct acctgaataa attgtcagca    540
```

```
tcaaaagaaa accaactaat agtaaaagag gcaatagtta cagaagcaac tccagaatat    600
atagttcatt caaaaactgg tttttctggt gttggcacag aatcaagtcc tggtgtcgct    660
tggtgggttg gttgggtaga gaaaggaact gaggtttact ttttgctttt aacatggac    720 atagacaatg agagtaaatt gccgtcaaga aatccattc ccaccaaaat catggcaagt    780
gagggcatca ttggtggcta a                                             801
```

<210> SEQ ID NO 49
<211> LENGTH: 266
<212> TYPE: PRT
<213> ORGANISM: Artificial Sequence
<220> FEATURE:
<223> OTHER INFORMATION: OUL3-05-IX

<400> SEQUENCE: 49

```
Met Lys Thr Leu Ala Ala Tyr Leu Val Leu Val Phe Tyr Ala Ser Thr
1               5                   10                  15

Ala Leu Ser Glu Ser Ile Thr Glu Asn Leu Ala Trp Asn Lys Glu Phe
            20                  25                  30

Ser Ser Glu Ser Val His Gly Val Phe Val Leu Cys Lys Ser Ser Ser
        35                  40                  45

Asn Ser Cys Thr Thr Asn Asn Ala Ala Arg Ala Ser Thr Ala Tyr Ile
    50                  55                  60

Pro Ala Ser Thr Phe Lys Ile Pro Asn Ala Leu Ile Gly Leu Glu Thr
65                  70                  75                  80

Gly Ala Ile Lys Asp Glu Arg Gln Val Phe Lys Trp Asp Gly Lys Pro
                85                  90                  95

Arg Ala Met Lys Gln Trp Glu Arg Asp Leu Lys Leu Arg Gly Ala Ile
            100                 105                 110

Gln Val Ser Ala Val Pro Val Phe Gln Gln Ile Ala Arg Glu Val Gly
        115                 120                 125

Glu Ile Arg Met Gln Lys Tyr Leu Asn Leu Phe Ser Tyr Gly Asn Ala
    130                 135                 140

Asn Ile Gly Gly Gly Ile Asp Lys Phe Trp Leu Glu Gly Gln Leu Arg
145                 150                 155                 160

Ile Ser Ala Phe Asn Gln Val Lys Phe Leu Glu Ser Leu Tyr Leu Asn
                165                 170                 175

Lys Leu Ser Ala Ser Lys Glu Asn Gln Leu Ile Val Lys Glu Ala Ile
            180                 185                 190

Val Thr Glu Ala Thr Pro Glu Tyr Ile Val His Ser Lys Thr Gly Phe
        195                 200                 205

Ser Gly Val Gly Thr Glu Ser Ser Pro Gly Val Ala Trp Trp Val Gly
    210                 215                 220

Trp Val Glu Lys Gly Thr Glu Val Tyr Phe Phe Ala Phe Asn Met Asp
225                 230                 235                 240

Ile Asp Asn Glu Ser Lys Leu Pro Ser Arg Lys Ser Ile Pro Thr Lys
                245                 250                 255

Ile Met Ala Ser Glu Gly Ile Ile Gly Gly
            260                 265
```

<210> SEQ ID NO 50
<211> LENGTH: 801
<212> TYPE: DNA
<213> ORGANISM: Artificial Sequence
<220> FEATURE:
<223> OTHER INFORMATION: OUL3-05-X

<400> SEQUENCE: 50

```
atgaaaacat tgccgcata tgtaattatc gcgtgtcttt cgagtacggc attagctggt      60
tcaattacag aaatacgtc ttggaacaaa gagttctctg ccgaagccgt caatggtgtc     120
ttcgtgcttt gtaaaagtag cagtaaatcc tgcgctacca atgacttagc tcgtgcatca    180
aaggaatatc ttccagcatc aacatttaag atccccaacg caattatcgg cctagaaact    240
ggtgtcataa agaatgagca tcaggttttc aaatgggacg gaaagccaag agccatgaag    300
caatgggaaa gagacttgac cttaagaggg gcaatacaag tttcagctgt tcccgtattt    360
caacaaatcg ccagagaagt tggcgaagta agaatgcaga aatatcttaa aaaattttca    420
tatggtaacc agaatatcag tggtggcatt gacaaattct ggttggaagg tcagcttaga    480
atttccgcag ttaatcaagt ggagtttcta gagtctctat ttttaaataa attgtcagca    540
tcaaagaaa atcagctaat agtaaaagag ctttggtaa cggaggctgc gcctgaatat      600
cttgtgcatt caaaaactgg ttttctggt gtgggaactg agtcaaatcc tggtgtcgca    660
tggtgggttg gttgggttga aagggagca gaggtttact ttttcgcatt taacatggat    720
atagacaacg aaataagtt gccgctaaga aaatccattc ccaccaaaat catggcaagt    780
gagggcatca ttggtggcta a                                            801
```

<210> SEQ ID NO 51
<211> LENGTH: 266
<212> TYPE: PRT
<213> ORGANISM: Artificial Sequence
<220> FEATURE:
<223> OTHER INFORMATION: OUL3-05-X

<400> SEQUENCE: 51

```
Met Lys Thr Phe Ala Ala Tyr Val Ile Ile Ala Cys Leu Ser Ser Thr
1               5                   10                  15

Ala Leu Ala Gly Ser Ile Thr Glu Asn Thr Ser Trp Asn Lys Glu Phe
            20                  25                  30

Ser Ala Glu Ala Val Asn Gly Val Phe Val Leu Cys Lys Ser Ser Ser
        35                  40                  45

Lys Ser Cys Ala Thr Asn Asp Leu Ala Arg Ala Ser Lys Glu Tyr Leu
    50                  55                  60

Pro Ala Ser Thr Phe Lys Ile Pro Asn Ala Ile Ile Gly Leu Glu Thr
65                  70                  75                  80

Gly Val Ile Lys Asn Glu His Gln Val Phe Lys Trp Asp Gly Lys Pro
                85                  90                  95

Arg Ala Met Lys Gln Trp Glu Arg Asp Leu Thr Leu Arg Gly Ala Ile
            100                 105                 110

Gln Val Ser Ala Val Pro Val Phe Gln Gln Ile Ala Arg Glu Val Gly
        115                 120                 125

Glu Val Arg Met Gln Lys Tyr Leu Lys Lys Phe Ser Tyr Gly Asn Gln
    130                 135                 140

Asn Ile Ser Gly Gly Ile Asp Lys Phe Trp Leu Glu Gly Gln Leu Arg
145                 150                 155                 160

Ile Ser Ala Val Asn Gln Val Glu Phe Leu Glu Ser Leu Phe Leu Asn
                165                 170                 175

Lys Leu Ser Ala Ser Lys Glu Asn Gln Leu Ile Val Lys Glu Ala Leu
            180                 185                 190

Val Thr Glu Ala Ala Pro Glu Tyr Leu Val His Ser Lys Thr Gly Phe
        195                 200                 205
```

```
Ser Gly Val Gly Thr Glu Ser Asn Pro Gly Val Ala Trp Trp Val Gly
    210                 215                 220

Trp Val Glu Lys Gly Ala Glu Val Tyr Phe Phe Ala Phe Asn Met Asp
225                 230                 235                 240

Ile Asp Asn Glu Asn Lys Leu Pro Leu Arg Lys Ser Ile Pro Thr Lys
                245                 250                 255

Ile Met Ala Ser Glu Gly Ile Ile Gly Gly
                260                 265

<210> SEQ ID NO 52
<211> LENGTH: 1056
<212> TYPE: DNA
<213> ORGANISM: Kluyveromyces

<400> SEQUENCE: 52
atgtctgctc acgaaatccc aaagacccag aaaggtgtta tcttctacga gaccggtggt      60
aagctggaat acaaggacat cgatgtccca accccaaagg ccaacgagct tttggtcaac     120
gtcaagtact ccggtgtgtg ccacactgac ttgcacgcct accacggtga ctggccattg     180
ccagttaagt tgcctctagt cggtggccac gagggtgccg gtgtcgttgt cgccatgggt     240
gagaacgtca agggctggaa ggtcggtgac ttggccggta tcaagtggtt gaacggctcc     300
tgtatgtcct gtgagtcctg tgagttgggt aacgagtcca actgtccaga ggctgacttg     360
tccggttaca cccacgacgg ttcttttcca gagtacgcta ctgccgatgc cgtccaggcc     420
gctaagatcc agctggcgc tgaccttgct gagatcgccc aatcctgtg tgccggtatc       480 actgtctaca aggctttgaa gtctgctaac ttgcaggccg tgactgggt tgccatctcc      540 ggtgccgccg gtggtttggg ttccctagcc gtccagtacg ccaaggccat gggttaccgt    600
gtcttgggta tcgacggtgg tgaggagaag gagcagctct tcagacagtt gggtggtgag    660
gtcttcatcg acttcagaac ctgcaaggac atcgagggtg agatcatcaa ggccaccaac    720
ggtggtgctc acggtgtcat caacgtctct gtctccgagg ccgccatcga gtcctctacc    780
aactacgtca gagccaacgg taccgtcgtc ttggtcggtt tgccagctgg cgccaagtgc    840
aagtctgacg ttttcaacca ggtcgtcaag tccatctcta cgtcggttc ttacgtcggt     900 aacagagctg acaccagaga ggctctagac ttcttcgtcc gtggtttggt cagatctcca    960
atcaaggttg tcggtctatc tactctacca gagatttcg agaagatgga aagggccaa   1020 attgttggca gatacgttgt cgacacctcc aactaa                              1056

<210> SEQ ID NO 53
<211> LENGTH: 1045
<212> TYPE: DNA
<213> ORGANISM: Saccharomyces

<400> SEQUENCE: 53
atgtctatcc cagaaactca aaaggtgtt atcttctacg aatcccacgg taagttggaa       60
tacaaagata ttccagttcc aaagccaaag gccaacgaat tgttgatcaa cgttaaatac    120
tctggtgtct gtcacactga cttgcacgct tggcacggtg actggccatt gccagttaag    180
ctaccattag tcggtggtca cgaaggtgcc ggtgtcgttg tcggcatggg tgaaaacgtt    240
aagggctgga agatcggtga ctacgccggt atcaaatggt tgaacggttc ttgtatggcc    300
tgtgaatact gtgaattggg taacgaatcc aactgtcctc acgctgactt gtctggttac    360
acccacgacg gttcttttcca acaatacgct accgctgacg ctgttcaagc cgctcacatt    420
cctcaaggta ccgacttggc ccaagtcgcc cccatcttgt gtgctggtat caccgtctac    480
```

```
aaggctttga agtctgctaa cttgatggcc ggtcactggg ttgctatctc cggtgctgct      540
ggtggtctag gttctttggc tgttcaatac gccaaggcta tgggttacag agtcttgggt      600
attgacggtg gtgaaggtaa ggaagaatta ttcagatcca tcggtggtga agtcttcatt      660
gacttcacta aggaaaagga cattgtcggt gtgttctaaa ggccactgac ggtggtgctc      720
acggtgtcat caacgtttcc gttccgaagc cgctattgaa gcttctacca gatacgttag      780
agctaacggt accaccgttt tggtcggtat gccagctggt gccaagtgtt gttctgatgt      840
cttcaaccaa gtcgtcaagt ccatctctat tgttggttct tacgtcggta acagagctga      900
caccagagaa gctttggact tcttcgccag aggtttggtc aagtctccaa tcaaggttgt      960
cggcttgtct accttgccag aaatttacga aaagatggaa aagggtcaaa tcgttggtag     1020
atacgttgtt gacacttcta aataa                                           1045
```

<210> SEQ ID NO 54
<211> LENGTH: 1047
<212> TYPE: DNA
<213> ORGANISM: Artificial Sequence
<220> FEATURE:
<223> OTHER INFORMATION: Clon A02

<400> SEQUENCE: 54

```
atgtctatcc cagaaactca aaaggtgtt atcttctacg aatcccacgg taagttggaa       60
tacaaagata ttccagttcc aaagccaaag gccaacgaat gttgatcaa cgttaaatac      120 tctggtgtct gtcacactga cttgcacgct tggcacggtg actggccatt gccagttaag     180
ctaccattag tcggtggtca cgaaggtgcc ggtgtcgttg tcggcatggg tgaaaacgtt     240
aagggctgga agatcggtga ctacgccggt atcaaatggt tgaacggttc ttgtatggcc     300
tgtgaatact gtgaattggg taacgaatcc aactgtccag aggctgactt gtccggttac     360
acccacgacg gttcttttcca gcagtacgct actgccgatg ccgtccaggc cgctaagatc     420
ccagctggcg ctgaccttgc tgagatcgcc ccaatcctgt gtgccggtat cactgtctac     480
aaggctttga gtctgctaa cttgcaggcc ggtgactggg ttgccatctc cggtgccgcc      540 ggtggttttgg gttccctagc cgtccagtac gccaaggcca tgggttaccg tgtcttgggt     600
atcgacggtg gtgaggagaa ggagcagctc ttcagacagt tgggtggtga ggtcttcatc     660
gacttcagaa cctgcaagga catcgagggt gagatcatca aggccaccaa cggtggcgct     720
cacggtgtca tcaacgtctc tgtctccgag ccgccatcg agtcctctac caactacgtc      780
agagccaacg gtaccgtcgt cttggtcggt ttgccagctg cgccaagtg caagtctgac      840 gttttcaacc aggtcgtcaa gtccatctct atcgtcggtt cttacgtcgg taacagagct     900
gacaccagag aggctctaga cttcttcgtc cgtggtttgg tcagatctcc aatcaaggtt    960
gtcggtctat ctactctacc agagatttc gagaagatgg agaagggcca aattgttggc    1020
agatacgttg tcgacacctc caactaa                                       1047
```

<210> SEQ ID NO 55
<211> LENGTH: 1060
<212> TYPE: DNA
<213> ORGANISM: Artificial Sequence
<220> FEATURE:
<223> OTHER INFORMATION: Clon A03

<400> SEQUENCE: 55

```
gccatgggtg agaatgtcta tcccagaaac tcaaaaaggt gttatcttct acgaatccca       60
```

```
cggtaagttg gaatacaaag atattccagt tccaaagcca aaggccaacg aattgttgat         120
caacgttaaa tactctggtg tctgtcacac tgacttgcac gcttggcacg gtgactggcc         180
attgccagtt aagctaccat tagtcggtgg tcacgaaggt gccggtgtcg ttgtcgccat         240
gggtgagaac gtcaagggct ggaaggtcgg tgacttggcc ggtatcaagt ggttgaacgg         300
ctcctgtatg tcctgtgagt cctgtgagtt gggtaacgag tccaactgtc cagaggctga         360
cttgtccggt tacacccacg acggttcttt ccagcagtac gctactgccg atgccgtcca         420
ggccgctaag atcccagctg cgctgacctt gctgagatc gccccaatcc tgtgtgccgg         480
tatcactgtc tacaaggctt tgaagtctgc taacttgcag gccggtgact gggttgccat         540
ctccggtgcc gccggtggtt tgggttccct agccgtccag tacgccaagg ccatgggtta         600
ccgtgtcttg ggtatcgacg gtggtgagga aaggagcag ctcttcagac agttgggtgg         660
tgaggtcttc atcgacttca gaacctgcaa ggacatcgag ggtgagatca tcaaggccac         720
caacggtggt gctcacggtg tcatcaacgt ctctgtctcc gaggccgcca tcgagtcctc         780
taccaactac gtcagagcca acggtaccgt cgtcttggtc ggtttgccag ctggcgccaa         840
gtgcaagtct gacgttttca accaggtcgt caagtccatc tctatcgtcg gttcttacgt         900
cggtaacaga gctgacacca gagaggctct agacttcttc gtccgtggtt tggtcagatc         960
tccaatcaag gttgtcggtc tatctactct accagagatt ttcgagaaga tggagaaggg        1020
ccaaattgtt ggcagatacg ttgtcgacac ctccaactaa                              1060
```

<210> SEQ ID NO 56
<211> LENGTH: 1047
<212> TYPE: DNA
<213> ORGANISM: Artificial Sequence
<220> FEATURE:
<223> OTHER INFORMATION: Clon A05

<400> SEQUENCE: 56

```
atgtctatcc caaagaccca gaaaggtgtt atcttctacg agaccggtgg taagctggaa          60
tacaaggaca tcgatgtccc aaccccaaag gccaacgagc ttttggtcaa cgtcaagtac         120
tccggtgtgt gccacactga cttgcacgcc taccacggtg actggccatt gccagttaag         180
ttgcctctag tcggtggcca cgagggtgcc ggtgtcgttg tcgccatggg tgagaacgtc         240
aagggctgga aggtcggtga cttggccggt atcaagtggt tgaacggctc ctgtatgtcc         300
tgtgagtcct gtgagttggg taacgagtcc aactgtccag aggctgactt gtccggttac         360
acccacgacg gttctttcca gcagtacgct actgccgatg ccgtccaggc cgctaagatc         420
ccagctggcg ctgaccttgc tgagatcgcc ccaatcctgt gtgccggtat cactgtctac         480
aaggctttga gtctgctaa cttgcaggcc ggtgactggg ttgccatctc cggtgccgcc         540
ggtggtttgg gttccctagc cgtccagtac gccaaggcca tgggttaccg tgtcttgggt         600
atcgacggtg gtgaggagaa ggagcagctc ttcagacagt tgggtggtga ggtcttcatc         660
gacttcagaa cctgcaagga catcgagggt gagatcatca aggccaccaa cggtggtgct         720
cacggtgtca tcaacgtctc tgtctccgag gccgccatcg agtcctctac caactacgtc         780
agagccaacg gtaccgtcgt cttggtcggt ttgccagctg gcgccaagtg caagtctgac         840
gttttcaacc aggtcgtcaa gtccatctct atcgtcggtt cttacgtcgg taacagagct         900
gacaccagag aggctctaga cttcttcgtc cgtggtttgg tcagatctcc aatcaaggtt         960
gtcggtctat ctactctacc agagattttc gagaagatgg agaagggcca aattgttggc        1020
agatacgttg tcgacaccct caactaa                                            1047
```

<210> SEQ ID NO 57
<211> LENGTH: 1047
<212> TYPE: DNA
<213> ORGANISM: Artificial Sequence
<220> FEATURE:
<223> OTHER INFORMATION: Clon A06

<400> SEQUENCE: 57

| | | | | | |
|---|---|---|---|---|---|
| atgtctatcc | cagaaactca | aaaggtgtt | atcttctacg | aatcccacgg | taagttggaa | 60 |
| tacaaagata | ttccagttcc | aaagccaaag | gccaacgaat | tgttgatcaa | cgttaaatac | 120 |
| tctggtgtct | gtcacactga | cttgcacgct | tggcacggtg | actggccatt | gccagttaag | 180 |
| ctaccattag | tcggtggtca | cgaaggtgcc | ggtgtcgttg | tcggcatggg | tgaaaacgtt | 240 |
| aagggctgga | agatcggtga | ctacgccggt | atcaaatggt | tgaacggttc | ttgtatggcc | 300 |
| tgtgaatact | gtgaattggg | taacgagtcc | aactgtccag | aggctgactt | gtctggttac | 360 |
| acccacgacg | gttctttcca | acaatacgct | actgccgatg | ccgtccaggc | cgctaagatc | 420 |
| ccagctggcg | ctgaccttgc | tgagatcgcc | ccaatcctgt | gtgccggtat | cactgtctac | 480 |
| aaggctttga | gtctgctaa | cttgcaggcc | ggtgactggg | ttgccatctc | cggtgccgcc | 540 |
| ggtggtttgg | gttccctagc | cgtccagtac | gccaaggcca | tgggttaccg | tgtcttgggt | 600 |
| atcgacggtg | gtgaggagaa | ggagcagctc | ttcagacagt | tgggtggtga | ggtcttcatc | 660 |
| gacttcagaa | cctgcaagga | catcgagggt | gagatcatca | aggccaccaa | cggtggtgct | 720 |
| cacggtgtca | tcaacgtctc | tgtctccgag | gccgccatcg | agtcctctac | caactacgtc | 780 |
| agagccaacg | gtaccgtcgt | cttggtcggt | ttgccagccg | gcgccaagtg | caagtctgac | 840 |
| gttttcaacc | aggtcgtcaa | gtccatctct | atcgtcggtt | cttacgtcgg | taacagagct | 900 |
| gacaccagag | aggctctaga | cttcttcgtc | cgtggtttgg | tcagatctcc | aatcaaggtt | 960 |
| gtcggtctat | ctactctacc | agagattttc | gagaagatgg | agaagggcca | aattgttggc | 1020 |
| agatacgttg | tcgacaccctc | caactaa | | | | 1047 |

<210> SEQ ID NO 58
<211> LENGTH: 1049
<212> TYPE: DNA
<213> ORGANISM: Artificial Sequence
<220> FEATURE:
<223> OTHER INFORMATION: Clon A10

<400> SEQUENCE: 58

| | | | | | |
|---|---|---|---|---|---|
| atgtctatcc | cagaaactca | aaaggtgtt | atcttctacg | agaccggtgg | taagctggaa | 60 |
| tacaaggaca | tcgatgtccc | aaccccaaag | gccaacgagc | ttttggtcaa | cgtcaagtac | 120 |
| tccggtgtgt | gccacactga | cttgcacgcc | taccacggtg | actggccatt | gccagttaag | 180 |
| ttgcctctag | tcggtggcca | cgagggtgcc | ggtgtcgttg | tcgccatggg | tgagaacgtc | 240 |
| aagggctgga | aggtcggtga | cttggccggt | atcaagtggt | tgaacggctc | ctgtatgtcc | 300 |
| tgtgagtcct | gtgagttggg | taacgagtcc | aactgtccag | aggctgactt | gtccggttac | 360 |
| acccacgacg | gttctttcca | gcagtacgct | actgccgatg | ccgtccaggc | cgctaagatc | 420 |
| ccagctggcg | ctgaccttgc | tgagatcgcc | ccaatcctgt | gtgccggtat | cactgtctac | 480 |
| aaggctttga | gtctgctaa | cttgcaggcc | ggtgactggg | ttgccatctc | cggtgccgcc | 540 |
| ggtggtttgg | gttccctagc | cgtccagtac | gccaaggcca | tgggtttacc | gtgtcttggg | 600 |
| tatcgacggt | ggtgaggaga | aggagcagct | cttcagacag | ttgggtggtg | aggtcttca | 660 |

```
tcgacttcag aacctgcaag gacatcgagg gtgagatcat caagcccacc aacggtggtg      720
ctcacggtgt catcaacgtc tctgtctccg aggccgccat cgagtcctct accaactacg      780
tcagagccaa cggtaccgtc gtcttggtcg gtttgccagc tggcgccaag tgcaagtctg      840
acgttttcaa ccaggtcgtc aagtccatct ctatcgtcgg ttcttacgtc ggtaacagag      900
ctgacaccag agaggctcta gacttcttcg tccgtggttt ggtcagatct ccaatcaagg      960
ttgtcggtct atctactcta ccagagattt cgagaagat ggagaagggc caaattgttg      1020
gcagatacgt tgtcgacacc tccaactaa                                       1049

<210> SEQ ID NO 59
<211> LENGTH: 1047
<212> TYPE: DNA
<213> ORGANISM: Artificial Sequence
<220> FEATURE:
<223> OTHER INFORMATION: Clon A11

<400> SEQUENCE: 59
atgtctatcc cagaaactca aaaaggtgtt atcttctacg aatcccacgg taagttggaa      60
tacaaagata ttccagttcc aaagccaaag gccaacgaat tgttgatcaa cgttaaatac     120
tctggtgtct gtcacactga cttgcacgct tggcacggtg actggccatt gccagttaag     180
ctaccattag tcggtggtca cgaaggtgcc ggtgtcgttg tcggcatggg tgaaaacgtt     240
aagggctgga agatcggtga ctacgccggt atcaaatggt tgaacggttc ttgtatggcc     300
tgtgaatact gtgaattggg taacgaatcc aactgtcctc acgctgactt gtctggttac     360
acccacgacg gttcttttcca gcagtacgct actgccgatg ccgtccaggc cgctaagatc     420
ccagctggcg ctgaccttgc tgagatcgcc ccaatcctgt gtgccggtat cactgtctac     480
aaggctttga gtctgctaa cttgcaggcc ggtgactggg ttgccatctc cggtgccgcc     540
ggtggtttgg gttccctagc cgtccagtac gccaaggcca tgggttaccg tgtcttgggt     600
atcgacggtg gtgaggagaa ggagcagctc ttcagacagt tgggtggtga ggtcttcatc     660
gacttcagaa cctgcaagga catcgagggt gagatcatca aggccaccaa cggtggtgct     720
cacggtgtca tcaacgtctc tgtctccgag gccgccatcg agtcctctac caactacgtc     780
agagccaacg gtaccgtcgt cttggtcggt ttgccagctg gcgccaagtg caagtctgac     840
gttttcaacc aggtcgtcat gtccatctct atcgtcggtt cttacgtcgg taacagagct     900
gacaccagag aggctctaga cttcttcgtc cgtggtttgg tcagatctcc aatcaaggtt     960
gtcggtctat ctactctacc agagattttc gagaagatgg agaagggcca aattgttggc    1020
agatacgttg tcgacacctc caactaa                                        1047
```

METHOD OF GENERATING GENE MOSAICS

CROSS-REFERENCE TO RELATED APPLICATIONS

This application is the U.S. national stage of International Patent Application No. PCT/EP2011/055530, filed on Apr. 8, 2011 and entitled METHOD OF GENERATING GENE MOSAICS, which claims the benefit of priority under 35 USC §120 from U.S. Patent Application No. 61/322,680, filed on Apr. 9, 2010 and under 35 USC §119 from European Patent Application No. 10159515.5, filed on Apr. 9, 2010. The disclosures of the foregoing applications are incorporated herein by reference in their entirety.

SEQUENCE LISTING

The entire content of a Sequence Listing titled "Sequence_Listing.txt," created on Oct. 9, 2012 and having a size of 100 kilobytes, which has been submitted in electronic form in connection with the present application, is hereby incorporated by reference herein in its entirety.

The invention refers to methods of generating gene mosaics by homeologous in vivo recombination.

BACKGROUND

One of the primary goals of protein design is to generate proteins with new or improved properties. The ability to confer a desired activity on a protein or enzyme has considerable practical application in the chemical and pharmaceutical industry. Directed protein evolution has emerged as a powerful technology platform in protein engineering, in which libraries of variants are searched experimentally for clones possessing the desired properties.

Directed protein evolution harnesses the power of natural selection to evolve proteins or nucleic acids with desirable properties not found in nature. Various techniques are used for generating protein mutants and variants and selecting desirable functions. Recombinant DNA technologies have allowed the transfer of single structural genes or genes for an entire pathway to a suitable surrogate host for rapid propagation and/or high-level protein production. Accumulated improvements in activity or other properties are usually obtained through iterations of mutation and screening. Applications of directed evolution are mainly found in academic and industrial laboratories to improve protein stability and enhance the activity or overall performance of enzymes and organisms or to alter enzyme substrate specificity and to design new activities. Most directed evolution projects seek to evolve properties that are useful to humans in an agricultural, medical or industrial context (biocatalysis).

The evolution of whole metabolic pathways is a particularly attractive concept, because most natural and novel compounds are produced by pathways rather than by single enzymes. Metabolic pathways engineering usually requires the coordinated manipulation of all enzymes in the pathway. The evolution of new metabolic pathways and the enhancement of bioprocessing usually is performed through a process of iterative cycles of recombination and screening or selection to evolve individual genes, whole plasmids, multigene clusters, or even whole genomes.

Shao et al (Nucleic Acids Research 37(2):e16 Epub 2008 Dec. 12) describe the assembly of large recombinant DNA encoding a whole biochemical pathway or genome in a single step via in vivo homologous recombination of two flanking (anchoring) regions at the 5' and 3' ends containing sequences of the 5' or 3' end of the adjacent fragment in *Saccharomyces cerevisiae*.

Elefanty et al. (Proc. Natl. Acad. Sci. 95, 11897-11902 (1998) describe gene targeting experiments to generate mutant mice, in which the lacZ reporter gene has been knocked in to the SCL locus. Reference is made to FIG. 1 showing the SCL-lacZ gene targeting strategy employing two anchoring sequences, i.e. one at each of the 5' and 3' end.

Directed evolution can be performed in living cells, also called in vivo evolution, or may not involve cells at all (in vitro evolution). In vivo evolution has the advantage of selecting for properties in a cellular environment, which is useful when the evolved protein or nucleic acid is to be used in living organisms. In vivo homologous recombination in yeast has been widely used for gene cloning, plasmid construction and library creation.

Library diversity is obtained through mutagenesis or recombination. DNA shuffling allows the direct recombination of beneficial mutations from multiple genes. In DNA shuffling a population of DNA sequences are randomly fragmented and then reassembled into full-length hybrid sequences.

For the purpose of homologous recombination naturally occurring homologous genes are used as the source of starting diversity. Single-gene shuffling library members are typically more than 95% identical. The familiy-shuffling, however, allows block exchanges of sequences that are typically more than 60% identical. The functional sequence diversity comes from related parental sequences that have survived natural selection; thus, much larger numbers of mutations are tolerated in a given sequence without introducing deleterious effects on the structure or function.

The recombination of DNA fragments of different origin with up to 30% diversity is described in WO1990007576A1. Hybrid genes are produced in vivo by intergeneric and/or interspecific recombination in mismatch repair deficient bacteria or in bacteria of which the mismatch repair (MMR) system is transitorily inactivated. Thereby those processes by which damaged DNA are repaired, are avoided, which would have an inhibitory effect on the recombination frequency between divergent sequences, i.e. homeologous recombination.

A review of basic mechanisms of MMR is provided by Kunz et al (Cell. Mol. Life. Sci. 66 (2009) 1021-1038).

Targeted homeologous recombination is described in MMR deficient plants (WO2006/134496A2). Targeting to a locus with sequences having up to 10% differences was possible.

Homologous recombination into bacteria for the generation of polynucleotide libraries is disclosed in WO03/095658A1. An expression library of polynucleotides was generated, wherein each polynucleotide is integrated by homologous recombination into the genome of a competent bacterium host cell, using a non-replicating linear integration cassette comprising the polynucleotide and two flanking sequences homologous with a region of the host cell genome.

The diversity of libraries can be enhanced by taking advantage of the ability of haploid cells to efficiently mate leading to the formation of a diploid organism. In its vegetative life cycle *S. cerevisiae* cells have a haploid genome, i.e. every chromosome is present as a single copy. Under certain conditions the haploid cells can mate. By this way a diploid cell is formed. Diploid cells can form haploid cells again, especially when certain nutrients are missing. They then undergo a process called meiosis followed by sporulation to form four haploid spores. During meiosis the different chromosomes of the two parental genomes recombine. During meiotic recombination DNA fragments are exchanged resulting in recombined DNA material.

WO2005/075654A1 discloses a system for generating recombinant DNA sequences in *Saccharomyces cerevisiae*, which is based on the sexual reproductive cycle of *S. cerevisiae*. Heterozygous diploid cells are grown under conditions which induce the processes of meiosis and spore formation. Meiosis is generally characterized by elevated frequencies of genetic recombination. Thus, the products of meiosis, which are haploid cells or spores, can contain recombinant DNA sequences due to recombination between the two diverged DNA sequences. By an iterative method recombinant haploid progeny is selected and mated to one another, the resulting diploids are sporulated again, and their progeny spores are subjected to appropriate selection conditions to identify new recombination events. This process is described in wild-type or mismatch repair defective *S. cerevisiae* cells. Therefore, the genes of interest, each flanked by two selection markers, are integrated into an identical locus of each of the two sister chromosomes of mismatch repair deficient diploid strains. DNA sequences are added to the 5' or 3' end of the new DNA fragment that are 100% identical to the flanking DNA sequences of the locus where the DNA has to be integrated. These flanking target sequences are about 400-450 nucleotides long. Then the cells are forced to initiate sporulation. During the sporulation the recombination process takes place. The resulting spores and recombinant sequences can be differentiated by selection for the appropriate flanking markers.

The ability of yeast to efficiently recombine homologous DNA sequences can also be exploited to increase the diversity of a library. When two genes that share 89.9% homology were mutated by PCR and transformed into wild type yeast, a chimeric library of 10e7 was created through in vivo homologous recombination, showing several cross-over points throughout the two genes (Swers et al Nucleic Acids Research 32(3) e36 (2004)).

A method of mitotic homeologous recombination is described by Nicholson et al (Genetics 154: 133-146 (2000)). Effects of defined mismatches contained in short inverted repeats on recombination rates in wild-type or MMR-defective strains were investigated.

It is the object of the present invention to provide an improved method of preparing and assembling a diversity of gene mosaics, especially for recombining long DNA fragments. As a result it would be desirable to provide respective libraries of variants for the selection of improved recombinants.

The object is achieved by the provision of the embodiments of the present application.

SUMMARY OF THE INVENTION

The present invention provides a novel method for generating a gene mosaic by somatic in vivo recombination, comprising
  a) in a single step procedure
    (i) transforming a cell with at least one gene A having a sequence homology of less than 99.5% to another gene to be recombined that is an integral part of the cell genome or presented in the framework of a genetic construct,
    (ii) recombining said genes,
    (iii) generating a gene mosaic of the genes at an integration site of a target genome, wherein said at least one gene A has a single flanking target sequence either at the 5' end or 3' end anchoring to the 5' or 3' end of said integration site, and
  b) selecting clones comprising the gene mosaic.

Specifically the invention relates to a method for generating a gene mosaic by somatic in vivo recombination, comprising
  a) in a single step procedure
    (i) transforming a cell with at least one gene A having a sequence homology of less than 99.5% to a different gene B which is an integral part of the cell genome or presented in the framework of a genetic construct or expression cassette,
    (ii) recombining said genes,
    (iii) generating a gene mosaic of genes A and B at an integration site of a target genome, wherein said at least one gene A is linked to a single flanking target sequence either at the 5' end or 3' end of the genetic construct anchoring to the 5' or 3' end of said integration site and
  b) selecting clones comprising the gene mosaic.

It is specifically preferred that a selection marker is used in the gene mosaic and the clones are selected according to the presence of the selection marker. For example, the gene mosaic comprises a selection marker, e.g. where said gene A is linked to a selection marker. Alternatively, selection may also be made by the presence of any product resulting of recombinants, e.g. through determining the yield or functional characteristics. Specifically one or more different selection markers may be used to differentiate the type of gene mosaics.

Specifically the method according to the invention employs said another gene that is part of the target genome, e.g. the genome of the cell. In a preferred embodiment said anther gene is gene B being part of the genome of the cell.

According to an alternatively preferred embodiment, said another gene is a genetic construct separate from the target genome, such as a linear polynucleotide, and optionally integrated into the target genome in the course of the recombination.

According to a specific embodiment of the invention the cell is co-transformed with at least one gene A and at least one gene B, wherein said single flanking target sequence of gene A is anchoring to the 5' end of an integration site on said target genome, and wherein gene B is linked to a single flanking target sequence anchoring to the 3' end of the integration site.

Specifically, the cell can be co-transformed with at least one gene A with a selection marker and at least one gene B, wherein said single flanking target sequence of gene A is anchoring to the 5' end of an integration site on said target genome, and wherein gene B is linked to a different selection marker and a single flanking target sequence anchoring to the 3' end of the integration site, and wherein clones for the at least two selection markers are selected.

Specifically, the cell can be co-transformed with at least two different genes A1 and A2 and optionally with at least two different genes B1 and B2.

According to a specific embodiment, at least one further gene C is co-transformed, which has a sequence hybridizing with a sequence of gene A and/or said another gene to obtain assembly of said further gene C to gene A and/or said another gene.

Specifically, at least one further gene C is co-transformed, which has a sequence hybridizing with a sequence of gene A and/or B, e.g. the full length gene A or gene B or a partial sequence of gene A and/or B, to obtain recombination and assembly of said further gene C to gene A and/or B.

Specifically, the hybridizing sequence of said gene C has a sequence homology of less than 99.5% to said sequence, and preferably at least 30% sequence homology.

Specifically gene mosaics having at least one nucleotide exchange or cross-over within the genes are selected, i.e. mosaics with an intragenic cross-over, such as those comprising parts of gene A and parts of said another gene(s) combined, which is understood as a mixture of partial genes to obtain a recombined intragenic gene mosaic, such as genes suitable for the expression of products in a different way, e.g. having improved properties or at improved yields. Such intragenic gene mosaics can be produced by recombination and preferably also assembly of a series of genes, wherein one or more of the assembled genes have such intragenic gene mosaics.

According to a preferred embodiment, mosaics of at least three different genes A and/or B and/or C can be obtained.

Preferably, said gene A and/or said another gene is coding for a polypeptide or part of a polypeptide having an activity.

Specifically, the inventive method employs genes A, B and/or C which are coding for part of a polypeptide having an activity. Accordingly, the genes, such as genes A and/or B and/or C, preferably all of them do not individually encode a biologically active polypeptide as such, but would encode only part of it, and may bring about a respective activity or modified activity upon gene assembly only.

Using the inventive method, multiple genes coding for polypeptides of a biochemical pathway can be assembled and recombined.

In another specific embodiment, the inventive method provides for recombination and eventual assembly of genes resulting in a non-coding sequence, such as a promoter, untranslated region, ribosomal binding site, terminator, etc.

Any recombination competent eukaryotic or prokaryotic host cell can be used for generating a gene mosaic by somatic in vivo recombination according to the present invention. According to a preferred embodiment of the invention, the cell is a repair deficient cell, e.g. a nucleic acid repair deficient cell, such as with DNA repair deficiency, or an MMR deficient cell.

Specifically, the cell is a eukaryotic cell, preferably a fungal, mammalian or plant cell, or prokaryotic cell.

Preferably the cell is a an *Aspergillus* sp or a fungal cell, preferably, it can be selected from the group consisting of the genera *Saccharomyces, Candida, Kluyveromyces, Hansenula, Schizosaccaromyces, Yarrowia, Pichia* and *Aspergillus*.

Preferably haploid strains, such as haploid yeast strains are employed.

Alternatively, prokaryotes, such as *E. coli, Bacillus, Streptomyces*, or mammalian cells, like HeLa cells or Jurkat cells, or plant cells, like *Arabidopsis*, may be used.

According to a specific embodiment, the flanking target sequence is at least 5 bp, preferably at least 10 bp, more preferably at least 20 bp, 50 bp, 100 bp up to 5,000 bp length. Specifically the flanking target sequence is linked to said gene or is an integral, terminal part of said gene. It is preferred that said the flanking target sequence has homology in the range of 30% to 99.5%, preferably less than 95%, less than 90%, less than 80%, hybridising with the anchoring sequence of said integration site, When at least two different flanking target sequences anchoring to the target integration site of the genome are used according to the invention, it is preferred that they do not recombine with each other, preferably they share less than 30% homology.

Selection markers useful for the inventive method can be selected from the group consisting of any of the known nutrition auxotrophic markers, antibiotics resistance markers, fluorescent markers, knock-in markers, activator/binding domain markers and dominant recessive markers and colorimetric markers. Preferred markers can be temporally inactivated or functionally knocked out, and may be re-established to regain its marking property. Further preferred markers are traceable genes, wherein the marker is a function of either of the gene sequences A and/or the other gene(s), such as gene B, without separate sequences with a marker function, so that the expression of the gene mosaic can be directly determined through detection of the mosaic itself. In this case the gene mosaic is directly traceable.

According to a specific embodiment, said genes are comprised in a linear polynucleotide, a vector or a yeast artificial chromosome. Specifically, gene A and/or other genes to be recombined are in the form of linear polynucleotides, preferably of 300 to 20,000 bp. Specifically, there would be no need to construct or employ plasmids or megaplasmids. The gene(s) can thus be used as such, i.e. without carrier.

The genes used for recombination and integration can also be comprised in any genetic construct, e.g. to be used as vector for carrying said gene(s). Said genes can thus be comprised in a genetic construct, e.g. a linear polynucleotide, a vector or a yeast artificial chromosome. These preferably include linear polynucleotides, plasmids, PCR constructs, artificial chromosomes, like yeast artificial chromosomes, viral vectors or transposable elements.

According to a specific embodiment of the invention the integration site of the target genome is located on either of the genes, e.g. within a linear polynucleotide, a plasmid or chromosome, including artificial chromosomes.

The method according to the invention specifically provides for the selection of at least one clone having an intragenic gene mosaic. Specifically, at least one clone having a gene assembly and at least one intragenic gene mosaic is selected.

Using the method according to the invention gene mosaics of at least 3, preferably at least 9, up to 20,000 base pairs can be obtained, as well as gene mosaics, e.g. comprising at least one intragenic mosaic, preferably with at least 3 cross-over events, preferably at least 4, 5, or 10 cross-over events per 700 base pairs, more preferably per 600 bp, per 500 bp or even below. Typically a high degree of cross-over events provides for a large diversity of recombined genes, which may be used to produce a library for selecting suitable library members. The degree of mosaics or cross-over events can be understood as a quality parameter of such a library.

The genes which are modified according to the method of the invention can be any genes useful for scientific or industrial purposes. These genes can be for example non-coding sequences, e.g. those which may be used for recombinant expression systems, or variants of polypeptides, in whole or in part, including those partial sequences, which do not encode a polypeptide with biological activity, which polypeptides are specifically selected from the group consisting of enzymes, antibodies or parts thereof, cytokines, vaccine antigens, growth factors or peptides. If genes are modified, which encode a non coding sequence or an amino acid sequence as part of a polypeptide having a biological activity, also called "partial genes", it may be preferred that an assembly of such partial genes has functional features, e.g. encodes a polypeptide having a biological activity. Preferably a number of different genes, e.g. different partial genes, at a size ranging from 3 bp to 20,000 bp, specifically at least 100 bp, preferably from 300 bp to 20,000 bp, specifically up to 10,000 bp, are recombined, which number of different genes of is at least 2, more specifically at least 3, 4, 5, 6, 7, 8, 9, or at least 10 to produce a recombined gene sequence that is non-coding or encoding a recombinant polypeptide, e.g. having a biological activity, which is advantageously modulated, e.g. having an increased biological activity. The term "biological activity" as used in this regard specifically refers to an enzymatic activity, such as an activity that converts a particular substrate into a particular product. Preferred genes as diversified according to the invention are coding for multi-chain polypeptides.

According to a particular embodiment of the invention there is provided a method of cell display of gene variants, comprising creating a variety of gene mosaics in cells using the method according to the invention, and displaying said variety on the surface of said cells to obtain a library of mosaics.

The library obtainable by such preferred display specifically comprises a high percentage of gene mosaics within a functional open reading frame (ORF), preferably at least 80%.

A library according to the invention specifically may be in any suitable form, specifically a biological library comprising a variety of organisms containing the gene variants. The biological library according to the invention may be contained in and/or specifically expressed by a population of organisms to create a repertoire of organisms, wherein individual organisms include at least one library member.

According to a specific aspect of the invention there is further provided an organism that comprises a gene variant from such a library, e.g. an organism selected from a repertoire of organisms. The organism as provided according to the invention may be used to express a gene expression product in a suitable expression system, e.g. as a production host cell.

FIGURES

FIG. 1: Non-meiotic in vivo recombination

The homeologous genes A and B (homology of less than 99.5%) were recombined. As the marker sequences and the flanking target sequences are not homologous, recombination/assembly only occurred between genes A and B. As a consequence the hybrid/mosaic DNA contained recombined gene A and B, two markers and both flanking target sequences. The gene mosaic is integrated into the target locus on a target chromosome. Clones that have integrated the entire construct grew on appropriate media which is selective for both markers.

T 5' and T 3' correspond to the target sequences (homology of less than 99.5%) on the yeast genome (ca. 400 bp) addressing the homologous integration onto the chromosome site. M1 and M2 are the flanking markers for the double selection. Gene A and Gene B are related homeologous versions with a given degree of homology (less than 99.5%). Overlapping sequences correspond to the entire ORFs of both genes. After assembly by homeologous recombination in a MMR deficient yeast transformant, the double selection permits the isolation of recombinants.

Figure 2:
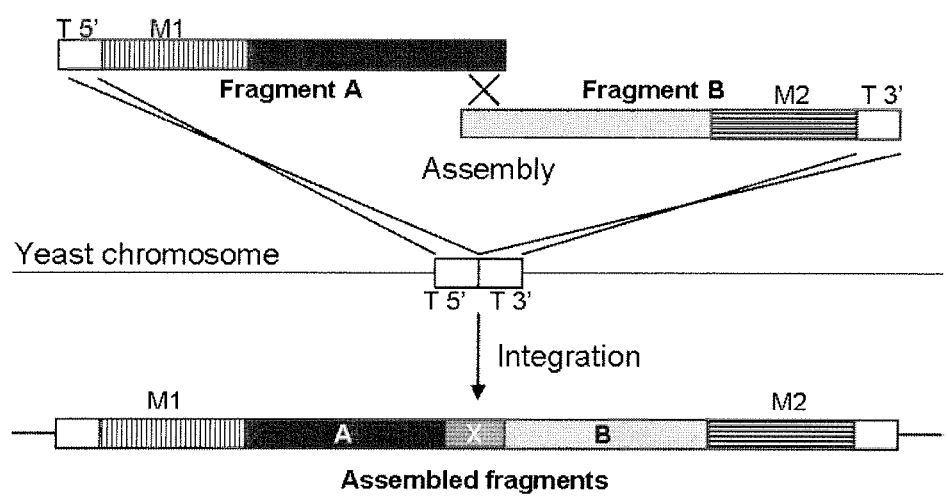

FIG. 2: Recombination and Assembly of DNA by homeologous recombination

This figure shows a schematic presentation of a specific embodiment, wherein the cell is co-transformed with at least two genes, here DNA fragments A and B, which have homology of less than 99.5% on their overlapping fraction of 80 bp. Each DNA fragment was flanked by one selection marker.

Fragment A contained a flanking target sequence that corresponds to the 5' end correct integration site on the chromosome and a hybridizing region that overlaps with fragment B, fragment B contained the flanking target sequence that corresponds to the 3' integration site and a hybridizing region that overlaps with fragment A. Mismatch deficient yeast cells were transformed with the resulting fragments. The resulting transformants were plated on a medium, which is selective for both markers. Clones that can be selected for both markers were isolated, and the integrity of the assembled/integrated cluster, as well as the ORF's reconstitution of genes A and B were verified by molecular analysis of genomic DNA of selected recombinants.

T 5' and T 3' correspond to the target sequences (homology of less than 99.5%) on the yeast genome (ca. 400 bp) addressing the homologous integration onto the chromosome site. M1 and M2 are the flanking markers for the double selection. DNA fragments A and B can be either assembled to one gene, which can be traceable such as GFP, or can represent two genes which are assembled by this method. Overlapping sequences of all genes have homology of less than 99.5% (120 bp), permitting the reconstitution of the ORFs after assembly by homeologous recombination. Double selection permits the recombinant isolation and serves as primary verification of assembly.

Figure 3:
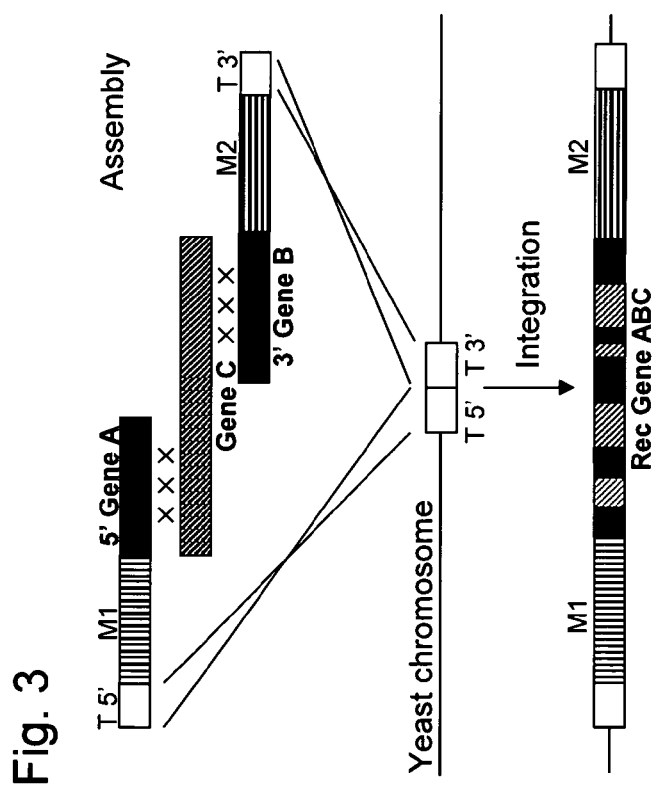

FIG. 3: Recombination and Assembly of genes A, B and C

This figure shows the co-transformation of a further gene C, which has a sequence hybridizing with a flanking sequence of genes A and/or B to obtain assembly of said gene C to genes A and B.

T 5' and T 3' correspond to the target sequences (homology of less than 99.5%) on the yeast genome (ca. 400 bp) addressing the homologous integration onto the chromosome site. M1 and M2 are the flanking markers for the double selection. Gene A, Gene B and Gene C are related homeologous versions with a given degree of homology (less than 99.5%). Overlapping sequences correspond to the 5' part and the 3' part of the genes. The Gene B connects the flanking fragments and a new ORF ABC is reconstituted by sequence similarity. After assembly by homeologous recombination in a MMR deficient yeast transformant, the double selection permits the isolation of recombinants.

Figure 4:
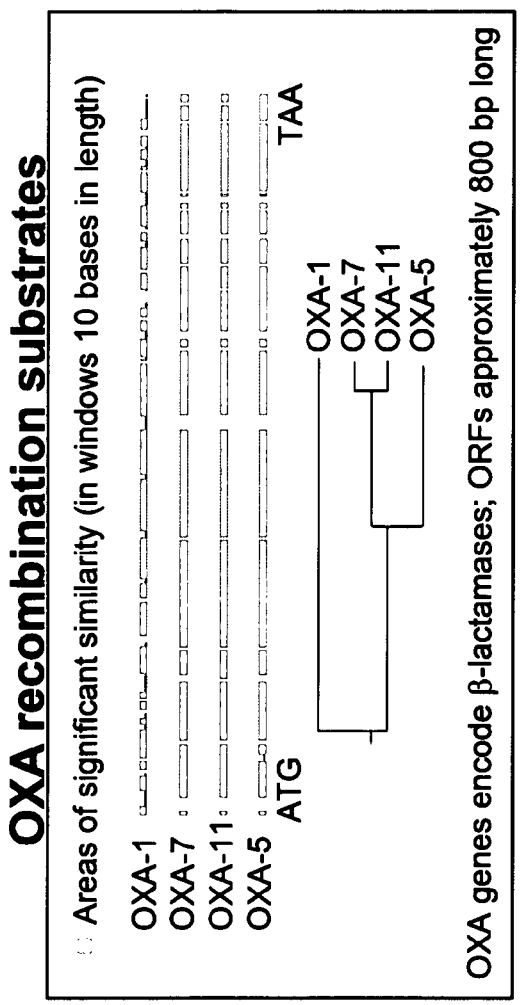

FIG. 4: Oxa recombination substrates

The four genes encode variants of the β-lactamase enzyme. They are related versions with a different degree of homology at the DNA level (from 95% to 49%). The upper panel shows the schematic annealing of the gene's ORFs, with a dendrogramme generated after the alignment. The gene sizes are appr. 800 bp. ATG and TAA means start and stop codons. The bottom table shows the percentage of sequence similarity between the four genes at DNA level.

FIG. 5: Sequences of gene and protein mosaics OXA11/OXA7 (SEQ ID NOs 1-14)

Nucleotide sequences of OXA7 origin are bold and underlined, mutation nucleotide sequences are bold and italic.

Clones were isolated by double selection and DNA used for amplification and sequencing. Only clearly readable sequences of both strands were used. Resulting chromatograms were aligned with a Clustal-like program.

FIG. 6: Sequences of gene and protein mosaics OXA11/OXA5 (SEQ ID NOs 15-38)

Nucleotide sequences of OXA5 origin are bold and underlined, mutation nucleotide sequences are bold and italic.

Clones were isolated by double selection and DNA used for amplification and sequencing. Only clearly readable sequences of both strands were used. Resulting chromatograms were aligned with a Clustal-like program.

FIG. 7: Sequences of parental genes OXA11, OXA7 and OXA5 (SEQ ID NOs 39-41)

FIG. 8: Sequences of clones comprising complex mosaic genes, corresponding to homeologous assembly OXA11/OXA5/OXA7 Sequences clones and results of respective protein annealing: FIG. 8a) OUL3-05-II (SEQ ID NOs 42 and 43), FIG. 8b) OUL3-05-III (SEQ ID NOs 44 and 45), FIG. 8c) OUL3-05-IV (SEQ ID NOs 46 and 47), FIG. 8d) OUL3-05-IX (SEQ ID NOs 48 and 49) and FIG. 8e) OUL3-05-X (SEQ ID NOs 50 and 51) of OXA11/OXA5/OXA7.

Nucleotide sequences of OXA 5 are bold and those corresponding to OXA 7 are underlined. Non bolded, non underlined sequences correspond to OXA 11.

FIG. 9: Sequences of ADH1 genes of *Kluyveromyces lactis, Saccharomyces cerevisiae* and recombinant sequences Nucleotide sequences of *Kluyveromyces lactis* origin are underlined.

FIG. 9a): (SEQ ID NOs 52) ADH *Kluyveromyces*, FIG. 9b): (SEQ ID NOs 53) *Saccharomyces*, FIG. 9c): (SEQ ID NOs 54) clone A02, FIG. 9d): (SEQ ID NOs 55) A03, FIG. 9e): (SEQ ID NOs 56) A05, FIG. 9f): (SEQ ID NOs 57) A06, FIG. 9g): (SEQ ID NOs 58) A10, FIG. 9h): (SEQ ID NOs 59) A11.

DETAILED DESCRIPTION OF THE INVENTION

Therefore, the present invention relates to a novel and highly efficient method for in vivo recombination of homeologous DNA sequences, i.e. similar, but not identical sequences. Hereinafter the term homologous recombination, sometimes called homeologous recombination when homeologous sequences are recombined, refers to the recombination of sequences having a certain homology, which may or may not be identical. Unlike the conventional cloning approach that relies on site-specific digestion and ligation, homologous recombination aligns complementary sequences and enables the exchange between fragments. Recombinant mosaic genes, also called hybrid genes, are generated in the cell through hybridization of sequences having mismatched bases. By such an inventive mutagenesis method it is possible to easily create a diversity for suitable selections and redesign of polypeptides of interest in a time efficient manner.

Specifically, the invention enables the first time the effective recombination and mosaic formation, diversification and assembly of diverse genes in a single step procedure, by employing the functional system of in vivo recombination.

The term "single step procedure" means that several process steps of engineering recombinants, like transformation of cells with a gene, the recombination of genes, generation of a mosaic gene and integration of a gene into the target genome, are technically performed in one method step. Thus, there would be no need of in vitro recombination of DNA carriers prior to in vivo recombination, or any repeating cycles of process steps, including those that employ meiosis. Advantageously, the use of meiotic yeast cells can be avoided.

The single step procedure according to the invention may even include the expression of such engineered recombinants by a host at the same time. Thereby no further manipulation would be necessary to obtain an expression product.

The term "gene mosaic" according to the invention means the combination of at least two different genes with at least one cross-over event. Specifically such a cross-over provides for the combination or mixing of DNA sequences. A gene mosaic may be created by intragenic mixing of gene(s), an intrangenic gene mosaic, and/or gene assembly, optionally assembly of genes with both, intragenic and intergenic cross over(s) or gene mosaic(s).

The term "cross-over" refers to recombination between genes at a site where two DNA strands can exchange genetic information, i.e. at least one nucleotide. The crossover process leads to offspring mosaic genes having different combinations of genes or sequences originating from the parent genes.

Alternatively, other repair mechanisms may be provided, which are not based on cross-over, e.g. nucleotide excision repair or non homologous end joining mechanisms comprising the recognition of incorrect nucleotides, excision and/or replacement after junction of strands.

The term "flanking target sequence" refers to regions of a nucleotide sequence that are complementary to the target of interest, such as a genomic target integration site, including a site of the gene(s) A and/or other gene(s) to be recombined, linear polynucleotides, linear or circular plasmids YAC's and the like. Due to a specific degree of complementation or homology, the flanking target sequence may hybridize with and integrate gene(s) into the target integration site.

The term "genome" of a cell refers to the entirety of an organism's hereditary information, represented by genes and non-coding sequences of DNA, either chromosomal or non-chromosomal genetic elements such as, linear polynucleotides, e.g. including the gene A and/or the other gene(s) to be recombined, viruses, self replicating carriers and vectors, plasmids, and transposable elements, including artificial chromosomes and the like. Artificial chromosomes are linear or circular DNA molecules that contain all the sequences necessary for stable maintenance upon introduction in a cell, where they behave similar to natural chromosomes and therefore are considered as part of the genome.

The term "homology" indicates that two or more nucleotide sequences have (to a certain degree, up to 100%) the same or conserved base pairs at a corresponding position. A homologous sequence, also called complementary, corresponding or matching sequence, as used according to the invention preferably is hybridising with the homologous counterpart sequence, e.g. has at least 30% sequence identity, but less than 99.5% sequence identity, possibly less than 95%, less than 90%, less than 85% or less than 80%, with a respective complementary sequence, with regard to a full-length native DNA sequence or a segment of a DNA sequence as disclosed herein. Preferably, a homologous sequence will have at least about 30% nucleotide sequence identity, preferably at least about 40% identity, more preferably at least about 50% identity, more preferably at least about 60% identity, more preferably at least about 70% identity, more preferably at least about 80% identity, more preferably at least about 90% identity, more preferably at least about 95% identity. Preferred ranges with upper and lower limits as cited above are within the range of 30% and 99.5% corresponding sequence identity. As used herein, the degree of identity always refers to the complementary sequences as well.

"Percent (%) identity" with respect to the nucleotide sequence of a gene is defined as the percentage of nucleotides in a candidate DNA sequence that is identical with the nucleotides in the DNA sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

The term "anchoring" means the binding of a gene or gene mosaic to an integration sequence through a segment called "anchoring sequence" with partial or complete sequence homology, to enable the integration of such gene or gene mosaic into the integration site of a genome. Specifically the anchoring sequence can be a flanking target region homologous or partially homologous to an integration site of a genomic sequence. The preferred anchoring sequence has preferably at least about 70% sequence homology to a target integration site, more preferably at least 80%, 90%, 95% up to 99.55% or complete match with the hybridizing section of the genome.

The integration site may suitably be a defined locus on the host genome, where a high frequency of recombination events would occur. A preferred locus is, for example, the BUD31-HCM1 locus on chromosome III of S. cerevisiae. In general, any further loci on yeast chromosmes that show recombination at high frequencies but no change of cellular viability are preferred.

The term "expression" or "expression system" or "expression cassette" refers to nucleic acid molecules containing a desired coding sequence and control sequences in operable linkage, so that hosts transformed or transfected with these sequences are capable of producing the encoded proteins. In order to effect transformation, the expression system may be included on a vector; however, the relevant DNA may then also be integrated into the host chromosome.

The term "gene" shall also include DNA fragments of a gene, in particular those that are partial genes. A fragment can also contain several open reading frames, either repeats of the same ORF or different ORF's. The term shall specifically include nucleotide sequences, which are non-coding, e.g. untranscribed or untranslated sequences, or encoding polypeptides, in whole or in part.

The term "gene A" as used according to the invention shall mean any nucleotide sequence of a non-coding sequence or a sequence encoding a polypeptide or polypeptides of interest. Gene A is characterized by being presented in the framework of a genetic construct, such as an expression cassette, a linear polynucleotide, a plasmid or vector, which preferably incorporates at least a marker sequence and has a single flanking target sequence, either at the 5' end or 3' end of gene A or the genetic construct. In the method according to the invention the gene A is typically a first gene in a series of genes to be recombined for gene mosaic formation. Gene A is homologous to another gene to be recombined, which is eventually either a variant of gene A, or any of genes B, C, D, E, F, G, H, etc., as the case may be. Thereby only one flanking target sequence per gene A is typically provided for the maximum fidelity purpose. Variants of gene A are called gene A1, A2, A3, etc., which have sequence homology to a certain extent, and optionally similar functional features. The term "at least one gene A" shall mean at least gene A and optionally variants of gene A.

The term "gene B" as used according to the invention shall mean any nucleotide sequence of a non-coding sequence or a sequence encoding a polypeptide or polypeptides of interest, which is chosen for gene mosaic formation with another gene to be recombined, which is eventually either a gene A, a variant of gene B, or any of genes C, D, E, F, G, H, etc., as the case may be. Gene B is homologous to gene A or the other genes to a certain extent to enable mosaic formation with gene A or the other genes to be recombined. In the method according to the invention the gene B is typically the final gene in a series of genes to be recombined for gene mosaic formation. Gene B may be an integral part of the cell genome, or presented in the framework of a genetic construct, such as an expression cassette, a linear polynucleotide, a plasmid or vector, which preferably incorporates at least a marker sequence and has a single flanking target sequence, either at the 5' end or 3' end of gene B or the genetic construct, as a counterpart of the flanking target sequence of gene A, meaning at the opposite end of the gene. If the flanking target sequence of gene A is at the 5' end of gene A, then the gene B would typically have its flanking target sequence on the 3' end and vice versa. Thereby only one flanking target sequence per gene B is typically provided for the maximum fidelity purpose. Gene B may be a variant of gene A. Variants of gene B are called gene B1, B2, B3, etc., which have sequence homology to a certain extent, and optionally similar functional features. The term "at least one gene B" shall mean at least gene B and optionally variants of gene B.

The term "gene C" as used according to the invention shall mean any nucleotide sequence of a non-coding sequence or a sequence encoding a polypeptide of interest. Gene C is characterized by being presented in the framework of a genetic construct, such as an expression cassette, a linear polynucleotide, a plasmid or vector, which optionally incorporates a marker sequence, and further characterised by a segment of its nucleotide sequence that is homologous to a sequence of gene A and/or gene B, a variant of gene C or eventually other genes D, E, F, G, H, etc, as the case may be. Gene C preferably has a single flanking target sequence, either at the 5' end or 3' end of gene C, or a flanking target sequence on both sides. Thereby gene C may partially or completely hybridize with gene A and/or the other genes to recombine, link and assemble the genes. In the method according to the invention the gene C is typically the second gene following gene A in a series of genes to be recombined for gene mosaic formation. Variants of gene C are called C1, C2, C3, etc, which have sequence homology to a certain extent, and optionally similar functional features.

A further gene D may be additionally recombined and assembled through hybridization of its nucleotide sequence or a segment of its nucleotide sequence that is homologous to a sequence of gene C, a variant of gene D or eventually other genes A, B, E, F, G, H, etc, as the case may be to provide the respective recombination and linkage. Gene D preferably has a single flanking target sequence, either at the 5' end or 3' end of gene D, or a flanking target sequence on both sides. In the method according to the invention the gene D is typically the next gene following gene C in a series of genes to be recombined for gene mosaic formation. Variants of gene D are called D1, D2, D3, etc, which have sequence homology to a certain extent, and optionally similar functional features.

A further gene E may be additionally recombined and assembled through a segment of its nucleotide sequence that is homologous to a sequence of gene D, a variant of gene E or eventually other genes A, B, C, F, G, H, etc, as the case may be to provide the respective recombination and linkage. Gene E preferably has a single flanking target sequence, either at the 5' end or 3' end of gene E, or a flanking target sequence on both sides. In the method according to the invention the gene E is typically the next gene following gene D in a series of genes to be recombined for gene mosaic formation. Variants of gene E are called E1, E2, E3, etc, which have sequence homology to a certain extent, and optionally similar functional features.

Further genes F, G, H, etc. may be used accordingly. The series of further genes is understood not to be limited by the number of alphabetical letters. The final chain of genes of interest would be obtained through linkage to the genes A and B to obtain the gene assembly at the integration site of the genome. The so assembled genes of interest may be operably linked to support the expression of the corresponding polypeptides of interest and metabolites, respectively. A specific method of assembly employs the combination of cassettes by in vivo recombination to assemble even a large number of DNA fragments to obtain desired DNA molecules of substantial size. Cassettes representing overlapping sequences are suitably designed to cover the entire desired sequence. In one embodiment the preferred overlaps are at least about 5 bp, preferably at least about 10 bp. In other embodiments, the overlaps may be at least 15, preferably at least 20 up to 1,000 bp.

In one preferred embodiment, some of the cassettes are designed to contain marker sequences that allow for identification. Typically marker sequences are located at sites that tolerate transposon insertions so as to minimize biological effects on the final desired nucleic acid sequence.

In a specific embodiment the host cell is capable of recombining or assembling even a large number of genes or DNA fragments of nucleic acids with overlapping sequences, e.g. at least 2, preferably at least 3, 4, 5, 6, 7, 8, 9, more preferably at least 10 genes or nucleic acid fragments in the host cell by co-transformation with a mixture of said genes or fragments and culturing said host to which the recombined or assembled sequences are transferred.

The genes or DNA fragments to be used according to the invention, either as a whole gene or in part, can either be double-stranded or single stranded. The double-stranded nucleic acid sequences are generally 300-20,000 base pairs and the single stranded fragments are generally shorter and can range from 40 to 10,000 nucleotides. For example, assemblies of as much as 2 Mb up to 500 Mb could be assembled in yeast.

Genomic sequences from a number of organisms are publicly available and can be used with the method according to the invention. These genomic sequences preferably include information obtained from different strains of the host cell or different species to provide homologous sequences having a specific diversity.

The initial genes used as substrates for recombination are a usually a collection of polynucleotides comprising variant forms of a gene. The variant forms show substantial sequence identity to each other sufficient to allow homologous recombination between substrates. The diversity between the polynucleotides can be natural, e.g., allelic or species variants, induced, e.g. error-prone PCR or error-prone recursive sequence recombination, or the result of in vitro recombination. Diversity can also result from resynthesizing genes encoding natural proteins with alternative codon usage. There should be at least sufficient diversity between substrates that recombination can generate more diverse products than there are starting materials. There must be at least two substrates differing in at least one or more positions. The degree of diversity depends on the length of the substrate being recombined and the extent of the functional change to be evolved. Diversity up to 69% of positions is typical.

According to the inventive method it is preferred that the genes A, B, C and further genes share a homology of at least 30% at least at a specific segment designed for hybridization, which would include the full-length gene. The preferred homology percentage is at least 40%, more preferred at least 50%, more preferred at least 60%, more preferred at least 70%, more preferred at least 80%, more preferred at least 90%, even more preferred at least 95% up to less than 99.5%.

It may also be desirable simply to assemble, e.g. to string together and optionally mix such genes with gene variants, to diversify larger genes, e.g. members of an individual metabolic pathway or to assemble multiplicities of metabolic pathways according to this method. Metabolic pathways, which do not exist in nature, can be constructed in this manner. Thus, enzymes which are present in one organism that operate on a desired substrate produced by a different organism lacking such a downstream enzyme, can be encoded in the same organism by virtue of constructing the assembly of genes or partial genes to obtain recombined enzymes. Multiple enzymes can thus be included to construct complex metabolic pathways. This is advantageous if a cluster of polypeptides or partial polypeptides shall be arranged according to their biochemical function within the pathway. Exemplary gene pathways of interest are encoding enzymes for the synthesis of secondary metabolites of industrial interest, such as flavonols, macrolides, polyketides, etc.

In addition, combinatorial libraries can be prepared by mixing fragments, where one or more of the fragments are supplied with the same hybridizing sequences, but different intervening sequences encoding enzymes or other proteins.

Genetic pathways can be constructed in a combinatorial fashion such that each member in the combinatorial library has a different combination of gene variants. For example, a combinatorial library of variants can be constructed from individual DNA elements, where different fragments are recombined and assembled and wherein each of the different fragments has several variants. The recombination and assembly of a metabolic pathway may not need the presence of a marker sequence to prove the successful engineering. The expression of a metabolite in a desired way would already be indicative for the working example. The successful recombination and assembly of the metabolic pathway may, for example, be determined by the detection of the secondary metabolite in the cell culture medium.

Prokaryotic and eukaryotic host cells are both contemplated for use with the disclosed method, including bacterial host cells like *E. coli* or *Bacillus* sp, yeast host cells, such as *S. cerevisiae*, insect host cells, such as *Spodooptera frugiperda* or human host cells, such as HeLa and Jurkat.

Preferred host cells are haploid cells, such as from *Candida* sp, *Pichia* sp and *Saccharomyces* sp.

The inventive method would not use the sexual cycle or meiotic recombination. DNA fragments can be transformed into haploid cells. The transformants can be immediately streaked out on selective plates. The recombinants would then be isolated by PCR or other means, like gap repair.

The inventive process can be conducted in any wild-type or repair deficient prokaryotic or eukaryotic cells, including those with deficiency in nucleic acid repair, such as DNA or RNA repair. In wild-type cells, the suitable integration site is selected, which allows for homoeologous recombination. The method according to the invention as carried out in wild-type cells preferably provides for the recombination of the genes, such as genes A and B, which have at least 80%, preferably at least 90% sequence identity. Though damaged and mismatched DNA is usually repaired and recombination is inhibited, it surprisingly turned out that homoeologous recombination at the integration site is as well possible in such wild-type cells.

Mutations or modifications of the mismatch repair (MMR) system would enhance the frequency of recombination in the cells. Alternatively, other repair deficient systems may be used, such as completely or temporarily knock-outs of DNA repair genes rad1, recQ, which can enhance recombination.

DNA repair deficient cells are preferably used in the method according to the invention. As an example, mismatch repair can be completely or temporarily knocked out, or can be conditional or induced by addition of specific substrates to the cell culture medium, where the cells are cultivated during or after targeted recombination is performed. Specifically, MMR deficiency of a cell can be achieved by any strategy that transiently or permanently impairs the mismatch repair, including the mutation of a gene involved in mismatch repair, treatment with UV light, treatment with chemicals, such as 2-aminopurine, inducible expression or repression of a gene involved in the mismatch repair, for example, via regulatable promoters, which would allow for a transient inactivation and activation.

Bacterial mismatch repair systems have been extensively investigated. In other systems, such as yeast, several genes have been identified whose products share homology with the bacterial mismatch repair proteins, e.g. analogues of the MutS protein, i.e. Msh1, Msh2p, Msh3p, Msh4, Msh5, Msh6p, and analogues of the MutL protein, i.e. Mlh1p, Mlh2p, Mlh3p, and Pms1 in *S. cerevisiae*.

Examples for preferred mismatch repair deficient cells are specific yeast cells, such as *S. cerevisiae* strains with defective or (temporarily) inactivated MSH2, e.g. engineered W303, BY, SK1 strains, such as MXY47 (W303 with disrupted MSH2) strain.

Further preferred systems of MMR are a selection of well-known bacterial strains, such as those described in U.S. Pat. No. 5,912,119, like strains defective for the enzymatic MutHLS mismatch repair system, e.g. of the mutS or mutL type, which is defective for the proteins MutS and MutL, which takes part in the recognition of the mismatches. Preferred strains are for example strains of *S. Typhimurium* using F$^-$ mutL or recombinant *E. Coli* Hfr/*S. Typhimurium* F$^-$ mutL.

Besides, other eukaryotic mismatchrepair deficient cells, like HeLa and Jurkat cells are preferably used according to the invention.

The method according to the invention mainly employs marker assisted selection of a successful recombination product. The use of tools such as molecular markers or DNA fingerprinting can map the genes of interest. This allows screening of a large repertoire of cells to obtain a selection of cells that possess the trait of interest. The screening is based on the presence or absence of a certain gene.

The term "selection marker" as used according to the invention refers to protein-encoding or non-coding DNA sequences with provides for a mark upon successful integration. Specifically, the protein-encoding marker sequences are selected from the group of nutritional markers, pigment markers, antibiotic resistance markers, antibiotic sensitivity markers, fluorescent markers, knock-in markers, activator/binding domain markers and dominant recessive markers, colorimetric markers, and sequences encoding different subunits of an enzyme, which functions only if two or more subunits are expressed in the same cell. The term shall also refer to a traceable gene to be recombined that provides for the direct determination of the gene mosaic, without the need to use separate marker sequences.

A "nutritional marker" is a marker sequence that encodes a gene product which can compensate an auxotrophy of the cell and thus confer prototrophy on that auxotrophic cell. According to the present invention the term "auxotrophy" means that the cell must be grown in medium containing an essential nutrient that cannot be produced by the auxotrophic cell itself. The gene product of the nutritional marker gene promotes the synthesis of this essential nutrient missing in the auxotrophic cell. By successfully expressing the nutritional marker gene it is then not necessary to add this essential nutrient to the cultivation medium in which the cell is grown.

Preferred marker sequences are URA3, LEU2, CAN1, CYH2, TRP1, ADE1 and MET5.

A gene coding for a "pigment marker" is encoding a gene product, which is involved in the synthesis of a pigment which upon expression can stain the cell. Thereby rapid phenotypical detection of cells successfully expressing pigment markers is provided.

An "antibiotic resistance marker" is a gene encoding a gene product, which allows the cell to grow in the presence of antibiotics at a concentration where cells not expressing said product cannot grow.

An "antibiotic sensitivity marker" is a marker gene, wherein the gene product inhibits the growth of cells expressing said marker in the presence of an antibiotic.

A "knock-in" marker is understood as a nucleotide sequence that represents a missing link to a knock-out cell, thus causing the cell to grow upon successful recombination and operation. A knock-out cell is a genetically engineered cell, in which one or more genes have been turned off through a targeted mutation. Such missing genes may be suitably used as knock-in markers.

A "fluorescence marker" shall mean a nucleotide sequence encoding a fluorophore that is detectable by emitting the respective fluorescence signal. Cells may easily be sorted by well-known techniques of flow cytometry on the basis of differential fluorescent labeling.

The genes as used for diversification or recombination can be non-coding sequences or sequences encoding polypeptides or protein encoding sequences or parts or fragments thereof having sufficient sequence length for successful recombination events. More specifically, said genes have a minimum length of 3 bp, preferably at least 100 bp, more preferred at least 300 bp.

The preferred gene mosaics obtained according to the invention are of at least 3, preferably up to 20,000 base pairs, a preferred range would be 300-10,000 bp; particularly preferred are large DNA sequences of at least 500 bp or at least 1,000 bp.

Specifically preferred are gene mosaics that are characterized by at least 3 cross-over events per 700 base pairs, preferably at least 4 cross-overs per 700 base pairs, more preferred at least 5, 6 or 7 cross-overs per 700 base pairs or per 500 base pairs, which include the crossing of single nucleotides, or segments of at least 1, preferably at least 2, 3, 4, 5, 10, 20 up to larger nucleotide sequences.

According to the method of present invention not only odd but also an even number of recombination events can be obtained in one single recombined gene. This is a specific advantage over meiotic in vivo recombination.

Complex patterns of recombinant mosaicism can be obtained by the present method, reaching out high numbers of recombined sequence blocks of different length within one single molecule. Moreover, point-like replacement of nucleotides corresponding to one of the strand templates can be obtained as an important source of diversity respecting the frame of the open reading frames. Moscaicism and point-like exchange are not necessarily conservative at the protein level. Indeed, new amino acids with different polar properties can be generated after recombination, giving novel potential and enzymatic protein properties to the recombinant proteins derived by this method.

Preferably, the genes are protein-encoding sequences or parts of fragments thereof encoding enzymes or proteins of therapeutic or industrial applications. In the following the term "polypeptides" shall include peptides of interest having preferably at least 2 amino acids, preferably at least 3 polypeptides and proteins. The polypeptides of interest preferably are selected, but not limited to enzymes, members of the immunoglobulin superfamily, such as antibodies and antibody domains or fragments, cytokines, vaccine antigens, growth factors and peptides.

Enzymatic catalysts are suitably used in many industrial processes because of their high selectivity. Preferred enzymes as used for diversification according to the invention include proteolytic enzymes, such as subtilisins; cellulolytic enzymes, such as cell-wall loosening enzymes as used in the pulp and paper industry, endoglucanase, amylosucrase, aldolase, sugar kinase, cellulose, amylase, xylanase, glucose dehydrogenase and beta-glucosidase, laccase; lipases as used in the synthesis of fine chemicals, agrochemicals and pharmaceuticals; esterases, e.g. for the production of biofuel. A preferred example of enzyme improvement is the production of an alcohol dehydrogenase with improved thermostability.

It can be shown that even genes encoding multichain polypeptides with complex structures and folds can be recombined and assembled. Preferred examples are members of the immunoglobulin superfamily, among them immunoglobulins and polypeptides sharing structural features with immunoglobulins possessing a domain known as an immunoglobulin domain or fold, including cell surface antigen receptors, co-receptors and co-stimulatory molecules of the immune system, molecules involved in antigen presentation to lymphocytes, cell adhesion molecules, certain cytokine receptors and intracellular muscle proteins. Preferably antibodies or antibody fragments, such as Fab, Fv or scFv are recombined and assembled.

Alternatively, the mosaic genes can also be non-protein encoding sequences, like for example sequences which are involved in the regulation of the expression of a protein-encoding sequence, even regulatory sequences as short and long non coding RNAs. These can be but are not limited to promoter sequences, intron sequences, sequences coding for polyadenylation signals.

In a preferred embodiment of the invention the assembly of a mosaic gene, its recombination with a host genome, and further the expression of the mosaic gene to produce a recombinant polypeptide of interest or a metabolite of said host cell, is performed in a single step procedure.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982).

For in vivo recombination, the gene to be recombined with the genome or other genes is used to transfect the host using standard transfection techniques. In a suitable embodiment DNA providing an origin of replication is included in the construct. The origin of replication may be suitably selected by the skilled person. Depending on the nature of the genes, a supplemental origin of replication may not be required if sequences are already present with the genes or genome that are operable as origins of replication themselves.

Synthetic nucleic acid sequences or cassettes and subsets may be produced in the form of linear polynucleotides, plasmids, megaplasmids, synthetic or artificial chromosomes, such as plant, bacterial, mammalian or yeast artificial chromosomes.

A cell may be transformed by exogenous or heterologous DNA when such DNA has been introduced inside the cell. The transforming DNA may or may not be integrated, i.e. covalently linked into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

The diverse genes substrates may be incorporated into plasmids. The plasmids are often standard cloning vectors, e.g., bacterial multicopy plasmids. The substrates can be incorporated into the same or different plasmids. Often at least two different types of plasmid having different types of selectable markers are used to allow selection for cells containing at least two types of vector.

Plasmids containing diverse gene substrates are initially introduced into cells by any method (e.g., chemical transformation, natural competence, electroporation, biolistics, packaging into phage or viral systems). Often, the plasmids are present at or near saturating concentration (with respect to maximum transfection capacity) to increase the probability of more than one plasmid entering the same cell. The plasmids containing the various substrates can be transfected simultaneously or in multiple rounds. For example, in the latter approach cells can be transfected with a first aliquot of plasmid, transfectants selected and propagated, and then infected with a second aliquot of plasmid. Preferred plasmids are, for example, pUC and pBluscribe derivatives as pMXY9, pMXY12 and pMIX-LAM or YAC derivatives as YCp50.

The rate of evolution can be increased by allowing all gene substrates to participate in recombination. Such can be achieved by subjecting transfected cells to electroporation. The conditions for electroporation are the same as those conventionally used for introducing exogenous DNA into cells. The rate of evolution can also be increased by fusing cells to induce exchange of plasmids or chromosomes. Fusion can be induced by chemical agents, such as PEG, or viral proteins, such as influenza virus hemagglutinin, HSV-1 gB and gD. The rate of evolution can also be increased by use of mutator host cells (e.g., Mut L, S, D, T, H in bacteria, analogous mutants in yeast, and Ataxia telangiectasia human cell lines).

Cells bearing the recombined genes are subject to screening or selection for a desired function. For example, if the substrate being evolved contains a drug resistance gene, one would select for drug resistance.

Typically, in this inventive method of recombination, the final product of recombination that has acquired the desired phenotype differs from starting substrates at 0.1%-50% of positions and has evolved at a rate orders of magnitude in excess (e.g., by at least 10-fold, 100-fold, 1,000-fold, or 10,000 fold) of the rate of naturally acquired mutation. The final gene mosaic product may be transferred to another host more desirable for utilization of the shuffled DNA for production purposes.

In a preferred method according to the invention the host cell is displaying the gene mosaic on the cell surface using well-known cell display systems. By diversification through such hybridization a repertoire of gene variants is produced that can be suitably displayed to create a library of such variants.

Suitable display methods include yeast display and bacterial cell display. Particularly preferred libraries are yeast surface display libraries as used with many applications in protein engineering and library screening. Such libraries provide for the suitable selection of polypeptide variants with enhanced phenotypic properties relative to those of the wild-type polypeptide. Preferably cell-based selection methods are used, e.g. against surface-immobilized ligands. A commonly used selection technique comprises analyzing and comparing properties of the mutant polypeptide obtained from such library with properties of the wild-type polypeptide. Improved desirable properties would include a change of specificity or affinity of binding properties of a ligand polypeptide, which is capable of binding to a receptor. Polypeptide affinity maturation is a particularly preferred embodiment of the invention. Further desirable properties of a variant refer to stability, e.g. thermostability, pH stability, protease stability, solubility, yield or level of secretion of the recombinant polypeptide of interest.

A library obtained by the method according to the invention contains a high percentage of potential lead candidates of functional mosaic genes, which may be expressed in a functional ORF. The preferred library has at least 80% of the gene mosaics contained within a functional ORF, preferably at least 85%, at least 90%, even at least 95%. The library as provided according to the invention specifically is further characterized by the presence of the marker sequence indicating the high percentage of successful hybridization. According to the invention not only odd but also even numbers of mosaic patches can be obtained that increases the number of variants or library members in recombinant libraries produced by said method.

Usually libraries according to the invention comprise at least 10 variants of the gene mosaics, preferably at least 100, more preferred at least 1,000, more preferred at least $10^4$, more preferred at least $10^5$, more preferred at least $10^6$, more preferred at least $10^7$, more preferred at least $10^8$, more preferred at least $10^9$, more preferred at least $10^{10}$, more preferred at least $10^{11}$, up to $10^{12}$, even higher number are feasible.

The method according to the invention can provide a library containing at least $10^2$ independent clones expressing functional variants of gene mosaics. According to the invention it is also provided a pool of preselected independent clones, which is e.g. affinity maturated, which pool comprises preferably at least 10, more preferably at least 100, more preferably at least 1,000, more preferably at least 10,000, even more than 100,000 independent clones. Those libraries, which contain the preselected pools, are preferred sources to select the high affinity variants according to the invention.

Libraries as used according to the invention preferably comprise at least $10^2$ library members, more preferred at least $10^3$, more preferred at least $10^4$, more preferred at least $10^5$, more preferred at least $10^6$ library members, more preferred at least $10^7$, more preferred at least $10^8$, more preferred at least $10^9$, more preferred at least $10^{10}$, more preferred at least $10^{11}$, up to $10^{12}$ members of a library, preferably derived from a parent gene to engineer a new property to the corresponding polypeptide of interest.

Preferably the library is a yeast library and the yeast host cell preferably exhibits at the surface of the cell the polypeptide of interest having biological activity. Alternatively, the products are staying within the cell or are secreted out of the cell. The yeast host cell is preferably selected from the genera *Saccharomyces, Pichia, Hansenula, Schizosaccharomyces, Kluyveromyces, Yarrowia* and *Candida*. Most preferred, the host cell is *Saccharomyces cerevisiae*.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1

Description

In our experimental set-up we use beta lactamase genes of the OXA class as substrate to be recombined. The advantage of the OXA genes lies in the fact that there are homeologous genes of different diversity (from 5-50%) available. These genes are therefore good candidates to test the limits of diversity of in vivo recombination. The genes are also easy to handle (about 800 bp length).

FIG. 4 shows the OXA recombination substrates: genes and homology

TABLE 1

Sequence identity of Oxa genes

|  | Oxa 7 | Oxa 11 | Oxa 5 | Oxa 1 |
|---|---|---|---|---|
| Oxa 7 | 100% | | | |
| Oxa 11 | 95% | 100% | | |
| Oxa 5 | 77% | 78% | 100% | |
| Oxa 1 | 50% | 49% | 50% | 100% |

In the first experiment Oxa 11 was recombined with respectively Oxa 7 (95% identity), Oxa 5 (77% identity) and Oxa 1 (49% identity).

We used yeast strain BY47 derived from a strain collection (EUROSCARF) that contains knock outs of auxotrophic (–ura3, –leu2) marker genes and msh2. The gene defects in uracil and leucine biosynthetic pathway result in auxotrophy i.e. Uracil and Leucine have to be added to the growth media.

In a first step gene fragments were designed that contain on one hand the marker URA3 and OXA11 or on the other hand OXA 5/7/1 respectively with the other marker LEU2. Adjacent to the 5' end of the URA-OXA11 fragment a DNA fragment of about 400 bp was inserted (5' Flanking target sequence) that corresponds to the 5' insertion site in the BUD 31 region of the yeast chromosome. At the 3' end of the OXA 5/7/1 a DNA fragment of about 400 bp (3' flanking target sequence) corresponding to the adjacent 3' site on the chromosome (s. FIG. 3). All fragments were synthesized according to standard protocols at Geneart (Germany).

The synthesized fragments were amplified by PCR and used for transformation.

The URA3-OXA 11 fragment and one of the other OXA-LEU2 fragments were transformed into wild-type (diploid BY26240, Euroscarf) and mismatch deficient strains (haploid a-mater BY06240, msh2–, Euroscarf). The transformation protocol was according to Gietz [Gietz, R. D. and R. A. Woods. (2002) TRANSFORMATION OF YEAST BY THE Liac/SS CARRIER DNA/PEG METHOD. Methods in Enzymology 350: 87-96]. The transformants were plated on plates containing selective media for the selection on the appropriate markers (no Uracil, Leucine). After 72 hours colonies could be observed.

TABLE 2

Number of clones obtained after transformation/selection

| Yeast/trafo | Oxa11/ Oxa11 (1) | Oxa11/ Oxa07 (2) | Oxa11/ Oxa05 (3) | Oxa11/ Oxa1 (4) |
|---|---|---|---|---|
| BY26240 (diploid msh+) | $10^6$ (5) | <10 | 0 | ND |

TABLE 2-continued

Number of clones obtained after transformation/selection

| Yeast/trafo | Oxa11/Oxa11 (1) | Oxa11/Oxa07 (2) | Oxa11/Oxa05 (3) | Oxa11/Oxa1 (4) |
|---|---|---|---|---|
| BY06240 (haploid Δmsh2) | $5 \times 10^4$ | $5 \times 10^3$ | $10^3$ | ND |

(1) Homologous control
(2) 5% of divergence at DNA level
(3) 23% of divergence at DNA level
(4) 51% of divergence at DNA level
(5) Estimated cpu number per ml of transformation mix and µg of DNA on selective media (-ura -leu).

A total of 48 colonies issued from BY06240 transformation were isolated and colony PCR performed (lysis and Herculase PCR based on Cha and Thilly protocol: Specificity, Efficiency and fidelity of PCR, in PCR primer: A laboratory Manual, Dieffenbach and Dveksler eds. 1995, pp 37). Different PCR reactions are performed to verify the correct insertion of the fragments into the target region. 37 clones out of 48 showed correct insertion profiles. From these 37, 31 gave clear and exploitable amplification products for sequencing. The reaction that uses two specific primers flanking the Oxa ORFs only permits the amplification of true recombinants if OXA sequences were actually assembled. Additionally, the obtained product is a correct substrate for direct sequencing. Thus, the positive amplification products were sequenced (GATC).

Results of Sequencing 24 clones out of 31 (those with the clearer positive amplification signals) were sequenced. They corresponded to:
homologous control Oxa11/Oxa11 (SEQ ID NO 39),
  homologous control Oxa07/Oxa07 (SEQ ID NO. 40),
  homologous control Oxa05/Oxa05 (SEQ ID NO 41) fe02 to fe06, fe09 and fe11: Oxa11/Oxa07 (SEQ ID NO. 1 to SEQ ID NO. 14) fe09 and fe13, fe14, fe16 to fe24: Oxa11/Oxa5 (SEQ ID NO. 15 to SEQ ID NO. 38)

For sequencing results of all of the clones see FIGS. 5 and 6 and SEQ ID NOs 1 to 38.

For DNA annealing of Oxa11/Oxa07 clones see FIG. 5, SEQ ID NOs. 1, 3, 5, 7, 9, 11 and 13.

For DNA annealing of Oxa11/Oxa05 clones see FIG. 6, SEQ ID NOs. 15, 17, 19, 21, 23, 25, 27, 29, 31, 33, 35, and 37)

For protein annealing of OXA11/Oxa07 see FIG. 5, SEQ ID NOs. 2, 4, 6, 8, 10, 12 and 14.

For protein annealing of Oxa11/Oxa05 see FIG. 6, SEQ ID NOs. 16, 18, 20, 22, 24, 26, 28, 30, 32, 34, 36 and 38.

Example 2

Description

As a second alternative to generate libraries of complex mosaic genes, three different but related gene sequences were assembled and recombined. As in example 1, OXA gene sequences were used for their assembly in MMR deficient yeast (for OXA gene identity see FIG. 4). As showed in FIG. 3, the principle of mosaic generation is based on the usage of respectively truncated sequences of OXA 11 (gene A) and OXA 7 (gene B) that hybridize with the entire ORF of OXA 5 (gene C). Thus, only assembled and integrated cassettes A-B-C sharing the auxotrophic markers will be selected after transformation.

As in example 1 we used yeast strain BY47 derived from a strain collection (EUROSCARF) that contains knock outs of auxotrophic (-ura3, -leu2) marker genes and a deletion of msh2. The gene defects in uracil and leucine biosynthetic pathway result in auxotrophy: i.e. Uracil and Leucine have to be added to the growth media.

New gene fragments containing truncated genes A and B were obtained in the example 1: URA-Oxa11 (reverse primer annealing on nucleotides 386-406 of OXA11 ORF) and OXA7-Leu (forward primer annealing on nucleotides 421-441 of OXA 7 ORF). The entire ORF of OXA 5 gene was obtained by PCR from fragment OXA5-Leu. The fragment END-Leu was used as in example 1. Purified PCR fragments were used for transformation.

The transformation protocol was according to Gietz [Gietz, R. D. and R. A. Woods. (2002) Transformation of Yeast by the Liac/SS Carrier DNA/PEG Method. Methods in Enzymology 350: 87-96]. The transformants were plated on plates containing selective media for the selection on the appropriate markers (no Uracil, Leucine). After 72 hours colonies could be observed.

TABLE 3

Number of clones obtained after transformation/selection

| Yeast/trafo | Oxa11/Oxa5/Oxa7 (1) | Oxa11/Oxa07 (2) |
|---|---|---|
| BY26240 (diploid msh2+) | $<10^1$ (3) | ND (5) |
| BY06240 (haploid Δmsh2) | $1.4 \times 10^4$ (4) | <5 |

(6) Three OXA sequences to assemble
(7) Middle sequence OXA5 is missing (negative control)
(8) Homeologous recombination background in MMR proficient yeast
(9) Homeologous recombination background in MMR deficient yeast
(10) ND = no colony detected A total of 8 colonies issued from BY06240 transformation were randomly isolated and colony PCR performed (lysis and Herculase PCR based on Cha and Thilly protocol: Specificity, Efficiency and fidelity of PCR, in PCR primer: A laboratory Manual, Dieffenbach and Dveksler eds. 1995, pp 37). Different PCR reactions were performed to verify the correct insertion of the fragments into the target region. 7 clones out of 8 showed correct insertion profiles. From these 7 gave clear and exploitable amplification products for sequencing. The reaction that uses two specific primers flanking the Oxa ORFs only permits the amplification of true recombinants if OXA sequences were actually assembled. Additionally, the obtained product is a correct substrate for direct sequencing. Thus, the positive amplification products were sequenced (GATC).

Results of Sequencing 7 clones out of 8 (those with the clearer positive amplification signals) were sequenced 5 exploitable sequences were obtained. They corresponded all to homeologous assembly OXA11/OXA5/OXA7 from clones OUL3-05-II, OUL3-05-III, OUL3-05-IV, OUL3-05-IX and OUL3-05-X.

For sequencing results of all of the clones and protein annealing see FIG. 8: OUL3-05-II (SEQ ID NOs 42 and 43), OUL3-05-III (SEQ ID NOs 44 and 45), OUL3-05-IV (SEQ ID NOs 46 and 47), OUL3-05-IX (SEQ ID NOs 48 and 49) and OUL3-05-X (SEQ ID NOs 50 and 51) of OXA11/OXA5/OXA7.

Discussion

This simple transformation method of mitotic MMR deficient cells with divergent sequences as templates for the assembly by the cell and generation of diversity by in vivo recombination has been proven (FIGS. 5, 6 and 8).

Complex patterns of recombinant mosaicism have been obtained by the method described in example 1, reaching out at least 17 patches of different length into one single molecule of 800 bp (i.e. clones fe19 (SEQ ID NO 27) and fe20 (SEQ ID NO. 28). Recombination events seem to take place all the long of the sequences.

Moreover, point-like replacement of nucleotide corresponding to one of the strand templates were observed as an important source of diversity respecting the frame of the ORFs (i.e. clones fe19 (SEQ ID NO. 27) and fe20 (SEQ ID NO. 29).

In addition, this recombination method produced mosaics from more than two related genes as shown in the example 2 by using sequences from three related genes (OXA 11, OXA 7 and OXA 5) at the same time (i.e. clones OUL3-05-III and OUL3-05-IX). This is a highly efficient way to recombine regions of interest from several genes, and represents a new source of divergence based on the generation of mosaic genes libraries in vivo.

None of the recombinant clones yielded truncated protein products as verified by in silico analysis of translated DNAs (FIGS. 5, 6 and 8).

Only 1 clone (fe15) out of 21 showed a parental profile (data not shown).

Moscaicism and point-like exchange are not necessarily conservative at the protein level. Indeed, new amino acids with different polar properties were generated after recombination, giving novel potential and enzymatic protein properties to the recombinant muteins (i.e. clones fe19 (SEQ ID NO. 27) and fe20 (SEQ ID NO. 29)

One very attractive trait of the recombinant generation by this approach making recombinant libraries richer is the fact that not only odd but also even number of recombination events could be obtained (i.e. fe06 (SEQ ID NO 7), fe11 (SEQ ID NO 13), fe13 (SEQ ID NO 17), fe19 (SEQ ID NO 27), compared to the meiotic recombination approach, by which only odd events could be represented into the library.

Some point mutations, not related to parental templates, were observed in a few numbers of sequences (i.e. fe16 (SEQ ID NO 21) and fe17 (SEQ ID NO 23). In all those cases, the mutations didn't change the reading frame of the resulting ORFs.

Example 3

ADH 1

In a second example we choose an endogenous DNA as target for recombination. Alcohol dehydrogenase 1 (ADH1) is the key enzyme for the production of Ethanol in yeast *Saccharomyces cerevisiae*. It is of industrial interest to generate improved Adh1 variants.

The strains BY06246 from Euroscarf and W303 from Euroscarf are used for this experiment.

The *Saccharomyces cerevisiae* ADH1 gene is already located on chromosome XV. Therefore, introduction of only one homeologous gene is sufficient for recombination. In order to assure that recombined recombinants will not further mutate we also re-establish the mismatch repair wild-type. Therefore we additionally add a fragment containing functional MSH2 gene with its promoter and terminator regions.

As partner for somatic gene recombination we choose the *Kluyveromyces thermotholerans/Lachancea thermotolerans* ADH1 gene which has 82% homology with the *Saccharomyces cerevisiae* gene. Two fragments are designed. One fragment contains the *K. thermotholerans* ADH1 open reading frame. At its 3' end a fragment containing 296 bp of the terminator region from TRP1 gene cassette comprising 283 bp of the promoter and the first 743 bp of URA3 ORF from *Kluyveromyces lactis* is designed. The URA3 gene product of *K. lactis* can complement the ura3 defect in *Saccharomyces cerevisiae*. The second fragment contains the last 160 bp of URA3 and 223 bp of the terminator region of URA3. This sequence is followed by 468 bp of the endogenous MSH2 promoter and the MSH2 ORF (2894 bp) and 242 bp of the TEF1 terminator. The fragment is flanked at the 3' side by a 403 bp sequence which is identical to the of the insertion site on Chr. XV. All fragments are synthesized at Geneart.

As the 3' end of the ADH1-URA3 fragment and the 5' end of the URA3-MSH2 fragment are homologous the two fragments can assemble. After assembly the recombination with the *Saccharomyces cerevisiae* ADH1 gene and the integraton step takes place.

After transformation several clones were randomly isolated and DNA was prepared. The DNA of the ADH recombinants was sequenced. The underlined sequences are derived from the ADH *Kluyveromyces lactis*, the other from ADH *Saccharomyces cerevisiae* (see FIG. 9).

The invention claimed is:

1. A method for generating a gene mosaic by somatic in vivo recombination, comprising:
   a) in a single step procedure:
      (i) transforming a repair deficient host cell with at least a first gene having a sequence homology of less than 99.5% to a second gene to be recombined with the first gene, the second gene being an integral part of the host cell genome or present in a framework of a genetic construct in the host cell,
      (ii) recombining said genes, and
      (iii) generating a gene mosaic from the first and second genes, the gene mosaic being integrated into a chromosome of the host cell at an integration site of a target genome, wherein the first gene has a single flanking target sequence either at the 5' end or 3' end anchoring to the 5' or 3' end of said integration site, and
   b) selecting clones comprising the gene mosaic.

2. A method according to claim 1, wherein a selection marker is used in the gene mosaic and the clones are selected according to the presence of the selection marker.

3. A method according to claim 1, wherein said second gene is part of the genome of the host cell.

4. A method according to any of claim 1, wherein the cell is co-transformed with the first gene and the second gene, wherein said single flanking target sequence of the first gene is anchoring to the 5' end of the integration site on said target genome, and wherein the second gene is linked to a single flanking target sequence anchoring to the 3' end of the integration site.

5. A method according to claim 1, wherein the host cell a is co-transformed with a third gene which has a sequence hybridizing with a sequence of the first gene and/or with a sequence of the second gene to obtain assembly of the third gene with the first gene and/or with the second gene.

6. A method according to claim 1, wherein the first gene and/or the second gene is coding for a polypeptide or part of a polypeptide having an activity.

7. A method according to claim 5, wherein multiple genes coding for polypeptides of a biochemical pathway are recombined and assembled.

8. A method according to claim 1, wherein the cell is a eukaryotic cell or a prokaryotic cell.

9. A method according to claim 8, wherein the cell is a fungal cell of a genus selected from the group consisting of *Saccharomyces, Candida, Kluyveromyces, Hansenula, Schizosaccharomyces, Yarrowia, Pichia* and *Aspergillus*.

10. A method according to claim 1, wherein the flanking target sequence is at least 5 bp.

11. A method according to claim 1, wherein the flanking target sequence has homology in the range of 30% to 99.5% with an anchoring sequence of said integration site.

12. A method according to claim 1, wherein a selection marker is used, wherein the selection marker is selected from the group consisting of nutrition auxotrophic markers, antibiotics resistance markers, fluorescent markers, knock-in markers, activator/binding domain markers, dominant recessive markers and colorimetric markers.

13. A method according to claim 1, wherein said first and second genes are each comprised in a linear polynucleotide, a vector or a yeast artificial chromosome.

14. A method according to claim 1, wherein said genes are linear polynucleotides of 300 to 20,000 bp.

15. A method according to claim 1, wherein at least one clone having an intragenic gene mosaic is selected.

16. A method according to claim 1, wherein at least one clone having a gene assembly and at least one intragenic gene mosaic is selected.

17. A method according to claim 1, wherein gene mosaics of at least 3 and up to 20,000 base pairs with at least 3 cross-over events per 700 bp are obtained.

18. A method according to claim 1, wherein the genes are non-coding sequences or encoding variants of a polypeptide selected from the group consisting of enzymes, antibodies or parts thereof, cytokines, growth factors, vaccine antigens and peptides.

19. A method of cell display of gene variants, comprising creating a variety of gene mosaics in cells using the method according to claim 1, and displaying said variety on the surface of said cells to obtain a library of mosaics.

20. The method of claim 8, wherein the cell is a eukaryotic cell selected from the group consisting of a fungal cell, a mammalian cell and a plant cell.

* * * * *